(12) United States Patent
McArthur

(10) Patent No.: US 9,702,012 B2
(45) Date of Patent: Jul. 11, 2017

(54) TRANSCRIPTION FACTOR DECOYS, COMPOSITIONS AND METHODS

(75) Inventor: Michael McArthur, Rockland All Saints (GB)

(73) Assignee: PROCARTA BIOSYSTEMS LTD, Norwich (GB)

( * ) Notice: Subject to any disclaimer, the term of this patent is extended or adjusted under 35 U.S.C. 154(b) by 930 days.

(21) Appl. No.: 12/681,588

(22) PCT Filed: Oct. 3, 2008

(86) PCT No.: PCT/GB2008/003353
§ 371 (c)(1),
(2), (4) Date: Aug. 20, 2010

(87) PCT Pub. No.: WO2009/044154
PCT Pub. Date: Apr. 9, 2009

(65) Prior Publication Data
US 2011/0009476 A1    Jan. 13, 2011

(30) Foreign Application Priority Data
Oct. 3, 2007   (GB) .................................. 0719367.5

(51) Int. Cl.
C07H 21/04    (2006.01)
C12Q 1/68     (2006.01)
C12N 15/10    (2006.01)

(52) U.S. Cl.
CPC ......... *C12Q 1/689* (2013.01); *C12N 15/1048* (2013.01); *C12N 15/1079* (2013.01); *C12N 15/1086* (2013.01); *C12Q 1/6811* (2013.01); *C12Q 1/6897* (2013.01); *C12Q 2600/136* (2013.01); *C12Q 2600/158* (2013.01)

(58) Field of Classification Search
CPC .............................. C07H 21/02; C12Q 1/6811
See application file for complete search history.

(56) References Cited

U.S. PATENT DOCUMENTS

| | | | |
|---|---|---|---|
| 5,977,084 A | 11/1999 | Szoka, Jr. et al. | |
| 6,090,619 A | 7/2000 | Weissig et al. | |
| 6,133,026 A | 10/2000 | Huang et al. | |
| 6,551,795 B1 | 4/2003 | Rubenfield | |
| 9,024,005 B2 | 5/2015 | McArthur | |
| 2004/0014956 A1 | 1/2004 | Woolf et al. | |
| 2004/0110235 A1 | 6/2004 | Epstein et al. | |
| 2005/0227257 A1 | 10/2005 | Abravaya et al. | |
| 2007/0011759 A1 | 1/2007 | Khan | |

(Continued)

FOREIGN PATENT DOCUMENTS

EP    2266626    12/2010
WO    WO 93/19768    10/1993

(Continued)

OTHER PUBLICATIONS

C. Lim, "Sequence-independent inhibition of RNA transcription by DNA dumbbells and other decoys," Nucleic Acids Research, 1997, pp. 575-581, vol. 25, No. 3, XP002522068.

(Continued)

*Primary Examiner* — Reza Ghafoorian
(74) *Attorney, Agent, or Firm* — Knobbe, Martens, Olson & Bear LLP

(57) ABSTRACT

Compositions and methods for identifying and using cis-regulatory and decoy sequences.

7 Claims, 29 Drawing Sheets

(56) References Cited

U.S. PATENT DOCUMENTS

| | | |
|---|---|---|
| 2007/0014840 A1 | 1/2007 | Lee et al. |
| 2007/0031850 A1 | 2/2007 | Mounts et al. |
| 2007/0104775 A1 | 5/2007 | Panzner et al. |
| 2007/0166740 A1 | 7/2007 | Heil et al. |
| 2008/0171322 A1 | 7/2008 | Heyduk et al. |
| 2009/0099108 A1 | 4/2009 | Jones |
| 2011/0251264 A1 | 10/2011 | McArthur et al. |
| 2013/0252881 A1 | 9/2013 | McArthur |
| 2014/0080190 A1 | 3/2014 | Atkinson et al. |
| 2014/0274800 A1 | 9/2014 | McArthur |
| 2015/0196652 A1 | 7/2015 | McArthur |

FOREIGN PATENT DOCUMENTS

| | | |
|---|---|---|
| WO | WO 94/23699 | 10/1994 |
| WO | WO 95/34647 | 12/1995 |
| WO | WO 97/30070 A1 | 8/1997 |
| WO | WO 99/13096 A1 | 3/1999 |
| WO | WO 01/75067 A2 | 10/2001 |
| WO | WO 2004/016754 | 2/2004 |
| WO | WO 2004/030699 A1 | 4/2004 |
| WO | WO 2004/067709 A2 | 8/2004 |
| WO | WO2005062854 * | 7/2005 |
| WO | WO 2006/096140 | 9/2006 |
| WO | WO 2007/013480 | 2/2007 |
| WO | WO 2007/137301 | 11/2007 |
| WO | WO 2008/024389 | 2/2008 |
| WO | WO 2008/092142 | 7/2008 |
| WO | WO 2010/038083 A2 | 4/2010 |
| WO | WO 2011/098829 A1 | 8/2011 |
| WO | WO 2011/121357 | 10/2011 |

OTHER PUBLICATIONS

M. Toledano, et al., "Redox-Dependent Shift of OxyR-DNA Contacts along an Extended DNA-Binding Site: A Mechanism for Differential Promoter Selection," Cell, Sep. 9, 1994, pp. 897-909, vol. 78, XP024246465.

"Prokaryotic gene therapy to combat multidrug resistant bacterial infection," Gene Therapy, 2000, 723-725, vol. 7, XP009004366.

R. Cranenburgh, et al., "*Escherichia coli* strains that allow antibiotic-free plasmid selection and maintenance by repressor titration," Nucleic Acids Research, 2001, vol. 29, No. 5 e26, Oxford University Press, XP-002514866.

T. Onizuka, et al., "$CO_2$ response for expression of ribulose-1,5-bisphosphate carboxylase/oxygenase genes in inhibited by AT-rich decoy in the cyanobacterium," FEBS Letters, FEBS 27178, 2003, pp. 42-46, vol. 542.

Arthur et al., "Regulated interactions between partner and non-partner sensors and response regulators that control glycopeptide resistance gene expression in enterococci," *Microbiology*, vol. 145, pp. 1849-1858 (1999).

Choi et al., "Increasing vancomycin susceptibility in vancomycin resistant enterococci by vanH promoter and ddl transformation," *Journal of Infection*, vol. 48, pp. 314-319 (2004).

Torres Viera et al., "Restoration of Vancomycin Susceptibility in *Enterococcus faecalis* by Antiresistance Determinant Gene Transfer," *Antimicrobial Agents and Chemotherapy*, vol. 45(3), pp. 973-975 (Mar. 2001).

Chen et al. Nucleic Acids Research, 2007, 35:6762-6777.

Chen et al. Nucleic Acids Research, 2007, 35:6762-6777 (supplementary material).

Maki et al., Antimicrobial Agents Chemother, (2004) 48:1953.

Morris et al., "DNA Distortion and Nucleation of Local DNA Unwinding within Sigma-54 (σn) Holoenzyme Closed Promoter Complexes," The Journal of Biological Chemistry, vol. 269(15), Issue of Apr. 15, pp. 11563-11571 (1994).

Ow et al. PNAS 80:2524-2528, 1983.

Jefferson et al., "The teicoplanin-associated locus regulator (TcaR) and the intercellular adhesion locus regulator (IcaR) are transcriptional inhibitors of the ica locus in *Staphylococcus aureus*," J. Bacteriol, vol. 186(8), pp. 2449-2456 (Apr. 2004).

Abe et al "Contribution of Asian mouse subspecies Mus musculus molossinus to genomic constitution . . ." Gene Research vol. 14 No. 12, Jan. 1, 2004. EMBL database Accession No. EMBL AG504103 Jun. 4, 2004. Mus musculus molossinus DNA clone MSMg01-405L22.T7 genomic survey sequence.

Barrios et al., Compilation and analysis of σ54-dependent promoter sequences, Nucleic Acids Research, 1999, vol. 27, No. 22, pp. 4305-4313.

Boyd et al., "VanG-Type Vancomycin-Resistant Enterococcus faecilis Strains Isolated in Canada," Antimicrobial Agents and Chemotherapy, Jun. 2006, vol. 50(6), pp. 2217-2221.

Buck et al. Nature. vol. 358, Jul. 30, 1992, p. 422-424.

Buck et al., "The Bacterial Enhancer-Dependent σ54(σN) Transcription Factor," J. Bacteriol., Aug. 2000, vol. 182(15), pp. 4129-4136.

Chang et al., "Conformational Changes in DNA upon Ligand Binding Monitored by Circular Dichroism," Int. J. Mol. Sci., vol. 13, pp. 3394-3413 (2012).

Coleman et al., "The Role of Sigma Factors in Regulating Bacterial Stress Responses and Pathogenesis," in Molecular Paradigms of Infectious Disease, A Bacterial Perspective, Nickerson & Schurr, Eds., Springer, Chapter 12, pp. 438-501 (2006).

Coles et al., Trial of Dequalinium for Skin Infections, British Medical Jl., Oct. 25, 1958, pp. 1014-1017.

D'Souza et al., "DQAsome-mediated delivery of plasmid DNA toward mitochondria in living cells," Journal of Controlled Release, vol. 92, pp. 189-197 (2003).

Dapa et al., "Multiple Factors Modulate Biofilm Formation by the Anaerobic Pathogen Clostridium difficile," Journal of Bacteriology, vol. 195(3), pp. 545-555 (Feb. 2013), with additional data from online version.

Dawson et al., "Characterisation of Clostridium difficile Biofilm Formation, a Role for Spo0A," PLOS One, vol. 7(12), pp. 1-13 (Dec. 2012), with additional data from online version.

Deakin et al., "The Clostridium difficile spo0A Gene Is a Persistence and Transmission Factor," Infection and Immunity, vol. 80(8), pp. 2704-2711 (Aug. 2012), with additional data from online version.

Endoh et al. (Molecular Microbiology, vol. 55, issue 3 pp. 897-911, 2005).

Fuhrhop et al., "Bolaamphiphiles," Chem. Rev., vol. 104, pp. 2901-2937 (2004).

Galanakis, J. Med. Chem. 1995, 38, 3536-3546.

Gross et al., Bacterial Sigma Factors, Chapter 6, pp. 129-176, Cold Spring Harbor, 1992.

Gutierrez-Lugo et al., Dequalinium, a New Inhibitor of *Mycobacterium tuberculosis* Mycothiol Ligase Identified by High-Throughput Screening, Jl. of Molecular Screening, 2009 14:643 (original online publication date Jun. 12, 2009).

Heyes et al, "Antitumor Evaluation of a Ribonuclease Resistant Double-Stranded RNA-Polyquaternary Ammonium Complex (BRL 10739)," European J. of Cancer, 1965, Permagon, vol. 10, No. 7, Jul. 1, 1974. Abstract, p. 431, col. 2 para 2, ph 432 col. 1 Para 1, fig 1.

Hugo et al., "Mode of Action of the Antibacterial Compound Dequalinium Acetate," Applied Microbiology, vol. 17(1), pp. 118-127 (Jan. 1969).

International Search Report and Written Opinion of the International Searching Authority for PCT/GB2014/050752, mailed on Jun. 16, 2014.

Kypr et al., "Circular dichroism and conformational polymorphism of DNA," Nucleic Acids Research, vol. 37(6), pp. 1713-1725 (2009).

Leang et al., "Genome-wide analysis of the RpoN regulon in Geobacter sulfurreducens", BMC Genomics, Biomed Central, London, GB, vol. 10, No. 1, Jul. 22, 2009 (Jul. 22, 2009), p. 331, XP021056141.

Lee et al., "Advantages of the Circular Dumbbell Decoy in Gene Therapy and Studies of Gene Regulation," Current Drug Targets, vol. 4, pp. 619-623 (2003).

(56) References Cited

OTHER PUBLICATIONS

Legendre et al, "Biochemical, Morphological and Functional Analyses of a Cyclic Peptide, Phospholipid, and DNA Ternary Complex Used for Gene Delivery," J. Liposome Res., vol. 8(3), pp. 347-366, Aug. 1, 1998.
Mann and Dzau, Therapeutic applications of transcription factor decoy oligonucleotides, The Journal of Clinical Investigation, Nov. 2000, vol. 106, No. 9, pp. 1071-1075.
Mann, "Transcription Factor Decoys: A New Model for Disease Intervention", Annals of the New York Academy of Sciences, vol. 1058, No. 1, Nov. 1, 2005 (Nov. 1, 2005), pp. 128-139, XP55001514.
McArthur et al. "Manipulating and understanding antibiotic production in Streptomyces coelicolor A3(2) with decoy oligonucleotides," PNAS, vol. 105(3), pp. 1020-1025 (Jan. 22, 2008).
Moellering Jr., "Discovering new antimicrobial agents," International Journal of Antimicrobial Agents, vol. 37, pp. 2-9 (2011).
Morishita et al., "Application of Transcription Factor "Decoy" Strategy as Means of Gene Therapy," Circulation Research, 1998, vol. 82, pp. 1023-1028.
Oren and Shai, Mode of Linear Amphipathic a-Helical Antimicrobial Peptides, Biopolymers (Peptide Science) vol. 47, 451-463 (1998).
Parker et al, "Methodologies for Monitoring Nanoparticle Formation by Self-Assembly of DNA with Poly(L-lysine)," Analytical Biochem., Academic Press Inc., NY, vol. 302, No. 1, Mar. 1, 2002, pp. 75-80, abstract, p. 76, col. 1, para 2.
Patil et al., "DNA-based Therapeutics and DNA Delivery Systems: A Comprehensive Review," The AAPS Journal, vol. 7(1), Article 9, pp. E61-E77 (2005).
Prouty et al. Molecular Microbiology (2001) 39(6), 1595-1609.
Quagliotto et al., "Gemini Pyridinium Surfactants: Synthesis and Conductometric Study of a Novel Class of Amphiphiles," J. Org. Chem., vol. 68(20), pp. 7651-7660 (2003).
Quagliotto et al., "Synthesis and Characterization of Highly Fluorinated Gemini Pyridinium Surfactants," Eur. J. Org. Chem., pp. 3167-3177 (2009).
Rosenbusch et al., "C. difficile 630Δerm SpoOA Regulates Sporulation, but Does Not Contribute to Toxin Production, by Direct High-Affinity Binding to Target DNA," PLOS One, vol. 7(10), pp. 1-12 (Oct. 2012), with additional data from online version.
Saujet et al., "The Key Sigma Factor of Transition Phase, SigH, Controls Sporulation, Metabolism, and Virulence Factor Expression in Clostridium difficile," Journal of Bacteriology, vol. 193(13), pp. 3186-3196 (Jul. 2011), with additional data from online version.
Sebaihia et al., "The multidrug-resistant human pathogen Clostridium difficile has a highly mobile, mosaic genome," Nature Genetics, vol. 18(7), pp. 779-786 (Jul. 2006), with additional data from online version.
Sharma et al., "Heterocyclic Cationic Gemini Surfactants: A Comparative Overview of Their Synthesis, Self-assembling, Physicochemical, and Biological Properties," Medicinal Research Reviews, vol. 34(1), pp. 1-44 (2014).
Shiraishi et al., "Targeted Delivery of Plasmid DNA into the Nucleus of Cells via Nuclear Localization Signal Peptide Conjugated to DNA Intercalating Bis- and Trisacridines," Bioconjugate Chem., vol. 16, pp. 1112-1116 (2005).
Stabler et al., "Comparative genome and phenotypic analysis of Clostridium difficile 027 strains provides insight into the evolution of a hypervirulent bacterium," Genome Biology, vol. 10(9), pp. R102-R102.15 (2009), with additional data from online version.
Theuretzbacher, "Accelerating resistance, inadequate antibacterial drug pipelines and international Responses," International Journal of Antimicrobial Agents, vol. 39, pp. 295-299 (2012).
Underwood et al., "Characterization of the Sporulation Initiation Pathway of Clostridium difficile and Its Role in Toxin Production," Journal of Bacteriology, vol. 191(23), pp. 7296-7305 (Dec. 2009), with additional data from online version.
Weissig et al., "Cationic bolasomes with delocalized charge centers as mitochondria-specific DNA delivery systems," Advanced Drug Delivery Reviews, vol. 49, pp. 127-149 (2001).
Weissig et al., "DNA binding cationic bolasomes with delocalized charge center A structure-activity relationship study," S.T.P. Pharma Sciences, vol. 11(1), pp. 91-96 (2001).
Weissig et al., "DQAsomes: A Novel Potential Drug and Gene Delivery System Made from Dequalinium™," Pharmaceutical Res., vol. 15(2), pp. 334-337 (1998).
Weissig et al., "Liposomes and Liposome-like Vesicles for Drug and DNA Delivery to Mitochondria," Journal of Liposome Research, vol. 16, pp. 249-264 (2006).
Weissig et al., "Selective DNA Release from DQAsome/DNA Complexes at Mitochondria-Like Membranes," Drug Delivery, vol. 7, pp. 1-5 (2000).
Zhang et al., "The hydrolysis of cationic polycarboxybetaine esters to zwitterionic polycarboxybetaines with controlled properties," J. Biomaterials, 2008, vol. 29, No. 36, Dec. 2008. Abstract, p. 4720, col. 2, para 5, para 6, structure 1, table 1.
Zubkov et al., "Synthesis and Antimicrobial Activity of 3-Aminomethyl-Substituted Quinolones," UDC 54.057:547.831.7/ 8:615.28 (2003).
Liu et al., Clinical Practice Guidelines by the Infectious Diseases Society of America for the Treatment of Methicillin-Resistant *Staphylococcus aureus* Infections in Adults and Children, Clin. Infect. Diseases Advance, CID 2011 :52, 1-38, Jan. 4, 2011.
Viera et al., Restoration of Vancomycin Susceptibility in Enterococcus faecilis by Antiresistance Determinant Gene Transfer, Antimicrobial Agents and Chemotherapy, Mar. 2001, p. 973-975.
Kanhere et al. Nucleic Acids Research, 2005, 33:3165-3175.
Buck et al., "Activator-independent formation of a closed complex between σ54-hoioenzyme and nifH and nifU promoters of Klebsiella pneumoniae," Molecular Microbiology, vol. 6(12), pp. 1625-1630 (1992).
Bock et al. Nature. vol. 35, p. 564-566, Feb. 6, 1992.

\* cited by examiner n[snare] libraries can be created from genome fragments, complete genomes or random oligonucleotides to maximize number of TFD targets they contain

*S. cinnamoneous* bioassay selected clone transformed n[snare]

n[snare]™ derived from cinnamycin cluster n[snare] libraries to upregulate antibiotic production Analyze fragments by PAGE to map positions of DNA-protein boundaries

Figure 24

```
CTTGG TTTTT CCAAG AGAAGAGC ccg cca tgg cgg ccg cgg gaa ttc NNN NNN TCA CTA GTG AAT TCG CGG CCG CCT GCTCTTCG CCG TCA AAA AGA CGG a
GAACC AAAAA GGTTC TCTTCTCG ggc ggt acc gcc ggc gcc ctt aag NNN NNN AGT GAT CAC TTA AGC GCC GGA CGTGAAGC GGC AGT TTT TCT GCC T WITH Nt.BspQI (NEB: R0644L)

CTTGG TTTTT CCAAG AGAAGAGC ccg cca tgg cgg ccg cgg gaa ttc NNN NNN TCA CTA GTG AAT TCG CGG CCG CCT GCTCTTCG
                 TCTTCTCG ggc ggt acc gcc ggc gcc ctt aag NNN NNN AGT GAT CAC TTA AGC GCC GGA CGTGAAGC GGC AGT TTT TCT GCC

E WITH T4 DNA POLYMERASE
```

Figure 27

Table 1. Efflux-mediated resistance to non-fluoroquinolone antimicrobials

| Antimicrobial | Efflux system | Pump family | Gene location | Organism(s) | Reference[a] |
|---|---|---|---|---|---|
| Chloramphenicol & florfenicol | | | | | |
| Chloramphenicol | Cml, CmlA, CmlB | MF | mostly plasmid; some chromosome | P. aeruginosa, E. aerogenes, K. pneumonia, S. enterica serovar Typhimurium | 48 |
| | Cml, Cmlv, Cmr, Cmx, CmrA | ? | plasmid & chromosome | Streptomyces spp., Corynebacterium spp., Rhodococcus spp. | 48 |
| | MdfA[b] | MF | chromosome | E. coli | 74 |
| | MexEF-OprN[c], variety of three-component RND pumps[d] | RND | chromosome | P. aeruginosa, several Gram-negative bacteria | 74, 79 |
| | OqxAB | RND | plasmid | E. coli | 84 |
| Chloramphenicol, florfenicol | Flo, FloR, pp-Flo | MF | plasmid & chromosome | E. coli, K. pneumoniae, V. cholerae, S. enterica serovar Typhimurium | 48 |
| | FexA | ? | plasmid | S. lentus | 70 |
| Macrolides, lincosamides, streptogramins & ketolides | | | | | |
| Macrolides | Mef(A) | MF | chromosome | Streptococcus spp., Corynebacterium spp., Enterococcus spp., Micrococcus spp., Staphylococcus spp., Acinetobacter spp., Bacteroides spp., Neisseria spp., several Enterobacteriaceae and Pseudomonadaceae commensals | 146, 176 |
| Macrolides, type B streptogramins | Msr(A) | ABC | plasmid | Staphylococcus spp. | 173, 175 |
| | Msr(C) | ABC | chromosome | E. faecium | 146, 180 |
| Macrolides, ketolides | Msr(D) | ABC | chromosome | S. pneumoniae | 149 |
| Macrolides, lincosamides, type A streptogramins | MdeA | MF | chromosome | S. aureus, S. hemolyticus, B. cereus, B. subtilis | 192 |
| Type A streptogramins | Vga(A/B) | ABC | plasmid | S. aureus | 173 |
| Lincosamides, streptogramins | Lsa | ABC | chromosome | E. faecalis | 173, 186 |
| Clindamycin | Lsa(B) | ABC | plasmid | S. sciuri | 187 |
| Lincosamides | LmrB | MF | chromosome? | B. subtilis | 189, 190 |
| Lincosamides | LmrB | MF | chromosome | C. glutamicum | 191 |
| Erythromycin | Cme | MF | chromosome | C. difficile | 172 |
| Macrolides, lincosamides, type B streptogramins | ?[e] | ? | [f] | S. pyogenes | 188 |
| Macrolides | MacAB-TolC | ABC | chromosome | E. coli | 521 |
| Macrolides | MtrCDE | RND | chromosome | N. gonorrhoeae | 168, 197, 198 |
| Macrolides, lincosamides, ketolides | AcrAB-TolC, Mex[g]; RND pumps in several Gram-negative bacteria[h] | RND | chromosome | E. coli, E. aerogenes, P. aeruginosa; other Gram-negative bacteria | 74, 195, 196 |
| Erythromycin | MdfA[m] | MF | chromosome | E. coli | 74 |
| Erythromycin | ? | ? | ? | Campylobacter spp. | 202, 480 |

Figure 27 (Cont'd)

Table 1. (*continued*)

| Antimicrobial | Efflux system | Pump family | Gene location | Organism(s) | Reference[a] |
|---|---|---|---|---|---|
| Erythromycin, roxythromycin | MexCD-OprJ | RND | plasmid | *Pseudomonas* spp. | 201 |
| Tetracyclines & glycylcyclines | | | | | |
| Tetracyclines | Tet(A), Tet(B), Tet(C), Tet(D), Tet(E), Tet(G), Tet(H), Tet(J), Tet(Y), Tet(Z), Tet(30), Tet(39) | MF | Plasmid | Gram-negative bacteria | 47, 96, 522 |
| | Tet(K), Tet(L) | MF | plasmid | Gram-positive bacteria | 47, 522 |
| | Tet38 | MF | chromosome | *S. aureus* | 94 |
| | Tet(V) | MF | chromosome | *M. tuberculosis, M. fortuitum* | 95 |
| | Rv1258/Tap | MF | chromosome | *M. tuberculosis, M. fortuitum* | 129, 130 |
| | P55/Rv1410 | MF | chromosome | *M. tuberculosis, M. bovis* | 131 |
| | MdfA[m] | MF | chromosome | *E. coli* | 74 |
| | MexAB-OprM[i], several three-component pumps of the RND family | | | | 74 |
| Glycylcyclines | AcrAB-TolC, MexXY-OprM, MexAB-OprM, MexCD-OprJ | RND | chromosome | *P. mirabilis, E. coli, K. pneumoniae, M. morganii P. aeruginosa* | 460–464a |
| | MepA | MATE | chromosome | *S. aureus* | 464a |
| β-Lactams | | | | | |
| | AcrAB-TolC[j] | RND | chromosome | *H. influenzae* | 331 |
| | MexAB-OprM[k]; several three-component pumps of RND family[l] | RND | chromosome | *P. aeruginosa*; several Gram-negative bacteria | 74, 250 |
| | LmrA[m] | ABC | chromosome | *L. lactis* | 85 |
| Aminoglycosides | | | | | |
| | AcrAD-TolC | RND | chromosome | *E. coli* | 74, 523 |
| | BpeAB-OprB | RND | chromosome | *B. pseudomallei* | 292 |
| | AmrAB-OprA | RND | chromosome | *B. pseudomallei* | 524 |
| | MexXY-OprM | RND | chromosome | *P. aeruginosa* | 74, 306, 307 |
| | MexAB-OprM[n] | RND | chromosome | *P. aeruginosa* | 74 |
| | EmrE[n] | RND | chromosome | *P. aeruginosa* | 74 |
| | MdfA[m] | MF | chromosome | *E. coli* | 74 |
| | LmrA[m] | ABC | chromosome | *L. lactis* | 85 |
| Oxazolidinones | | | | | |
| | AcrAB-TolC, AcrEF-TolC | RND | chromosome | *E. coli* | 196 |

[a] Where efflux systems have been described in earlier review articles, these are highlighted here, otherwise original articles are cited.
[b] This multidrug efflux system was originally identified as the Cmr/CmlA chloramphenicol exporter.
[c] Mutant strains of *P. aeruginosa* overexpressing MexEF-OprN are readily selected *in vitro* using chloramphenicol.[78–80]
[d] Where tested, RND-type efflux systems that promote resistance to chloramphenicol also promote florfenicol resistance (e.g. AcrAB-TolC[75] and AcrEF-TolC[86] in *S. enterica* serovar Typhimurium).
[e] Efflux has been demonstrated although an efflux system has not been identified.
[f] The efflux gene(s) has not been identified though its mobility has been confirmed.
[g] Mutant strains of *P. aeruginosa* overexpressing MexCD-OprJ can be selected *in vitro* using erythromycin (Poole, unpublished results).
[h] Export of macrolides, lincosamides and streptogramins by three-component RND type multidrug efflux systems may explain the insusceptibility of many Gram-negative bacteria to these agents.
[i] Mutant strains of *P. aeruginosa* overproducing MexAB-OprM can be selected *in vitro* using tetracycline.[78,132,133]
[j] Associated with resistance to ampicillin in clinical strains.[331]
[k] Implicated in resistance to meropenem[322] and ticarcillin[323,324] in clinical isolates.
[l] While many RND type multidrug efflux systems accommodate β-lactams (see text), few are implicated as primary determinants of resistance, in laboratory or clinical isolates.
[m] Cloned gene promotes very modest increases in MICs to the indicated antimicrobial.
[n] Show a modest contribution to intrinsic aminoglycoside resistance but only seen in low ionic strength media.

Figure 27 (Cont'd)

Table 2. Efflux-mediated resistance to fluoroquinolones[a]

| Efflux system | Pump family | Antimicrobial[b] | Organism(s) | Reference |
|---|---|---|---|---|
| Gram-positive | | | | |
| NorA | MF | NOR, CIP | S. aureus | 209, 525 |
| NorB | MF | NOR, CIP, MOX, SPR | S. aureus | 94 |
| ?[c] | ? | NOR, CIP, MOX, GAT, SPR | S. aureus | 212 |
| PmrA | MF | NOR, CIP | S. pneumoniae | 209, 526 |
| ?[d] | ? | NOR, CIP, MOX | S. pneumoniae | 213 |
| EmeA | MF | NOR, CIP | E. faecalis | 235, 235a |
| Lde | MF | NOR, CIP | L. monocytogenes | 233 |
| EfrAB | ABC | NOR, CIP | E. faecalis | 352 |
| ?[e] | ? | FQ | B. anthracis | 237, 527 |
| Bmr | MF | FQ | B. subtilis | 209 |
| Blt | MF | FQ | B. subtilis | 209 |
| Bmr3 | MF | FQ | B. subtilis | 528 |
| MD1, MD2[f] | ABC | CIP | M. hominis | 240 |
| LfrA | MF | FQ (CIP, NOR?) | M. smegmatis | 242, 529 |
| EfpA | MF | CIP, NOR | M. smegmatis | 242 |
| Rv1634 | MF | FQ | M. tuberculosis | 129 |
| Rv1258c | MF | OFL | M. tuberculosis | 245 |
| Rv2686c-Rv2687c-Rv2688c[g] | ABC | FQ | M. tuberculosis | 243 |
| LmrA | ABC | CIP, OFL | L. lactis | 85 |
| Mmr | SMR | CIP, NOR | M. smegmatis | 242 |
| Gram-negative | | | | |
| AcrAB-TolC, AcrEF-TolC | RND | FQ | E. coli | 74 |
| MexAB-OprM, MexCD-OprJ, MexEF-OprN, MexXY-OprM[h] | RND | FQ | P. aeruginosa | 74, 250 |
| AcrAB-TolC | RND | FQ | Enterobacter spp. | 74, 258, 530 |
| AcrAB-TolC | RND | FQ | Klebsiella spp. | 74, 76, 263, 531 |
| AcrAB-TolC | RND | FQ | S. enterica (Typhimurium, Enteritidis) | 75, 270–272, 532 |
| AcrEF-TolC | RND | FQ | S. enterica serovar Typhimurium | 86 |
| SmeABC, SmeDEF | RND | FQ | S. maltophilia | 74, 277, 289, 533, 534 |
| CmeABC, CmeDEF | RND | FQ | C. jejuni | 74, 256, 257, 535 |
| SdeAB | RND | FQ | S. marcescens | 194, 276, 535a |
| SdeXY | RND | NOR | S. marcescens | 74 |
| MtrCDE | RND | FQ | N. gonorrhoeae | 210, 280 |
| CeoAB-OpcM | RND | FQ | B. cepacia (cenocepacia) | 82 |
| AcrAB | RND | CIP | P. mirabilis | 74 |
| AdeABC | RND | FQ | A. baumannii | 74 |
| VcaM | ABC | CIP, NOR | V. cholerae | 290 |
| Orf12-Orf11-Orf10 (plasmid)[i] | ABC | NAL, NOR | Pseudomonas spp. | 193 |
| MdfA | MF | FQ | E. coli | 210, 291 |
| ? | ? | FQ | A. salmonicida | 255 |
| ? | ? | FQ | C. freundii | 536, 537 |
| ? | ? | OFL | P. vulgaris | 538 |
| ? | ? | CIP, NOR | B. fragilis | 209, 539 |

[a]Excluding MATE family multidrug exporters.
[b]NOR, norfloxacin; CIP, ciprofloxacin; MOX, moxifloxacin; GAT, gatifloxacin; SPR, sparfloxacin; OFL, ofloxacin; NAL, nalidixic acid; FQ, fluoroquinolones
[c]Efflux-mediated resistance observed but the specific determinant has not been identified; not NorA.
[d]Efflux-mediated resistance observed but the specific determinant has not been identified; not PmrA.
[e]Efflux-mediated resistance observed but the specific determinant not identified.
[f]Cytoplasmic membrane-associated ABC type efflux system assembled from 2 subunits.
[g]Cytoplasmic membrane-associated ABC type efflux system assembled from 3 subunits.
[h]Accommodates fluoroquinolones although no reports of fluoroquinolones selecting for MexXY-overproducing mutants *in vitro* or *in vivo*.
[i]Encodes an ABC-MFP component of a probable ABC-MFP-OMF multidrug export system.

TRANSCRIPTION FACTOR DECOYS, COMPOSITIONS AND METHODS

A sequence listing text (.txt) file is submitted under 37 CFR. 1.821(c) and is hereby incorporated by reference in its entirely. The details of the file as required under 37 CFR. 1.52(e)(5) and 37 CFR 1.77(b)(5) are as follows: Name of file is Boxall_PBL_P001_US_Sequence_listing.txt; date of creation is Feb. 17, 2014; size is 10 KB.

FIELD OF THE INVENTION

The invention provides methods and compositions for identifying cis-regulatory sequences. The invention also relates to methods and compositions for specifically modulating cell phenotypes, such as prokaryotic phenotypes, by altering the association of transcription factors to cis-regulatory elements in vivo with a concomitant alteration in the pattern of gene expression.

BACKGROUND TO THE INVENTION

Gene expression is a major determinant of a cell's phenotype, and in turn, DNA-protein interactions largely determine the patterns of gene expression. Modification of gene expression so as to affect phenotype is a major aim of biology and medicine, be it in industrial microbes, experimental models, pathogens or to tackle human disease. In this context the cis-regulatory sequences within the genome, the DNA component of the transcriptional machinery, are attractive targets for intervention. In comparison to tackling the proteins, working with DNA is far easier: sequencing is highly automated and relatively inexpensive, and DNA can be easily manipulated and readily amplified or synthesized. DNA-based therapies have also emerged as an exciting new class of therapeutic agents. In comparison to traditional pharmaceuticals, natural products or small molecules, DNA is an attractive type of therapeutic agent as it can be:

- designed by a rational process, most simply by examination of sequence data;
- cheaply manufactured at scale, by chemical synthesis of oligonucleotides or biological replication;
- predicted to have low toxicity, as DNA is a 'natural' compound and does not, in and of itself, typically induce immunogenic responses, and specificity can be controlled by sequence of the DNA-based therapy;
- greatly reduce R&D expenditure, as all stages of conventional drug development (target identification, lead compound discovery, medicinal chemistry) are truncated.

The challenge then becomes how to identify the key cis-regulatory elements. The technologies and expertise that have developed in parallel with the genome sequencing projects, such as massively parallel gene expression analysis using DNA microarrays and the use of bioinformatics to annotate the genome databases, are not sufficient to either identify all of the cis-regulatory elements or ascribe function to those that are known. In 2003, the National Institutes of Health in the US launched the ENCODE project to catalogue 1% of the cis-regulatory elements in the human genome (Science (2004) 306: 636-640; Nature (2007) 447: 799-816) and to develop high-throughput technologies as discovery platforms. The procedures developed included use of chromatin immunoprecipitation, probing hypersensitivity sensitivity to in vivo digestion by DNaseI (with DNA microarrays, high-throughput quantitative PCR and genomic libraries) and the development of new algorithms for bioinformatical detection. While these techniques have the potential to greatly accelerate the rate of discovery of cis-regulatory elements, they will not necessarily lead to their functional characterization: the output of the project is a comprehensive catalogue of these elements. Even though, from such work, it is likely that the tissue-specificity of the majority of elements will be known, and their distance from a gene and classification according to what type of trans-acting factor binds to them, this will not be sufficient to determine what the biological function of the element actually is. A further drawback common to all of these procedures is that they rely on the genome of the organism being sequenced. Furthermore, the approach using hypersensitivity to DNaseI digestion has the extra disadvantage that it is specific for eukaryotic cells, as, in this context, DNaseI is a probe of chromatin structure, and no comparable structure exists in prokaryotes.

Further, as yet there is no means for rapidly screening a large number of sequences for potential cis-regulatory sequences.

SUMMARY OF THE INVENTION

The inventors addressed these problems in the art by providing new methods for identifying and characterising cis-regulatory sequences in both prokaryotic and eukaryotic organisms.

One way to identify and characterize the function of individual cis-regulatory elements is to use transcription factor decoys (TFDs). Decoy oligonucleotides are designed to mimic the binding sites of transcription factors and prevent the latter from binding to their cognate genomic targets, with a consequent modification of gene expression. As such they represent a simple and generic tool for manipulating the DNA-protein interactions that regulate specific genes and that consequently determine phenotypes. Their utility has been demonstrated primarily in eukaryotic systems, where a spur to their development was their potential to function as novel classes of therapeutic agents (Mann & Dzau (2000) J. Clin. Investigation 106: 1071-1075). To this end, decoy oligonucleotides have been used to demonstrate that transcription factor EF2 represses smooth muscle proliferation in rats (Morishita et al. (1995) Proc. Natl. Acad. Sci. USA 95: 5855-5859); to block STAT3-mediated proliferation of carcinomas (Leong et al. (2003) Proc. Natl. Acad. Sci. USA 100: 4138-4143); and to show that targeting of the cAMP response element can control cancer proliferation in vivo (Park et al. (1999) J. Biol. Chem. 274: 1573-1580).

However a system has not been developed to use TFDs, on a large scale, that is capable of querying every occurrence of a sequence within a genomic fragment or entire genome. As it stands, that would require the synthesis of very large numbers of decoy oligonucleotides and an onerous experimental programme involving their transfection and screening for phenotypic change.

The invention described here addresses this need by developing a plasmid-borne library based system capable of systematically testing large numbers of sequences to determine whether they act in the genome as cis-regulators and associate them with a specific phenotypic effect. We refer to this system herein as "n[snare]".

Furthermore, once the relevant cis-regulatory sequences have been found, those sequences can be used to create TFDs that can be used to modify gene expression and gain control over phenotype. For several reasons, though decoys were developed for use in mammalian cells, they are better suited to use in bacteria. Getting decoys to work in eukaryotes can be problematic as they can be rapidly degraded in serum and nuclear extracts (Chu & Orgel (1992) *Nucl. Acids. Res.* 20: 5857-5858), cellular uptake of the decoy and its transition across the nuclear membrane can be inefficient (Griesenbach et al. (2002) *Gene Therapy* 9: 1109-1115), and some treatments can trigger non-specific or toxic effects. Using decoys in prokaryotes should circumvent many of these problems and as such they might prove to be an effective tool for the rapid identification of cis-acting regulatory sequences, such as transcription factor binding sites controlling both specific genes and larger regulatory networks. A successful demonstration of the approach was the use of an AT-rich decoy to alter the expression of $CO_2$-responsive genes in *Cyanobacterium* (Onizuka et al. (2003) *FEBS Lett.* 542: 42-46). In that system, the complimentary oligonucleotides with modified backbones (containing phosphorothioate to slow degradation by nucleases) were annealed to form double stranded decoy oligonucleotides that incorporated previously identified binding sites for a transcription factor. These were added directly to the medium from where it efficiently entered the cells. That report is, however, the only example we know of in which this approach has been successfully attempted to modify a particular prokaryotic trait. Accordingly, there remains a need in the art to extend the decoy methodology into the field of prokaryotic transcription factors to thereby alter a broad range of prokaryotic phenotypes. In addition, there remains a need in the art for high-throughput methods for identifying cis-acting regulatory factors, whether in prokaryotic or eukaryotic systems. This patent disclosure provides solutions to the above-noted limitations and needs in the art.

In one particular aspect the invention provides new means for increasing susceptibility of cells, e.g. bacterial cells, to antibiotics.

Accordingly, in one aspect the invention provides use of a decoy polynucleotide in a method for modulating antibiotic resistance of a cell, the method comprising:
(a) providing a decoy polynucleotide comprising a binding site for a transcription factor (a decoy sequence); and
(b) introducing the polynucleotide into the cell, wherein the cell comprises a gene or genes operably linked to a cis-regulatory sequence comprising a binding site for the transcription factor;
wherein introduction of the polynucleotide reduces binding of the transcription factor to the cis-regulatory sequence in the cell and causes an alteration in expression of the operably linked gene or genes in the cell, thereby modulating antibiotic resistance of the cell.

The invention also provides:
a decoy polynucleotide comprising a binding site for a transcription factor, wherein the transcription factor is a regulator of expression of one or more antibiotic resistance genes in a prokaryote or eukaryote and wherein the binding site in the decoy polynucleotide is not operably linked to a gene.
a plasmid comprising one or more copies of a monomer sequence, wherein the monomer sequence comprises a snare sequence that comprises a transcription factor binding site, and wherein the binding site is not operably linked to a gene.
a plasmid library comprising two or more plasmids of the invention wherein the snare sequences in the library together comprise all or substantially all of the cis-regulatory sequence in the genomic DNA or in a fragment of the genomic DNA of a prokaryote or eukaryote;
a plasmid library comprising two or more plasmids of the invention wherein the snare sequence in each plasmid comprises a sequence of randomised nucleotides of length n nucleotides, wherein substantially all nucleotide sequences of length n nucleotides are represented in the library;
a method of preparing a plasmid comprising two or more copies of a monomer sequence, the method comprising:
(1) providing a circular oligonucleotide comprising:
  (i) a test sequence of interest; and
  (ii) a binding site for a primer suitable for use in rolling circle amplification;
wherein the monomer sequence comprises (i) and (ii);
(2) performing rolling circle amplification using the circular oligonucleotide as a template, thereby providing a polynucleotide comprising repeats of the monomer sequence; and
(3) cloning the polynucleotide into a plasmid vector;
a method for preparing a plasmid library from a sample of genomic DNA wherein each plasmid comprises one or more copies of a monomer sequence, and wherein each monomer sequence comprises a snare sequence that is derived from the genomic DNA; the method comprising:
(1) providing a sample of double stranded genomic DNA;
(2) fragmenting the genomic DNA;
(3) ligating an adaptor to each end of the DNA fragments from (2), wherein each adaptor comprises:
  (iii) a means for immobilisation of the DNA fragment;
  (iv) a recognition site for a first restriction enzyme that cuts at a distance from the recognition site; and
  (v) a recognition and cutting site for a second restriction enzyme;
(4) optionally removing unligated adaptor;
(5) digesting the fragment bearing the adaptors with the first restriction enzyme, thereby producing two adaptored fragments, wherein each adaptored fragment comprises:
  (vi) an adaptor; and
  (vii) a DNA fragment comprising: a shorter strand: and a longer strand, wherein the longer strand comprises the snare sequence;
(6) immobilising the adaptored fragments produced in (5);
(7) denaturing the fragments to provide single stranded fragments;
(8) recreating the recognition site for the second restriction enzyme by ligating a complementary oligonucleotide to the adaptor and digesting the adaptored fragment with the second restriction enzyme, thereby producing an adaptor-snare fragment comprising:
  (viii) an adaptor fragment; and
  (ix) a single stranded snare sequence; and
(9) releasing the adaptor-snare fragment produced in (8) from immobilisation; and
(10) cloning the adaptor-snare fragment into a plasmid vector;
a method for preparing a plasmid library wherein each plasmid comprises two or more copies of a monomer sequence, and wherein each monomer sequence comprises a sequence of randomised nucleotides of length n nucleotides, the method comprising:
(1) providing a circular oligonucleotide comprising:
  (i) a randomised sequence of length n nucleotides; and
  (ii) a binding site for a primer suitable for use in rolling circle amplification;

wherein the monomer sequence comprises (i) and (ii);
(2) performing rolling circle amplification using the circular oligonucleotide as a template, thereby providing a polynucleotide comprising repeats of the monomer sequence; and
(3) cloning the polynucleotide into a plasmid vector;
  a plasmid or plasmid library prepared according to a method of the invention;
  a cell comprising an exogeneous decoy polynucleotide, the polynucleotide comprising a binding site for a transcription factor (a decoy sequence) which is not operably linked to a gene; wherein the cell comprises a gene or genes operably linked to a cis-regulatory sequence comprising a binding site for the transcription factor; and wherein the decoy polynucleotide causes an alteration in antibiotic resistance of the cell.
  a host cell or cells comprising a plasmid or plasmid library of the invention;
  a method for identifying the boundaries of one or more protein binding site(s) in a protein-DNA complex, the method comprising:
    1. providing a protein-DNA complex;
    2. carrying out a digestion with
      a. an enzyme having non specific DNA nicking ability; and
      b. a 5'-3' exonuclease; and
    3. determining the position of the 5' deletions generated in each DNA strand in (2) relative to a known fixed point on the DNA strand;
  a method for identifying a cis-acting regulator of gene expression of a prokaryotic or eukaryotic gene comprising:
    1. providing a plasmid library of the invention;
    2. introducing the plasmid library into a host cell(s) wherein the host cell comprises the cis-regulatory sequence of interest operably linked to a gene or genes, the expression of which can be determined directly or indirectly; and
    3. determining directly or indirectly the expression of the gene (or genes) in the presence and absence of the plasmid library;
  a method for altering expression of a gene or genes in a prokaryotic cell, the method comprising:
(a) providing a polynucleotide comprising a binding site for a prokaryotic transcription factor wherein the binding site is not operably linked to a gene in the polynucleotide; and
(b) introducing the polynucleotide into the cell;
wherein the cell comprises the gene or genes operably linked to a cis-regulatory sequence which comprises the transcription binding site or which competes with the transcription factor binding site for binding of transcription factor;
and wherein:
(i) the polynucleotide comprises a plasmid or a plasmid library according to the invention;
(ii) the polynucleotide comprises more than one copy of the binding site;
(iii) the polynucleotide comprise multiple direct repeats of the binding site;
(iv) the polynucleotide comprises additional sequence to the binding site;
(v) the polynucleotide comprises at least one element of secondary structure;
(vi) the polynucleotide comprises circular double stranded DNA;
  a method for altering expression of a gene or genes in a prokaryotic or eukaryotic cell, the method comprising:

(a) providing a polynucleotide comprising a binding site for a prokaryotic or eukaryotic transcription factor wherein the binding site is not operably linked to a gene in the polynucleotide; and
(b) introducing the polynucleotide into the cell;
wherein the cell comprises the gene or genes operably linked to a cis-regulatory sequence which comprises the transcription binding site or which competes with the transcription factor binding site for binding of transcription factor;
and wherein the cis-regulatory sequence is one identified by the method of the invention;
  a method for altering expression of a gene or genes in a eukaryotic cell, the method comprising:
(a) providing a polynucleotide comprising a binding site for a eukaryotic transcription factor wherein the binding site is not operably linked to a gene in the polynucleotide; and
(b) introducing the polynucleotide into the cell;
wherein the cell comprises the gene or genes operably linked to a cis-regulatory sequence which comprises the transcription binding site or which competes with the transcription factor binding site for binding of transcription factor;
and wherein the polynucleotide comprises a plasmid or a plasmid library according to the invention;
  a cell prepared according to a method of the invention;
  a decoy polynucleotide for use in treating bacterial infection, wherein the polynucleotide comprises a binding site for a transcription factor and the binding site is not operably linked to a gene;
  use of a decoy polynucleotide for treating bacterial infection, wherein the polynucleotide comprises a binding site for a transcription factor and the binding site is not operably linked to a gene;
  use of a decoy polynucleotide for the manufacture of a medicament for treating bacterial infection, wherein the polynucleotide comprises a binding site for a transcription factor and the binding site is not operably linked to a gene.

Thus, in one embodiment of the invention of this patent disclosure, we provide a method which combines the decoy approach with a simple in vivo footprinting protocol to rapidly identify candidate cis-acting regulatory motifs. Functional validation of these sequences was achieved by incorporating them into dumbbell decoy oligonucleotides, whose circular format suppresses degradation by exo- and endo-nucleases [Ahn et al. (2003) *Biochemical Biophysical Res. Comm.* 310: 1048-1053.]), and by testing their effect on phenotype in vivo.

In another embodiment according to this invention, we demonstrate that, using decoy oligonucleotides identified via application of the footprinting method, that we can significantly alter the level of antibiotic production in streptomycetes.

In a further embodiment according to this invention, we demonstrate the ability to utilize prokaryotic decoys in a therapeutic approach whereby pathogenic bacteria which are resistant to vancomycin are rendered, once again, susceptible to the antibiotic in the therapeutic window.

Thus the inventors provide a generic screening system by means of which cis-acting regulatory elements are identified in any genome, and sequences derived from such elements identified in this fashion are utilized to alter selected phenotypes in a fashion analogous to that demonstrated according to that illustrated by additional embodiments of the invention.

The inventors have also adapted and extended the decoy oligonucleotide technique for use in prokaryotes and demonstrate the ability to increase antibiotic production.

Furthermore the inventors have demonstrates that decoy oligodeoxynucleotides may be utilized to advantage to overcome antibiotic resistance in treating pathogens.

Other embodiments, utilities and details of this invention may be appreciated by a review of the complete disclosure, including the specific examples provided herein and the claims appended to this disclosure, including equivalents thereof.

BRIEF DESCRIPTION OF THE FIGURES

FIG. 24. Shows the amplification product obtained (SEQ ID NO:28 and SEQ ID NO:29) using the primers in SEQ ID NOS: 24 & 25 and an appropriate vector substrate (Example 7.2).

FIG. 27. A copy of Tables 1 and 2 from Poole (2005) J. Antimicrobial Chemother. 56, 22-24 listing the efflux-mediated resistance to non-fluoroquinoline antibiotics and fluoroquinoline antibiotics respectively. Reference numbers in the right hand column refer to those given in the paper.

BRIEF DESCRIPTION OF THE SEQUENCES

Figure 1:
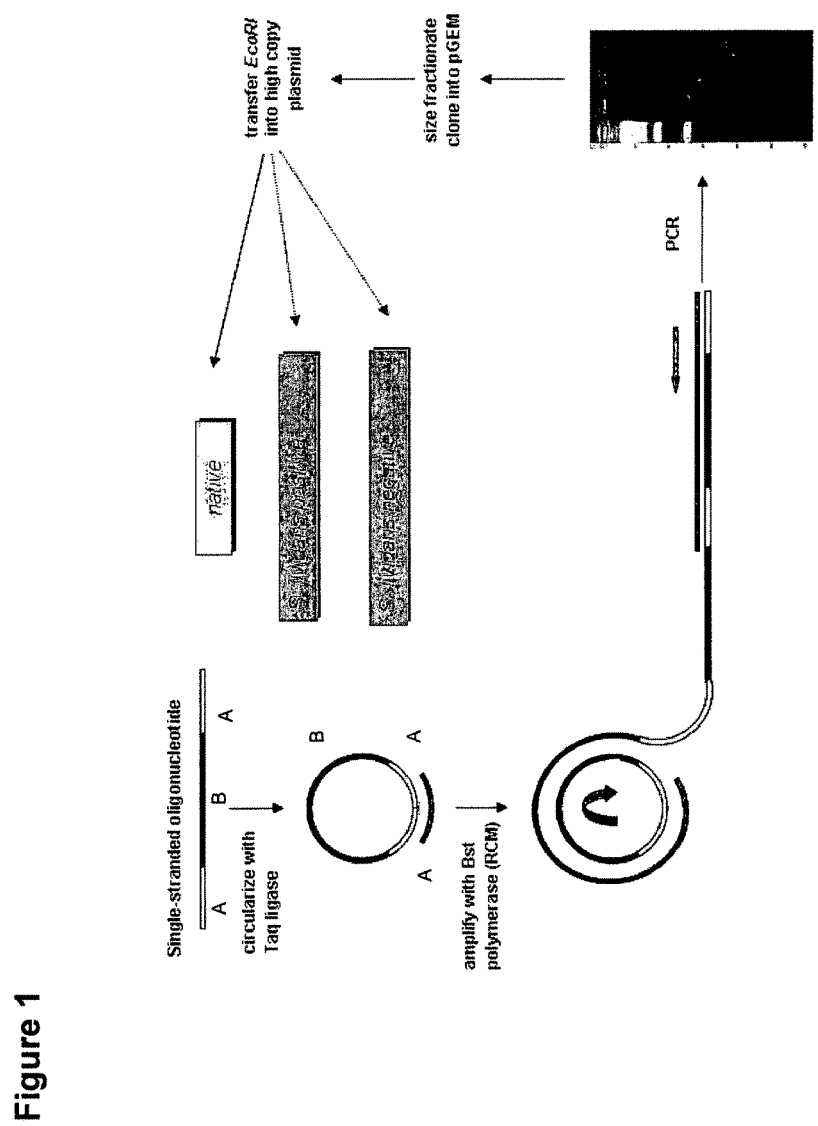
FIG. 1. Construction and testing of n[snare] plasmids. This protocol can also be used to produce 'generic' n[snare] libraries, made from random oligonucleotides, or species-specific libraries, from fragmented genomes.

SEQ ID NO: 1—a decoy oligonucleotide containing the AfsR binding site (Example 1).

SEQ ID NO: 2—a joining polynucleotide R-T7, which contains a partial complement of a commonly used primer, T7 (Example 1).

SEQ ID NO: 3—an oligonucleotide containing the AfsR binding site and use to create a cyclised decoy sequence in Example 1.

SEQ ID NOs: 4 & 5—sequences of each strand of a double stranded adaptor molecule (Example 2) SEQ ID NO: 6—a Bbv complementary oligonucleotide (Example 2).

SEQ ID NO: 7—an oligonucleotide comprising a NotI site and a randomised nucleotide sequence, where each randomised nucleotide is represented as "n" (Example 4).

SEQ ID NOs: 8-12—decoy oligonucleotides designed based on cis-regulatory sequences A24.1, A24.2, A24.3, A24.4 and A24.5 respectively (Example 5).

SEQ ID NO: 13—a decoy oligonucleotide designed based on a scrambled A24.5 sequence (Example 5).

SEQ ID NOs: 14-20—PCR primers used in quantitative PCR as in Example 5.

SEQ ID NO: 21—a vanH5 decoy oligonucleotide containing a binding site for phosphorylated VanR (Example 6).

SEQ ID NOS: 22 & 23—oligonucleotide primers used for amplification of a target sequence from the pGEMT-Easy vector as in Example 7.1.

SEQ ID NOS: 24 & 25—oligonucleotide primers used for amplification of a target sequence from the pGEMT-Easy vector in the production of dumbbell decoys as in Example 7.2.

SEQ ID NO: 26—the VAN decoy sequence used in Examples 8(a) and 8(b), and containing the regulatory element controlling induction of VanA type resistance in *E. faecium*.

DETAILED DESCRIPTION OF THE INVENTION

As described in more detail herein, the present inventors have devised methods and compositions for identifying, characterising and targeting cis-regulatory sequences in prokaryotes and eukaryotes.

A cis-regulatory sequence or element generally refers to a nucleotide sequence which occurs upstream (5') or downstream (3') of a gene or genes and which functions to modulate expression of the gene or genes. Typically, a cis-regulatory sequence comprises a binding site for a protein (transcription factor) which regulates transcription of the given gene(s). Binding of the protein to the sequence results directly or indirectly in modulation of expression of the gene(s). For example, the bound protein may interact with another protein bound to a nearby region which is needed for transcription and anchor the protein in the correct position, or may inhibit binding of another protein which is necessary for transcription. Typically the cis-regulatory sequence or element occurs in the promoter region of a gene, but it is not unusual in prokaryotes for cis-regulatory sequences to be positioned hundreds of base pairs upstream or downstream of the genes they affect. In eukaryotes, cis-regulatory sequences can act at great distances to influence expression of a gene, typically on the order of 1-2 kb, but it is not unknown for sequences to act over 100 kb to 1 Mb.

A cis-regulatory sequence may be repressive (inhibits or reduces transcription of the gene(s) when bound by a transcription factor) or activatory (activates or increases transcription of the gene(s) when bound by a transcription factor). Thus a transcription factor which binds a cis-regulatory sequence may be a negative effector (repressor protein) or a positive effector (activator).

The expression of certain genes will also be modified by indirect effects where, for example, the impact of a cis-regulatory sequence is on a separate gene which, in turn, influences the expression of the targeted gene. This may occur, for example, by causing changes to a regulatory network of which the targeted gene is a part, or due to a more global effect, such as a shock-response, which causes modification of the expression of the targeted gene.

Modulation of protein binding at cis-regulatory sequences can provide a useful means for modulating gene expression in a cell. One way of doing this is to provide a decoy nucleotide sequence. The decoy sequence comprises a transcription factor binding site which comprises of competes with the native or endogenous cis-regulatory sequence in the cell for binding to the cognate transcription factor. By reducing binding of the transcription factor to the native sequence, the decoy alters expression of the gene(s) whose expression is normally regulated by the cis-regulatory sequence in the cell. Such alteration can provide a useful alteration in phenotype, e.g. in metabolite production or antibiotic resistance of a prokaryotic cell. Decoy function as used herein refers to the capability of a sequence to compete with a cis-regulatory sequence for binding to a cognate transcription factor in this way.

The inventors have developed new means for identifying sequences which compete with cellular transcription factor binding sites for transcription factor binding, to alter cellular gene expression, and which may therefore provide new cis-regulatory sequences and decoy sequences.

n[Snare] Plasmids

The approach described herein is to make important adaptations of the known application in eukaryotes of the technology of 'decoy' oligonucleotides, which has been used to modulate expression in vivo. The logic of decoy oligonucleotides is simple and relevant to all biological systems: assert genetic control by perturbing the binding of transcription factors to their cognate sites. We improve on this technology by providing a generic and high-throughput tool for analysis of genetic regulation. A first modification involves making the approach plasmid-borne by developing a method to clone homopolymers of decoy sequences, to create high-copy 'n[snare]' plasmids. These are easily introduced into all bacteria and maintained by positive selection, circumventing the major deficiencies of the decoy approach, that the oligonucleotides can be difficult to introduce into the cell and can be sensitive to exonucleases, giving a relatively short half-life.

An overview of the molecular biology protocol used to create an n[snare] plasmid is given in FIG. 1. An overview of how the n[snare] plasmids affects gene regulation is given in FIG. 2. A demonstration of the efficacy of the n[snare] plasmid is given in FIG. 3 where it is used to ablate the production of antibiotic in *S. coelicolor* by the introduction of a known cis-regulatory sequence from a positive pleiotropic regulator of antibiotic synthesis, AfsR.

1. Design of n[Snare] Plasmids

The advantages of creating plasmid-borne versions of decoy oligonucleotides rather than decoys themselves for use in identifying the biological activity of cis-regulatory include:
 1. Cost of manufacture: The molecular biology protocol described below is simple and robust and can be applied either to synthesized oligonucleotides or fragments of DNA from diverse sources. As the plasmids self-replicate there is no need to produce large quantities of the plasmids. This compares favourably with a potential need to create substantial amounts of decoy oligonucleotides with potentially expensive modifications of the nucleotide backbone;
 2. Resistance to degradation: In comparison to decoys, plasmids show little susceptibility to in vivo degradation by nucleases;
 3. Plasmid concentration is maintained: As plasmids are self-replicating (and can have mechanisms to control their intracellular concentrations or copy number) and can be subjected to positive selection if necessary, the half life of an n[snare] plasmid is theoretically indefinite;
 4. Broad range of hosts: In Example 1a 'shuttle plasmid' is used which can be readily transformed and propagated in *E. coli* (for ease of genetic manipulation) and *S. coelicolor*. Many plasmids are known to those skilled in the art which allow transformation of a broad range of bacterial hosts;
 5. Combinations of cis-regulatory sequences can be tested using distinct n[snare] plasmids: Compatible plasmids can potentially be used to determine whether or not simultaneous treatment with two or more n[snare] plasmids have synergenistic effects.

In one aspect therefore the invention provides a plasmid which is suitable for testing possible decoy function of a known or putative cis-regulatory sequence, or for screening for new cis-regulatory sequences (which may act as decoy sequences). The plasmid is designated an n[snare] plasmid.

Figure 2:
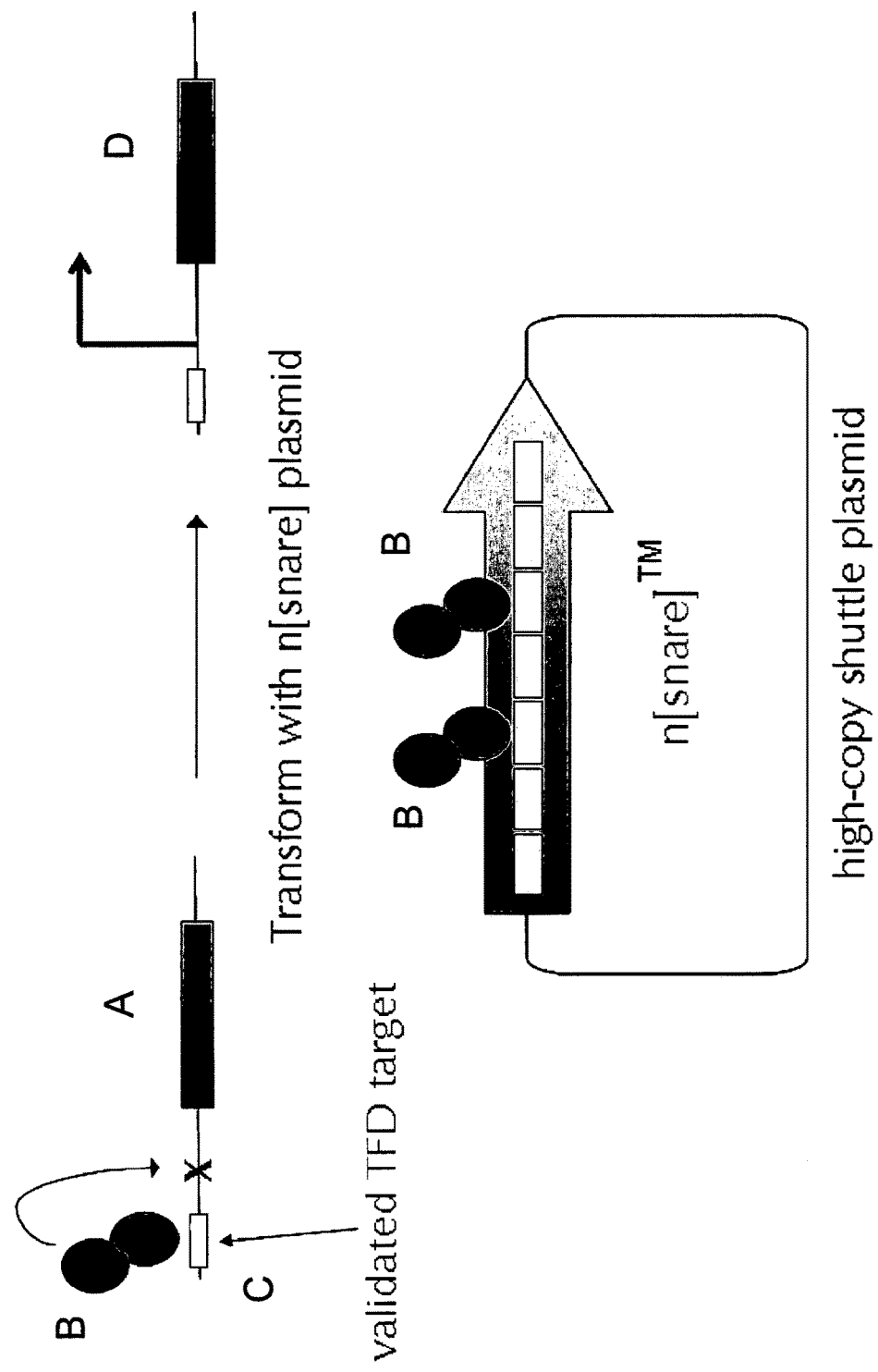
FIG. 2. Provides a graphic representation of how n[snare] plasmids can be used to affect gene expression. The n[snare] plasmid is introduced into the targeted cell (e.g. prokaryote), by standard means, and its stable propagation is ensured by selecting for its marker, usually a gene encoding resistance to an antibiotic. When thus introduced into a cell the n[snare] plasmid is able to affect expression of the targeted gene by titrating off the transcription factor "B" from the genomic promoter to relieve transcriptional repression of the downstream gene (shown as horizontal box "D", top right).

The principle of use of an n[snare] plasmid is illustrated in FIG. 2. The plasmid comprises a "snare" sequence (shown in multiple copies in the Figure). If the "snare" comprises a transcription factor binding site which competes with a cellular cis-regulatory sequence for binding to a transcription factor, introduction of the n[snare] plasmid to the cell will result in a titration of transcription factor off the cellular cis-regulatory sequence and onto the snare. This can be detected as a change in expression of a gene or gene(s) whose expression is regulated in the cell by that cis-regulatory sequence, or by alteration in the phenotype of the cell. A change in gene expression or phenotypic output thus indicates that the snare comprises a sequence with decoy function, and the plasmid can be used to identify or confirm the function of a cis-regulatory sequence.

In general an n[snare] plasmid comprises a plasmid vector and an insert sequence (the insert comprising the snare). Incorporating the snare sequence in a plasmid addresses the problems of decoy degradation in the art, and allows stable maintenance of the decoy (and any affect on gene expression) in the cell.

The insert sequence comprises one or more copies of a monomer sequence (which comprises the snare). Thus the insert may comprise (for example) from 1 to 200 monomer sequences. Typically there are two or more copies, for example, 2-200 copies, e.g. at least 10, 20, 30, 40, 50, 60, 70, 80, 90, 100, 110, 120, 130, 140, 150, 160, 170, 180, or 190 copies. For example, there may be 5-200, 5-150, 5-100, 10-150, 10-50, 5-50, 5-40, 10-40, 5-30 copies. For example, there may be 30 copies of the monomer sequence. The plasmid typically comprises a homopolymer of the monomer. Typically they are multiple copies of the monomer, for example, multiple direct repeats of the monomer sequence. Providing multiple copies of the monomer (and thus of the snare) increases the titrating power of the decoy.

The monomer sequence comprises the snare sequence. The snare comprises a nucleotide sequence which is to be tested for or used for cis-regulatory or decoy function as described herein.

For example, a snare may comprise a known or putative cis-regulatory sequence, a decoy sequence, a fragment of sequence to be tested for decoy function, e.g. a genomic fragment, such as a promoter fragment, or a randomised nucleotide sequence, or a combination of cis-regulatory sequences (e.g. 2, 3, 4 or more cis-regulatory sequences). n[snare] plasmid libraries may be prepared, comprising snare sequences derived from and covering, substantially all of the sequence (or cis-regulatory sequence) of a genome or genomic fragment. n[snare] plasmid libraries may also be prepared, in which the snare sequences comprise randomised nucleotide sequences of a given length ("n" nucleotides in length). Preferably all or substantially all possible sequences of length n are represented in the library. These libraries can be useful for screening to identify sequences that comprise and/or compete with cellular cis-regulatory sequence for transcription factor binding, and therefore to identify new cis-regulatory and decoy sequences.

Typically a transcription factor binding site in a snare is not operably linked to a gene, e.g. in the snare or snare plasmid. In that sense the binding site is isolated from its cognate gene or genes. A binding site in a snare may also be isolated from other elements in its cognate promoter. In one instance, the monomer sequence does not comprise a gene.

A monomer may comprise additional sequence in addition to the snare. Often such additional sequence derives from the method used to produce the snare and/or the plasmid insert. For example, a monomer may comprise an adaptor sequence, such as the adaptor sequence which typically results when "custom" snares are produced for a custom n[snare] library according to the methods herein. An adaptor sequence may comprise, for example, recognition and/or cutting sites for one or more restriction enzymes.

A monomer may comprise nucleotide sequence which provides a binding site for a primer, e.g. a primer used in production of the monomer or of an insert comprising multiple monomers.

For example, when a plasmid insert is prepared using a rolling circle amplification method as described herein, a monomer typically comprises a segment which corresponds to the binding site for the primer used in rolling circle replication, e.g. a T7 primer.

A monomer comprising a randomised snare sequence typically also comprises a region or regions of constant sequence. For example, a randomised snare sequence of n nucleotides may be flanked by regions of constant sequence. Alternatively, a central core of constant sequence may be flanked by regions of randomised nucleotide sequence.

The length of a monomer can be, for example, up to 1000 nucleotides, for example, up to 900, 800, 700, 600, 500, 400, 300, 200, 100, 90, 80, 70, 60, 50, 40, 30, 20, 15, or 10 nucleotides. Typically the length of the monomer is in the range of, for example 10-100, 10-50, 20-75, 30-60, 30-50, 35-55 such as 35-54 nucleotides. For example, the length of a monomer may be 30, 40 or 50 nucleotides.

A snare portion of a monomer may typically range in size from 10-30 nucleotides, for example, 10-25, 10-20, 15-20, such as 15, 16, 17, 18, 19 or 20, for example 19 nucleotides.

An adaptor sequence may comprise, for example, 5-30 nucleotides, for example, 5-25, 5-20, 5-15 or 5-10 nucleotides such as 10, 11, 12, 13, 14 or 15 nucleotides.

Typically, an insert in the n[snare] plasmid comprises one or more copies of a monomer as described herein. Where the insert comprise multiple repeats of a monomer, these may be tandem repeats.

An insert in the plasmid vector may comprise, for example about 1.5 kb, for example 1-2 kb, for example 1.1, 1.2, 1.3, 1.4, 1.5, 1.6, 1.7 or 1.8 kb. However, any suitable insert size, which allows stable maintenance of the plasmid in a suitable host cell and efficient use in the present methods may be used.

Typically the sequences of all monomers in a single plasmid are the same.

The plasmid vector for use in the n[snare] plasmid may be suitable for use in a prokaryotic or eukaryotic host. For example, the vector may be for use in a prokaryotic such as a bacterial, e.g. actinomycete host. For example, the plasmid vector may be suitable for use in a Streptomycete or E. coli strain, e.g. one or more of Streptomyces coelicolor e.g. A3(2) (or strain M145 or M600), E. coli, Streptomyces lividans or Streptomyces cinnamoneous. Suitable hosts are described further herein.

Typically, the vector is a broad host range and/or shuttle vector and can therefore be maintained and propagated in more than one host. The plasmid may a conjugative plasmid. This allows easy transfer from one cell to another by conjugation.

Preferably the plasmid is self-replicating. Typically the plasmid is a high copy number plasmid. For example, the plasmid may be maintained at, for example, 20-100 copies per cell, for example 20, 30, 40, 50, 60, 70, 80, 90 or 95 or 100 copies per cell. High copy number increases titrating power of a decoy sequence in the snare.

Typically an n[snare] plasmid comprises an origin of replication. Suitable origins are known in the art. Typically the plasmid additionally comprises one or more detectable marker genes, for example, one or more genes encoding antibiotic resistance, e.g. the aac gene encoding apramycin resistance. Expression of the marker gene(s) allows screening for maintenance of the plasmid in a host cell.

Examples of suitable plasmid vectors include, for example, pIJ86. Suitable vectors are known in the art.

A monomer or snare sequence may comprise a cis-regulatory sequence or decoy sequence described herein and/or identified according to the methods described herein.

For example, a transcription factor binding site in a plasmid may comprise or compete for transcription factor binding with, a cis-regulatory sequence which regulates expression of a gene or genes which have a role in metabolite production. The metabolite may be, e.g. an antibiotic, enzyme or pharmaceutical. An antibiotic may be, e.g. actinorhodin, undecylprodigiosin or cinnamycin.

For example, a snare may comprise a binding site for AfsR protein (a pleitropic regulator of antibiotic synthesis in *S. coelicolor*). An AfsrR binding site is shown in bold in SEQ ID NO: 1 (Example 1). A monomer may thus comprise SEQ ID NO:1. Thus a monomer may be the double stranded version of SEQ ID NO: 1 as in Example 1. In one example there may be 30 repeats of the monomer and/or the plasmid may comprise the shuttle vector pIJ86. Thus in one aspect, the invention relate to an n[snare] plasmid(s) prepared according to the method in Example 1.

In another example a snare may comprise a cis-regulatory sequence in the *S. coelicolor* actII-orf4 promoter, for example a repressor cis-regulatory sequence, or a sequence that competes with such a sequence for transcription factor binding, as described herein. For example a cis-regulatory sequence may comprise sequence A24.1, A24.2, A24.3, A24.4. or A24.5 identified herein. In one aspect a monomer may comprise one of SEQ ID NOs: 8-12 described herein or SEQ ID No: 13.

A transcription factor binding site in a plasmid may comprise, or compete for transcription factor binding with, a cis-regulatory sequence which regulates expression of a gene or genes which have a role in determining antibiotic resistance, such as any one or more of the genes listed herein.

For example, a snare may comprise a binding site for the VanR transcription factor, for example, a VanR binding site located in the vanH promoter of, for example, *Entercoccus faecium* or *S. coelicolor*, or a sequence which competes with such a site. An example of a 30 bp VanR binding site is shown (capitalised) in SEQ ID NO: 21 and a further example is provided in SEQ ID NO:26 which contains the VanR binding site for Enterococci. In one example a monomer may comprise SEQ ID NO: 21 or SEQ ID NO:26 or a variant thereof which competes for binding of VanR transcription factor with a native VanR binding site in a cell of interest. For example, a variant may comprise the native VanR binding site in another species or strain.

A transcription factor binding site in a plasmid may comprise, or compete for transcription factor binding with, a cis-regulatory sequence which regulates expression of a gene or genes which have a role in determining solvent tolerance, e.g. butanol tolerance.

A snare may comprise a sequence derived or isolated from a genome or genomic fragment. A genomic fragment may comprise a gene or genes encoding a particular function or phenotype of interest, e.g. production of a metabolite(s) such as an antibiotic (e.g. cinnamycin, actinorhodin, undecylprodigiosin), tolerance to a particular solvent(s) e.g. butanol, or toxin(s), resistance to a particular antibiotic(s), or any other function or phenotype of interest. A snare may comprise, for example, a sequence derived or isolated from the promoter region of such gene(s) or surrounding sequences, e.g. sequence at a greater distance from a gene(s) than the promoter, e.g. at up to 200 bp or more.

A snare may comprise a sequence that competes with such a sequence for transcription factor binding, as described herein. For example, a snare may comprise a cis-regulatory sequence or decoy sequence derived from a fragment of the *S. cinnamoneus* genome comprising the cinnamycin biosynthetic cluster of genes. Methods for preparing such snares are described herein. A snare may comprise a cis-regulatory sequence from the *S. cinnamoneus* cin7 promoter or a sequence that competes with such a sequence for transcription factor binding, as described herein.

A snare may comprise sequence derived or isolated from the genome or a genomic fragment of a prokaryote which displays solvent tolerance, e.g. *E. coli* K12, which has butanol tolerance. In particular, a snare may comprise a cis-regulatory sequence derived from the promoter of a gene encoding solvent tolerance or whose expression is associated with solvent tolerance, or a sequence which competes with such a cis-regulatory sequence for transcription factor binding. Methods for preparing such snares are described herein.

A snare may comprise a sequence (e.g. a cis-regulatory sequence or decoy sequence) derived from or isolated from the genome or a genomic fragment of a prokaryote which displays antibiotic resistance (typically the fragment comprises the gene(s) encoding resistance). The genomic fragment may comprise a gene or gene(s) encoding antibiotic resistance. A snare may comprise a cis-regulatory sequence from the promoter of a gene(s) encoding antibiotic resistance, or a decoy sequence which competes with such a sequence for transcription factor binding. Any antibiotic resistance of interest may be targeted. For example, antibiotic resistance to: the class of antibiotics known as aminoglycosides (such as kanamycin and gentamycin); the glycopeptides (such as vancomycin); the beta-lactams which include the penicillins (such as ampicillin, carbenicillin and penicillin), the beta-lactamase inhibitors and combinations of (such as piperacillin and tazobactam), the cephalosporins (such as cefepime), the carbapenems (such as meropenem), the monobactams (such as Aztreonam); the polypeptide antibiotics (such as polymixcin B); the quinolines (such a levaquin); the fluoroquinolines (such as ciprofloxacin); the sulfonamides (such as Bactrim); the tetracyclines (such as tetracycline); the macrolides and ketolides (such as azithromycin); the oxazolidinones (such as linezolid); the nitroimidazoles (such as metronidazole); the nitrofurans (such as nitrofurantoin); the streptogramins (such as dalfopritsin); the cyclic lipopeptides (such as daptomycin); the lincosamides (such as clindamycin) and variously, chloramphenicol, rifampicin, isoniazid, ethambutol, telvancin, teicoplanin, oritavancin, dalbvancin, trimethoprim/sulfamethoxazole, fosfomycin, nitrofurantoin and tigecycline and Zyvox.

For example, antibiotic resistance to: the class of antibiotics known as aminoglycosides (such a kanamycin); the carbapenems (such as meropenem); the cephalosporins (such as cefepime); the glycopeptides (such as vancomycin); the penicillins such an ampicillin, carbenicillin and penicillin); the polypeptide antibiotics (such as polymixcin B); the quinolines (such a levaquin); the sulfonamides (such a Bactrim); the tetracyclines (such as tetracycline); and variously, chloramphenicol, rifampicin, Zyvox, and daptomycin.

n[Snare] Plasmid Libraries

Having described the creation of n[snare] plasmids capable of establishing functional activity of single cis-regulatory elements, we here generalize the methods by which these sequences may be discovered and characterized, including via a method using libraries of n[snare] plasmids, a methodology compatible with high-throughput screening.

The overall aim of this methodology is to develop a new method to rapidly identify cis-acting regulators of prokaryotic as well as eukaryotic genes, and in doing so create tools capable of modifying expression in vivo. The method allows for dissection of large scale regulatory networks. The anticipated advances in our understanding of the mechanics of genetic regulation will parallel the breakthrough afforded by microarray transcriptomic analysis.

This work identifies genetic modifiers and determines pathways in a different way to existing technologies such as creation of gene knock-outs or insertional mutagenesis. Those approaches generally identify trans-acting regulators (such as the transcription factors). By identifying cis-acting factors, this technology circumvents problems associated with these traditional approaches: redundancy—due to the inherent complexity of transcriptional regulation, meaning that more than one transcription factor can bind at the same site; polar effects—mutagenesis may affect the expression of genes located 3' of the site of mutation in the same transcription unit; high cost and turnaround time—generating and validating a single knock-out may take many weeks to years (depending on the species) and performing saturation mutagenesis is a lengthy and expensive procedure; species-specificity—the approach described herein has potential utility in all experimental systems, and it is anticipated that a universal 'decoy' library can be applied to map regulation in the majority of species.

In Example 1 we demonstrate a substantial improvement on decoy technology, reporting a modification making the approach plasmid-borne by developing a method to clone homopolymers of decoy sequences, to create high-copy 'n[snare]' plasmids. These are easily introduced into many bacterial species and maintained by positive selection, circumventing the major deficiencies of the decoy approach, that the oligonucleotides can be difficult to introduce into the cell and can be sensitive to exonucleases, giving a relatively short half-life. In a second modification and improvement we create n[snare] libraries, consisting of either fragments of the entire genome, detailed in Example 2, or sequences derived from randomized oligonucleotides, described in Example 4. These approaches allow comprehensive collection of regulatory elements to be screened in parallel, which is a far more powerful approach than use of decoys for screening purposes, which is limited to sequential testing of defined sequences. Below, in Example 3 a reporter system, using regulation of antibiotic production as a model, is used in one exemplary embodiment to select for positive and negative regulators within the library.

Figure 4:
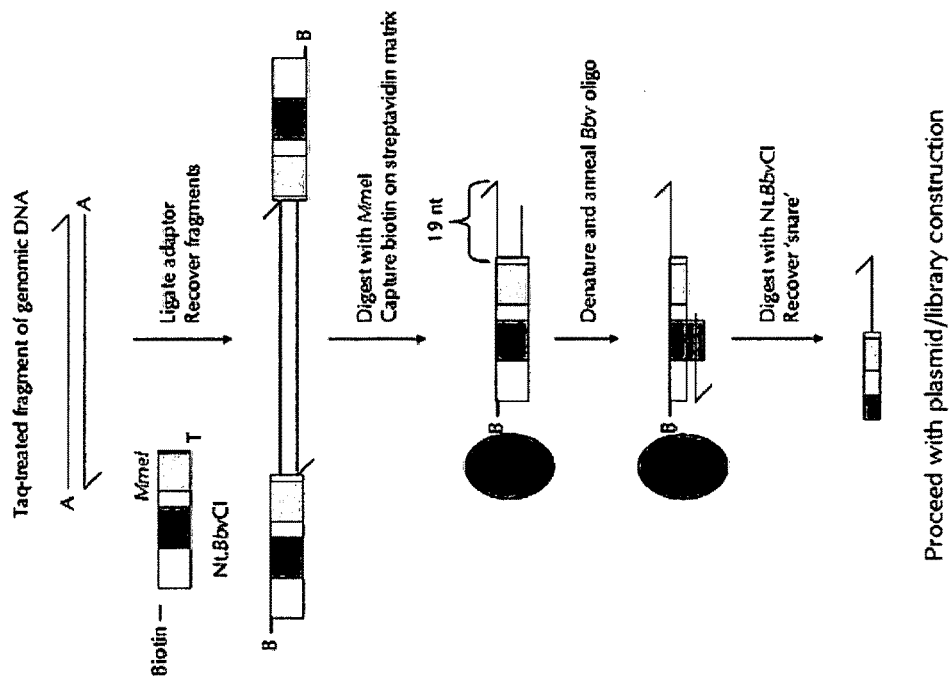
FIG. 4. Part of the process for creating custom n[snare] plasmid libraries: Converting genomic fragments to short single stranded nucleotides. n[snare] plasmid libraries are created from large pieces of DNA in such a fashion that every cis-regulatory sequence within that DNA should be represented in the library.

FIG. 4 is a schematic showing part of the process of how custom n[snare] plasmid libraries are constructed.

Figure 5:
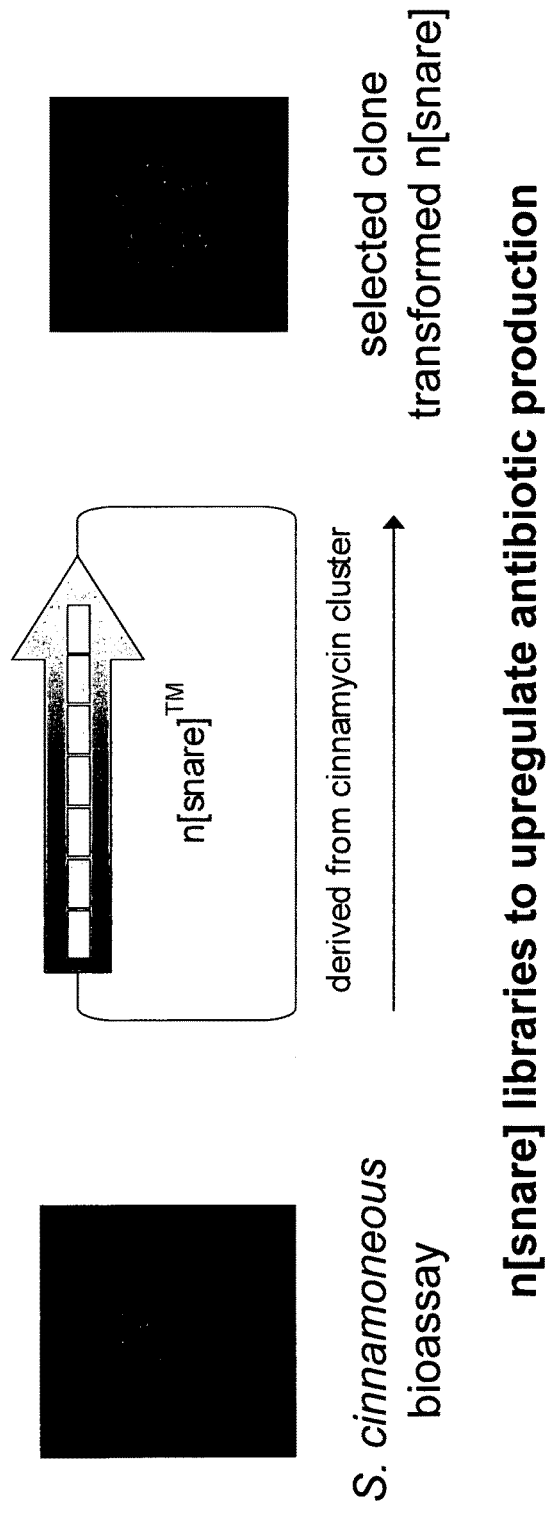
FIG. 5. n[snare] plasmid libraries can be used to gain control of targeted phenotypes, such as antibiotic production. Following introduction of members of the library by conjugation, clones are selected on the basis of increased production of cinnamycin (right).

FIG. 5 shows an experimental approach using an n[snare] library to detect cis-regulatory elements capable of upregulating production of the antibiotic cinnamycin from *Streptomyces cinnamoneous*.

Figure 6:
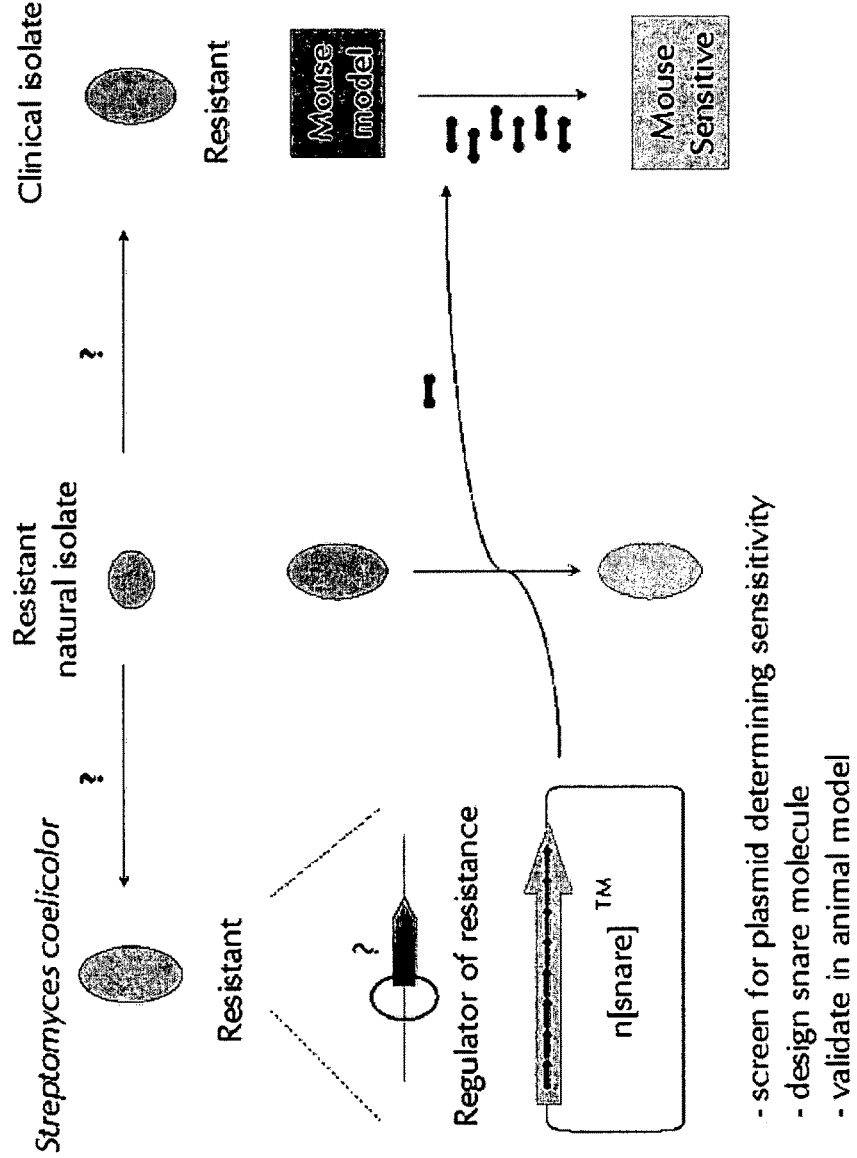
FIG. 6. Further details for application of n[snare] to combating antibiotic resistance. The schematic in this figure shows how a library of n[snare] plasmids is used to identify cis-regulatory sequences controlling antibiotic resistance when nothing is known about the genetic pathway of the mechanism.

FIG. 6 provides further details for application of n[snare] to combating antibiotic resistance.

n[Snare] Plasmid Libraries as Discovery Tools

Gene expression, and concomitantly phenotypic effect, are largely controlled by DNA-protein interactions. Efforts to understand and control gene expression generally place more stress on manipulating the protein component of the transcriptional machinery, the trans-acting factors such as transcription factors, rather than the DNA sequences (the cis-regulatory elements), that they bind to. Targeting the cis-regulatory elements, as opposed to the trans-acting factors, has the following advantages: it is easier to transfect oligonucleotides into cells than to make genetic deletions of targeted proteins; use of oligonucleotides is more adaptable to high-throughput analysis; use of cis-acting elements circumvents the problem of redundancy in regulatory networks, where deletion of one particular transcription factor is compensated for by the activity of another binding to the same cis-regulatory sequence. A potential bottleneck with the decoy approach, however, is the identification of candidate sequences.

For this purpose the utility of n[snare] vectors is demonstrated by creating libraries from a genomic fragment and testing to see whether members of the resulting library can exert control of the product synthesized by the genes contained on that fragment. In addition, the molecular biology of library creation is tested; to confirm that the libraries are sufficiently complex and have the expected molecular structure of direct repeats of the same sequence. These successes are developed further to create a powerful screening method with broad and generic applications.

As described above therefore, the invention also relates to n[snare] plasmid libraries. The plasmid libraries may be used according to the methods of the invention to screen for new cis-regulatory sequences and decoy sequences in either prokaryotes or eukaryotes. Use of n[snare] libraries for screening allows high throughput screening of multiple sequences for decoy function.

The snare sequences of the plasmids in the library may be derived from a genomic fragment or a genomic DNA. The library may then comprise snare sequences representing or covering substantially all of the genomic fragment or genome sequence. This type of plasmid library is referred to herein as a custom n[snare] library. Alternatively, the snare sequences of the plasmids in the library may comprise a randomised sequence of length "n" nucleotides. The library may then comprise substantially every possible nucleotide sequence of length "n" as described herein. Such a library is described herein as a universal n[snare] library.

Custom n[Snare] Plasmid Libraries

Typically the snares are derived from a genomic fragment or genomic DNA (prokaryotic or eukaryotic). For example, the genome or a genomic fragment of a prokaryote such as a bacterium, e.g Streptomycetes, such as *S. cinnamoneus, S. lividans* or *S. coelicolor*, or *E. coli*.

The genome or genomic fragment from which the library is derived may comprise a gene or genes encoding a particular function or phenotype of interest, e.g. production of a metabolite(s) such as an antibiotic (e.g. cinnamycin, actinorhodin, undecylprodigiosin), tolerance to a particular solvent(s) or toxin(s), resistance to a particular antibiotic(s), or any other function or phenotype of interest. The snares may comprise sequence derived or isolated from the promoter region of such gene(s). Suitable genes and functions/phenotypes have been described above in relation to snare sequences.

Thus the genomic DNA or fragment may comprises a gene or genes which have a role in metabolite production, e.g. where the metabolite is an antibiotic, enzyme or pharmaceutical, or a gene or genes which have a role in determining antibiotic resistance or a gene or genes which have a role in determining solvent tolerance.

A genomic fragment which comprises a gene or genes encoding a particular function or phenotype may have been identified by detecting horizontal transfer of the genes encoding the function or phenotype into a heterologous cell.

A genomic fragment which comprises a gene or genes encoding a particular function or phenotype may have been identified by bioinformatical analysis. Alternatively it may have been identified by a functional screen of a collection of such fragments.

Methods for preparing custom n[snare] libraries are described herein.

Universal Libraries

In a universal library, a snare typically comprises a randomised nucleotide sequence of n nucleotides in length. The library may comprise snares representing all or substantially all permutations of sequences of n nucleotides in length. In general n may range from 5-50, for example 10-50, for example 20-40 e.g. 25-35 e.g. 6, 7, 8, 9, 10, 11, 12, 13, 14, 15, 16, 17, 18, 19 or 20 nucleotides.

A monomer in such a library may additionally comprise constant sequence. Thus the randomised sequence (variable region) may be flanked by a constant region on one or both sides. Alternatively, the monomer may comprise a defined core sequence flanked by variable regions. A nucleotide bias may be introduced in the variable region. For example, the variable region may comprise a higher GC bias where this is appropriate, e.g. where the library is for use in screening for cis-regulatory sequences in an organism in which the DNA displays a high GC bias.

In one example, the snare comprises a randomised nine nucleotide sequence (n=9). The monomer in the n[snare] plasmids may comprise the oligonucleotide sequence of SEQ ID NO: 7. Methods for producing a universal n[snare] library are described herein.

Methods for Preparing n[Snare] Plasmids

In general, an n[snare] plasmid as described herein may be prepared by a method comprising:
  providing a polynucleotide comprising one or more copies of a monomer sequence; and
  cloning the polynucleotide into a suitable plasmid vector.

The composition of the monomer is as described herein for the n[snare] plasmid. Suitable plasmid vectors have also been described.

The polynucleotide comprising one or more copies of a monomer sequence may be provided by a method comprising:
(1) providing a circular oligonucleotide comprising:
  (i) a test sequence of interest (B in FIG. 1); and
  (ii) a binding site for a primer suitable for use in rolling circle amplification (A in FIG. 1);
wherein the monomer sequence comprises (i) and (ii); and
(2) performing rolling circle amplification using the circular oligonucleotide as a template, thereby providing a polynucleotide comprising repeats of the monomer sequence.

Step (1) of the method may further comprise amplifying the rolling circle amplification products by PCR and isolating polynucleotide fragments of the required size, for example, fragments comprising 30-50 repeats of the monomer sequence. This can be done by, e.g PAGE analysis.

A circular oligonucleotide may be prepared by a method comprising:
providing a linear single stranded oligonucleotide comprising: the test sequence of interest (i) and the binding site for a primer suitable for use in rolling circle amplification (ii);
circularising the oligonucleotide, e.g. using Taq ligase, typically in the presence of a universal joining oligonucleotide;
optionally digesting remaining linear DNA with an exonuclease; and
recovering monomeric circular oligonucleotides, e.g. using PAGE.

Primers suitable for use in rolling circle amplification are known in the art. For example, a T7 primer may be used.

Methods for carrying out rolling circle amplification are known in the art. For example, BstI polymerase may be used.

In one example, PCR amplification of the rolling circle amplification products is carried out using the same primer that was used for rolling circle amplification, e.g. T7 primer.

In general the test sequence (i) in the monomer comprises a snare sequence as described herein.

As described herein, snare sequences may be isolated from genomic DNA, e.g. from an entire genome, or from a genomic fragment. A snare sequence, once isolated, may be used to form a n[snare] plasmid by the method above. Thus a library of n[snare] plasmids derived from a genome or genomic fragment (a custom library as described herein), may be prepared.

A protocol for preparation of snare sequences from a genome or genomic fragment is illustrated in FIG. 4. Typically a method comprises:
(1) providing a sample of double stranded genomic DNA;
(2) fragmenting the genomic DNA;
(3) ligating an adaptor to each end of the DNA fragments from (b), wherein each adaptor comprises:
  (iii) a means for immobilisation of the DNA fragment;
  (iv) a recognition site for a first restriction enzyme that cuts at a distance from (e.g. downstream (3') of) the recognition site; and
  (v) a recognition and cutting site for a second enzyme;
(4) optionally removing unligated adaptor;
(5) digesting the fragment bearing the adaptors with the first restriction enzyme, thereby producing two adaptored fragments, wherein each adaptored fragment comprises:
  (vi) an adaptor; and
  (vii) a DNA fragment comprising: a shorter strand: and a longer strand (e.g. with a 3' overhang), wherein the longer strand comprises the snare sequence;
(6) immobilising the adaptored fragments produced in (5);
(7) denaturing the fragments to provide single stranded fragments;
(8) recreating the recognition site for the second restriction enzyme by ligating a complementary oligonucleotide to the adaptor and digesting the adaptored fragment with the second restriction enzyme, thereby producing an adaptor-snare fragment comprising:
  (viii) an adaptor fragment; and
  (ix) a single stranded snare sequence; and
(9) releasing the adaptor-snare fragment from immobilisation.

The adaptor-snare fragment produced in (8) comprises the single stranded snare sequence and a fragment of the adaptor that remains after digestion with the second restriction enzyme (corresponding to the portion of the adaptor between the recognition site for the second enzyme and the end of the adaptor that is linked to the snare). The monomer in the eventual n[snare] plasmid (and the test sequence (i) above) will comprise the adaptor-snare fragment.

The genomic DNA sample may be derived from a prokaryotic or eukaryotic cell. The genomic DNA sample may comprise a genomic fragment or an entire genome. The sample may be from a cell which displays a particular phenotype of interest, e.g. production of a particular metabolite, resistance to a particular antibiotic, such as a native strain (e.g. a pathogen) or clinical isolate. For example, the sample may be from *S. cinnamoneus* which produces cinnamycin, from *S. coelicolor* which produces actinorhodin, undecylprodigiosin, from *E. coli* K12 which displays tolerance to butanol, or from *Enterococcus faecium* or *S. coelicolor* which display resistance to vancomycin. The sample may be from a bacterial model, e.g. which has acquired a particular phenotype or function by horizontal gene transfer.

Typically the fragments produced in step (2) are about 500 bp in length, but may range for example, from 100-1000 bp, such as 200-900, 300-800, 400-600 bp, such as 150, 250, 350, 450, 550, 650, 750, 850, 950 bp. Any suitable fragmentation method may be used to produce the fragments. Preferably the method produces randomised or unbiased fragments. For example, sonication may be used.

Fragments produced in step (2) may comprise different types of ends—for example, blunt ends, or 5' or 3' overhangs of different lengths. Therefore, the fragments produced in fragmentation step (k) may be further treated to produce a population of fragments that are homogeneous in that each fragment has the same 3' dNTP overhang—dA or dT. This may be done, for example, by treating with Taq polymerase and suitable dNTPs to repair fragment ends if necessary, and add a 3' dNTP e.g. dA overhang.

Adaptors may be attached to the fragments by any suitable means. For example, an adaptor may comprise a 5' dNTP overhang that is complementary to the 3' dNTP overhang of each of the fragments. Thus, for example, if the fragments produced in step (b) comprise a 3' dA overhang, an adaptor may comprise a 5' dT overhang.

In the method set out above, the adaptors comprise a means for immobilising the DNA fragment. Immobilisation is not essential to the present method but has the advantage that it reduces experimental background. An adaptor may comprise any suitable means for immobilising the fragments. For example, an adaptor may comprise (typically at the end distal to the DNA fragment) one member of a pair of binding molecules, wherein the binding molecules in the pair bind each other, and wherein the other member of the pair may be comprised in a suitable immobilisation matrix. For example, the binding molecules in the pair may be biotin and streptavidin. Biotinylated adaptors may be used, and the adaptored fragment captured on a streptavidin matrix.

The first restriction enzyme cuts at a distance from its recognition site. For example, the enzyme may cut downstream (3') of its recognition site. The distance at which it cuts determines the length of the snare sequence. Suitable lengths for the snare sequence are described herein. Examples of enzymes which may be used are MmeI. Other examples include GsuI, BpmI and isochizomers thereof. Further examples include members of the family of restriction enzymes known as type IIs that cut outside their recognition site to one side. In the current description those enzymes that cut on the 3' side are used and those which cut at greatest distance preferred, typically 15-25 nt (reviewed in *Gene* (1991) 100; 13-26). The nature of the double stranded cut introduced is not crucial but in the methods described here a 3' overhang is used. The method could be adapted to use both a 5' overhang and a blunt cut. The nature of the snare could be altered accordingly. For example, if an enzyme was used which gave an asymmetric product with a longer 5' overhang, it would be advantageous to turn the 5' overhang into the snare. Also depending on how the recognition site (which is typically asymmetric) is positioned in the adaptor enzymes could be used that introduced cuts 5' of its recognition site.

The second restriction enzyme cuts in the adaptor sequence. Examples of enzymes that can be used include Nt.Bbv.CI. This is known as a nicking endonuclease and is used in this application as it introduces a single stranded nick in the top strand to allow the recovery of the snare. However the method can be adapted to use the majority of commonly available restriction enzymes. Examples of enzymes that could be used include those that generate 3' or 5' overhangs or generate a blunt-ended break.

Once prepared, an n[snare] plasmid library can be tested for bias in its construction. Typically this is done by isolating the plasmids, digesting to release the insert, and further digesting (e.g. with the first restriction enzyme) to isolate the monomer sequences.

Creation of custom n[snare] plasmid libraries is described in the present Examples. A library is prepared from an *S. cinnamoneous* cinnamycin biosynthetic gene cluster in Example 2, and a library is prepared from *E. coli* K12 genomic DNA in Example 4. The invention relates to the libraries as prepared in these Examples.

As described herein, a snare sequence may comprise randomised nucleotide sequence. Typically the snare comprises a randomised (or variable) nucleotide sequence of "n" nucleotides in length. In general n may range from 5-50, for example 10-50, for example 20-40 e.g. 25-35 e.g. 6, 7, 8, 9, 10, 11, 12, 13, 14, 15, 16, 17, 18, 19 or 20 nucleotides. A library of plasmids may be prepared in which the snares comprise randomised sequence of length n. Such a library is a universal n[snare] library.

An oligonucleotide comprising the randomised sequence (and optionally constant sequence as described) may be synthesised using methods known in the art. Typically, in preparing snares for an n[snare] universal library, oligonucleotides comprising all or substantially all possible nucleotide sequences of length n are prepared.

A nucleotide bias may be introduced into randomised (or variable) region of the oligonucleotide. For example a GC bias may be introduced if appropriate.

The monomer or test sequence of interest (B in FIG. 1) in the method above may comprise an oligonucleotide prepared in this way. An n[snare] plasmid may then be prepared as described.

Example 4 describes preparation of a universal n[snare] library in which n=9. The invention relates to the library prepared according to the method in Example 4.

In one aspect the invention relates to an n[snare] plasmid which comprises a monomer and/or snare comprising a cis-regulatory sequence or decoy sequence described herein and/or identified according to the methods described herein, including any of the n[snare] plasmids or plasmid libraries described herein and/or prepared according to the methods herein, including the Examples.

Host Cells

The invention also relates to a host cell or cells comprising an n[snare] plasmid or plasmid library as described herein. The invention further relates to a host cell or cells comprising a decoy polynucleotide (decoy molecule) as described herein. In particular, the invention relates to such a host cell(s) which displays altered gene expression and/or phenotype, due to the presence of the plasmid, or decoy polynucleotide, e.g. increased production of a metabolite or fermentation product such as an antibiotic or enzyme, increased resistance to a solvent, increased sensitivity to one or more antibiotics, compared to the cell in the absence of the plasmid/decoy molecule.

Typically, the plasmid or plasmid library or polynucleotide has been introduced to the cell(s) by a suitable means, for example, transformation, transfection or conjugation.

A host cell for use in the present methods may be prokaryotic or eukaryotic. For example, a prokaryote such as a bacterial cell may be used. A host may be for example, an actinomycete such as a *streptomyces* species, e.g. *S. coelicolor*, for example *S. coelicolor* A3 (2), (strain M145 or M600), *S. lividans*, *S. cinnamoneous*, or *E. coli*. Other examples may include other species of gram positive bacteria, such as those from the group Actinobacteria, for example, bacteria from the genus *Mycobacterium*, such as the pathogenic bacteria *Mycobacterium tuberculosis, M. bovis, M. africanum*, and *M. microti; M. leprae*. A further example of a genus of gram positive bacteria is *Clostridium*, which includes pathogenic bacteria such as *Clostridium difficile* (a human pathogen), *C. botulinum, C. perfingens* and *C. tetani*, as well as bacteria of potential industrial use such as *C. acetylbutylictum, C. thermocellum* and *C. ljungdahlii*. Other genera of gram positive bacteria may include *Bacillus, Listeria, Staphylococcus, Clostridium, Corynebacterium, Streptococcus*, and *Enterococcus*. Host cells may also be gram negative bacteria, which includes the genera Enterobacteriaceae which includes human pathogens, such as *Salmonella* and *Escherichia coli*. Other examples of genera of gram negative bacteria may include *Pseudomonas, Bordetella, Borrelia, Brucella, Campylobacter, Francisella, Haemophillus, Klebsiella, Neisseria, Proteobacteria, Rickettsia, Vibrio, Yersina Moraxella, Helicobacter, Stenotrophomonas, Bdellovibrio*, acetic acid bacteria, *Legionella*, the cyanobacteria, spirochaetes, green sulfur and green nonsulfur bacteria and many others. Important gram negative pathogens include the cocci species which cause a sexually transmitted disease (*Neisseria gonorrhoeae*), a meningitis (*Neisseria meningitidis*), and respiratory symptoms (*Moraxella catarrhalis*). Other Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Host cells could also include eukaryotes such as yeasts (examples of which may include: those used for industrial production such as the genera *Saccharomyces* (such as *S. cerevisiae*), *Schizosacharromyces* (*S. pombe*) and the methyltrophic yeast genera *Pichia* [such as *P. pastoris*] and *Candida*, also *Hansenula polymorpha*; pathogenic yeasts such as the *Candida* genera [such as *C. albicans* and *C. tropicalis*], also the *Cryptococci* genera [such as *C. neoformans*), fungi (which may include: pathogenic fungi such as the genera *Candida, Aspergillus* [such as *A. fumigatus* and *A. flavus]*, *Crptococcus, Histoplasma* [such as *H. capsulatum]*, *Pneumocystis* [such as *P. jirovecii*] and *Stachybotyrus* [such as *S. chartarum*]; fungi used in industrial production such as the genera *Aspergillus* [in particular *A. niger* and *A. oryzae*]) and members of the *Neurospora* genus, such as *N. crassa*, plant cells and mammalian cells, avian cells, either in cell culture or part of a tissue.

In general, a host cell is compatible with the plasmid vector. For example, the cell is compatible with the plasmid origin of replication. The cell is typically one in which the plasmid can be stably maintained and replicated. The host cell is also typically compatible with any detectable marker gene in the plasmid so that the gene can be expressed in the cell and the cell can thereby be screened for successful introduction and maintenance of the plasmid.

A host cell may simply be intended for manipulation of a plasmid or polynucleotide. Preferably such a strain is a laboratory strain which can be easily manipulated and maintained under laboratory conditions, e.g. *E. coli*.

Alternatively or additionally, a host cell may be used to screen for cis-regulatory sequences using an n[snare] plasmid library according to the invention and/or to test for decoy function of a putative cis-regulatory sequence using an n[snare] plasmid as described herein. The host cell may also be one in which it is desired to alter gene expression using an n[snare] plasmid or other decoy molecule as described herein.

In general a host cell comprises the cis-regulatory sequence of interest, i.e. the cis-regulatory sequence that is being screened for, or with which the decoy sequence introduced into the cell is intended to compete. Typically, in the cell the cis-regulatory sequence is operably linked to a gene or genes, the expression of which can be detected, directly or indirectly. Typically the cell comprises a promoter containing the cis-regulatory sequence, operably linked to the gene(s). By operably linked is meant that the cis-regulatory sequence and/or promoter is linked to the gene or genes in such a way that the sequence and/or promoter can function (under appropriate conditions, e.g. presence of the requisite transcription factor(s)) to regulate expression of the gene(s). Thus, when bound by the cognate transcription factor, the cis-regulatory sequence functions to regulate (repress or activate) expression of the gene or genes. The promoter may be for example, one which regulates a gene(s) which encodes a phenotype of interest, such as any of the genes or phenotypes described herein.

Functioning of the cis-regulatory sequence in the cell can be determined by monitoring for expression of the linked gene(s). This may be done by monitoring for expression of the gene directly, or by monitoring for expression of a particular phenotype which is associated with expression of the gene(s). For example, screening for function may comprise screening for production of a given metabolite or fermentation product, e.g. an antibiotic such as cinnamycin, actinorhodin and/or undecylprodigiosin; for resistance to a particular antibiotic e.g. vancomycin; or for tolerance to a solvent such as butanol. Methods for screening are described herein.

In one aspect the plasmid causes a change gene expression and/or phenotype of a host cell, e.g. an increase in antibiotic synthesis, a decrease in antibiotic resistance, or an increase in solvent tolerance in the cell.

A host cell may comprise a cis-regulatory sequence (e.g. a promoter containing the sequence) operably linked to its native (cognate) gene(s), i.e. linked to the gene or genes the expression of which the sequence (or promoter) regulates in its native occurrence. Thus, for example, where a cis-regulatory sequence of interest (or its native promoter) regulates genes(s) encoding (e.g. antibiotic or enzyme) production, a host cell may comprise a native producing cell. Where a cis-regulatory sequence of interest (or its native promoter) regulates a gene or genes encoding antibiotic resistance, a host cell may comprise a native antibiotic resistant strain, e.g. a pathogen, or a clinical isolate. Thus the cis-regulatory sequence in the cell may be operably linked to a gene or genes, the expression of which is or are regulated by that sequence in its natural context.

For example, as described in the present Examples, *S. coelicolor* is a native producer of actinorhodin and undecylprodigiosin. It has been reported that production of these antibiotics requires binding of AsfR protein to a binding site upstream of the asfS gene. *S. coelicolor* may therefore be used as a host cell when screening snares for the presence of a sequence comprising the AsfR binding site (or when introducing a decoy sequence which competes with such sequence). Competition with the native cellular AsfR binding site will result in reduced antibiotic production.

Also as described in the Examples, *S. cinnamoneous* produces cinnamycin antibiotic. *S. cinnamoneous* may be used as a host to screen snares for the presence of cis-regulatory sequences in the promoters of genes in the *S. cinnamoneous* cinnamycin biosynthetic cluster (or when introducing a decoy which competes with such sequence). Competition with the native cis-regulatory sequences can be screened for by monitoring the production of cinnamycin in transformed strains, as described herein.

Also as described, *E. coli* K12 comprises genes encoding butanol tolerance. *E. coli* K12 cells may be used to screen snares for the presence of cis-regulatory sequences in the promoters of genes encoding the tolerance (or when using a decoy which competes with such sequence). The presence of a competing sequence in the transformed cells may be assayed for by determining viability of cells in the presence of varying concentrations of butanol.

Alternatively, a host cell may comprise a model, e.g. a bacterial model, of a given cellular phenotype, such as metabolite production or antibiotic resistance. Such a model comprises the cis-regulatory sequence of interest (e.g. a promoter containing the sequence) operably linked to the native gene(s) but in a heterologous cell. In other words, the cis-regulatory sequence (and its native promoter) and the operably linked gene(s) are not present endogenously in the cell.

Typically, a model host cell comprises a bacterial species or strain which is more easily manipulated under laboratory conditions than a native strain, e.g. is non-pathogenic or more susceptible to gene transfer. In general, in the absence of a n[snare] plasmid or decoy molecule described herein, expression of the gene(s) is regulated by the cis-regulatory sequence (e.g. in its promoter). Thus the cell comprises the components necessary for the cis-regulatory sequence to function in the normal way, e.g. transcription factor to bind to the sequence and repress or activate expression of the gene(s).

A model host cell may comprise a plasmid bearing the cis-regulatory sequence and gene(s), which has been introduced to the cell or the cis-regulatory sequence and gene(s) may be integrated in the host genome. A model host may comprise a genomic fragment which comprises the cis-regulatory sequence and gene(s), wherein the fragment has been acquired from a native cell, e.g. by horizontal transfer.

A model cell may have acquired genes conferring a given phenotype of interest e.g. metabolite production, antibiotic production, antibiotic resistance, solvent tolerance, for example, a model strain may have acquired a particular phenotype by horizontal transfer of genes encoding that phenotype, e.g. antibiotic production and/or antibiotic resistance. Such a model strain may be prepared without prior knowledge of the coding genes. This is done by horizontal transfer of DNA from the native strain (exhibiting the phenotype of interest) to the model strain and by screening for gain of the phenotype.

Where the cells are to be host to a custom n[snare] library, the cells may, for example, comprise the genomic DNA or genomic fragment from which the library was derived (either endogeneously or by gene acquisition).

Suitable host cells are known in the art and are described herein in the present Examples. For example, Example 6 describes *S. coelicolor* strain M600, which is a bacterial model of vancomyin resistance.

Reporter Cells

A host cell may comprise a cis-regulatory sequence of interest (or a promoter of interest comprising cis-regulatory sequences) operably linked to a gene(s) the expression of which is not regulated by that sequence or promoter in its native context (a non-native gene). Such a gene is referred to as a reporter gene. Typically, the reporter gene is operably linked to a promoter sequence which comprises the cis-regulatory sequence of interest.

Function of the cis-regulatory sequence can be determined by determining expression of the reporter gene. Typically the reporter gene is one whose expression can be easily detected and screened for. For example, the reporter gene may encode a fluorescent compound, or antibiotic resistance. Examples of reporter genes are luciferase, or the neo gene encoding kanamycin resistance. Such reporter cells are particularly useful where the cis-regulatory sequences (or promoters) natively control expression of gene(s) which have no easily scorable phenotype.

In one embodiment, the reporter gene is negatively regulated by binding of a transcription factor (transcriptional repressor) to the cis-regulatory sequence of interest. Such a host cell is suitable for screening for cis-regulatory sequences which negatively regulate (repress) expression of their cognate gene(s). In an alternative embodiment, the reporter gene is positively regulated by binding of a transcription factor (transcriptional activator) to the cis-regulatory sequence. Such a host cell is useful for screening for cis-regulatory sequence which positively regulate expression of their cognate gene(s).

Any suitable host strain may be used in the reporter system. Suitable strains are known in the art and are described herein. Where appropriate, strains will have been chosen that contain no genomic copy of the reporter gene. Similarly reporter strains can be engineered by targeted deletion of genes used as reporters from the genome prior to the introduction of the true reporter gene.

The reporter gene and cis-regulatory sequence (e.g. in a promoter) may be plasmid borne. Alternatively, the reporter gene and cis-regulatory sequence (or promoter) may be integrated in the host genome. For example, the reporter system may have been introduced to the host on an integrative plasmid, e.g. pSET152. Where the system is plasmid borne, typically the plasmid comprises a detectable marker gene that allows positive selection for the plasmid in the host cells. For example, the detectable marker gene may encode antibiotic resistance, e.g. the aac gene which encodes resistance to apramycin.

The inventors have developed a generic reporter cell system which may be used to screen for the presence of a cis-regulatory sequence, for example in an n[snare] plasmid library or n[snare] plasmid described herein. The screening cell and methods allows screening for the presence of the cis-regulatory sequence on the basis of cell viability. Expression of the reporter gene is determinative for cell viability or survival under appropriate culture conditions. Under the conditions of the assay, host cells are only viable if a sequence has been introduced into the cell which is competing with the cis-regulatory sequence of interest (e.g. in the promoter of interest) for binding of transcription factor. The system is referred to as a "dead or alive" screening system. The system can be automated, and has the advantage that it can be used to screen cells cultured in liquid media.

When the cis-regulatory sequence of interest functions to repress expression of an operably linked gene, the reporter gene typically encodes a product which is necessary for cell survival under appropriate culture conditions. For example, the reporter gene may encode antibiotic resistance such that when the host cell is cultured in the presence of the antibiotic, cell survival is only possible in the presence of a competing sequence which inhibits binding of transcription factor to the cis-regulatory sequence linked to the reporter and allows expression of the reporter antibiotic gene. Suitable antibiotic resistance genes include, for example, the kanamycin resistant gene neo. This allows detection of cis-regulatory sequences that are bound by transcriptional repressors. Other suitable genes are known in the art.

In this case, a host cell typically comprises other components which are necessary for the cis-regulatory sequence to function. The cell typically comprises (e.g. expresses) the transcription factor(s) necessary for binding to the cis-regulatory sequence. The host cell may already comprise the cis-regulatory sequence, e.g. a promoter comprising the cis-regulatory sequence. The host cell may comprise a genomic fragment from which the cis-regulatory sequence of interest is derived.

When the cis-regulatory sequence functions to activate expression of an operably linked gene, the reporter gene encodes a product which is lethal for the cell under appropriate culture conditions. Such a gene is often referred to as a suicide reporter gene. Cells are only viable (under appropriate culture conditions) in the presence of a competing sequence which inhibits or prevents transcription factor binding to the cis-regulatory sequence linked to the reporter. An example of a suicide reporter gene is, for example, the glucose kinase gene (glkA). This gene converts a metabolite (2 deoxy glucose (DOG)) to a toxin. Thus, expression of the glkA gene is lethal to the cell when cultured in the presence of DOG. This allows detection of cis-regulatory sequences that are bound by transcriptional activators. Other suitable genes are known in the art.

Typically, in this system the host does not otherwise express the reporter gene but comprises the components necessary for the cis-regulatory sequence to function. The cell typically comprises e.g. expresses, a transcription factor(s) necessary for binding to the cis-regulatory sequence(s). In such a system, any activity at the cis-regulatory sequence will be due to positive transcription factors (activators) derived from the host cell genome. By searching in this background, it is possible to find upregulators of heterologous expression from the chromosome of the host. By titrating these activators off the cis-regulatory sequence linked to the reporter and onto a decoy sequence, e.g. an n[snare] plasmid, expression of the reporter gene, e.g. glkA, is prevented and the cells are viable even when grown in the presence of the DOG metabolite.

The dead or alive reporter system can be adapted for use with any suitable cis-regulatory sequence, such as any of those described and/or identified herein. For example the cin7 promoter, derived from the cinnamycin biosynthetic cluster in *S. cinnamoneous* may be used as described in Example 3. The cin7 promoter may be operably linked to the neo gene encoding kanamycin resistance as described in the Examples. This may be comprised in an integrative plasmid such as the pSET152 backbone used in the examples. The plasmid also carries a suitable marker gene (the aac gene encoding apramycin resistance). The plasmid may be introduced into or integrated into an *S. lividans* host strain (1326) which additionally carries the cinnamycin biosynthetic pathway. Such a reporter cell is suitable for screening, for example, an n[snare] plasmid library derived from the *S. cinnamoneous* genome or genomic fragment comprising the cinnamycin biosynthetic cluster as described herein.

Alternatively, the cin7 promoter may be operably linked to the glkA reporter gene and in the same way integrated into an integrative plasmid. In this case, a suitable host strain would be the *S. lividans* TK24 strain which lacks the cinnamycin biosynthetic cluster and also lacks the glkA gene.

In one aspect, the invention relates to the reporter cells described and prepared according to the present Examples.
Methods for Identifying and Characterising Cis-Regulatory Sequences The principle of use of the present n[snare] plasmids is illustrated in FIG. 2. If the snare sequence in the plasmid comprises a transcription factor binding site that comprises and/or competes for transcription factor binding with, a cis-regulatory sequence in the cell into which the plasmid is introduced, this can be detected as a change in expression of the gene which is regulated by that cis-regulatory sequence in the cell. Thus n[snare] plasmids can be used to identify cis-regulatory and decoy sequences. The plasmid can also be used with a snare comprising a known decoy sequence, to disrupt gene expression in the cell.

Thus the n[snare] plasmids of the invention can be used in a number for a number of different purposes. As above, a library of n[snare] plasmids can be used to screen for putative cis-regulatory sequences, e.g. in a fragment of genomic DNA using a custom n[snare] library. An n[snare] plasmid can be used to test a particular sequence for decoy function. In any of these methods, a snare sequence is identified as comprising a cis-regulatory sequence or a sequence that competes with a cis-regulatory sequence for transcription factor binding, if the snare in the n[snare] plasmid is able to titrate transcription factor from the cis-regulatory sequence present in the host (as determined by an alteration in gene expression or host cell phenotype). Thus, the sequences identified using the methods may also act as decoy sequences, and in one aspect, the methods can be considered as methods of identifying decoy sequences and molecules. An n[snare] plasmid comprising a decoy sequence can be used to modulate gene expression and/or phenotype in a host cell.

Thus in one aspect the invention provides methods for identifying and/or characterising cis-regulatory and decoy sequences. In general such a method comprises:
1. providing an n[snare] plasmid or n[snare] plasmid library as described herein;
2. introducing the n[snare] plasmid or plasmid library into a host cell(s) wherein the host cell comprises the cis-regulatory sequence of interest operably linked to a gene or genes, the expression of which can be determined directly or indirectly; and
3. determining the expression of the gene (or genes), or alteration of phenotype, in the presence and absence of the n[snare] plasmid or plasmid library.

An n[snare] plasmid or n[snare] plasmid library for used in the method may be as described herein. The snare in each plasmid comprises the sequence to be tested for competing function.

In general, a host cell comprises a cis-regulatory element of interest (e.g. a promoter comprising the cis-regulatory element) operably linked to a gene or genes, the expression of which can be directly or indirectly monitored or determined. For example, the expression may be monitored by determining expression of the particular gene or genes or by monitoring for a particular phenotype encoded by the gene or genes.

Suitable host cells for use in the present methods have been described herein and include, for example, native strains, clinical isolates, laboratory models and reporter cells. The "dead or alive" reporter screening system described herein may be used.

In Examples 1 and 2 herein it is demonstrated that the decoy-oligonucleotide approach can be adapted to a plasmid format, including confirmation that use of a library to identify cis-regulators of a defined sequence is achievable. A possible limitation of this iteration of the n[snare] library-based approach is that it may not be optimally suited to regulators of subtle or complicated phenotypic changes. In many circumstances the phenotypic alteration may not be readily detectable and may need a complicated system of scoring, such as quantifying metabolite production by chromatographic analysis. There would be obvious advantage to the creation of a reporter system where the phenotype scoring was standardized, allowing n[snare] library screening to be accelerated so that it can be conducted at high-throughput.

A possible technical limitation of the approach taken in Example 2, namely of screening all the members of a library for change of phenotype, is that the need to physically plate or culture all the members of entire libraries places a practical limitation on how many colonies can be screened, and hence the amount of DNA that can be surveyed. It is not feasible to survey large genomic fragments that would generate libraries with >100000 members, which equates approximately to 25 kb of sequence. As described below, both the reporter genes used in a system developed by the inventors confer viability to cells that have an n[snare] plasmid containing a candidate cis-regulatory element. Hence, selection is by viability allowing rapid enrichment of candidate sequences in liquid culture simply by letting the majority of cells that do not contain a candidate plasmid perish.

Figure 7:
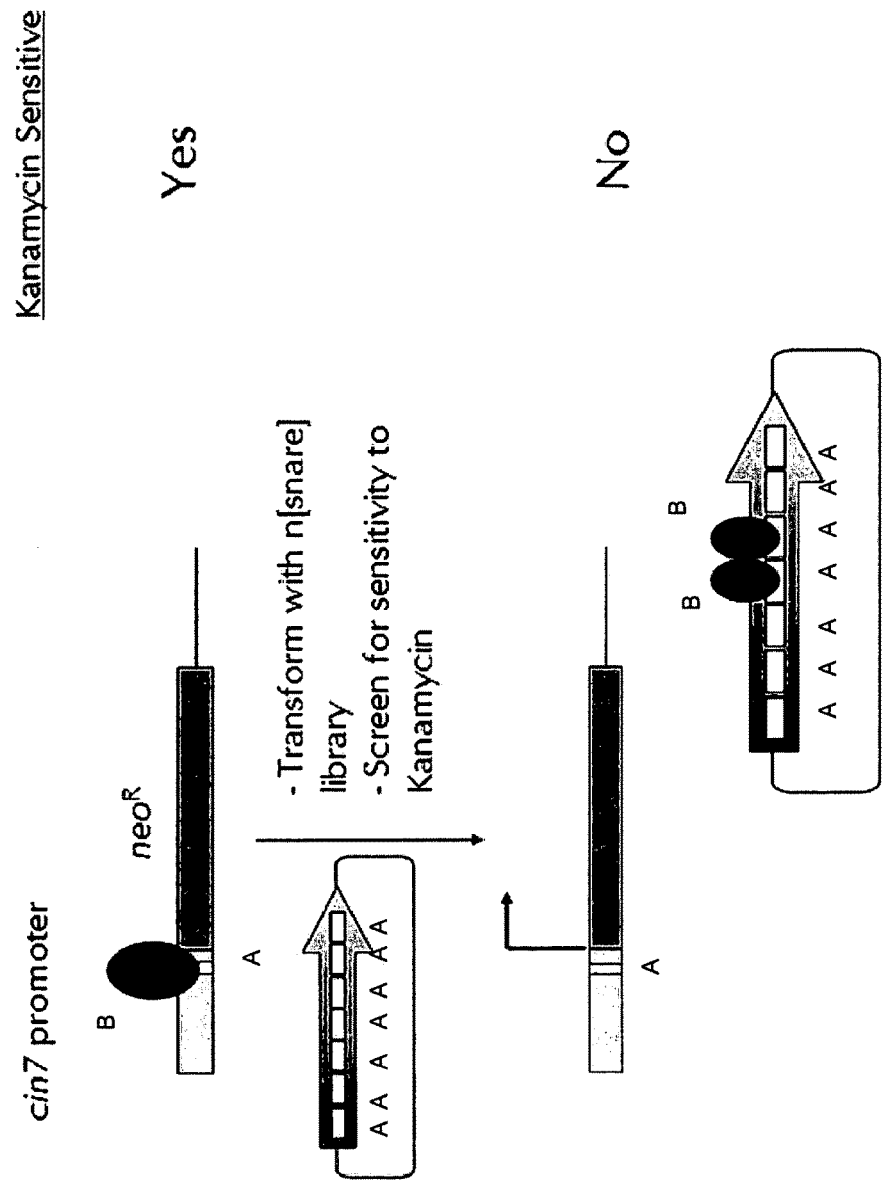
FIG. 7. Reporter constructs developed to identify cis-regulatory elements within an n[snare] plasmid library. In this figure the targeted promoter of the cin7 gene from the cinnamycin biosynthetic cluster of the producing strain of S. cinnamoneous is used to drive expression of the neo gene encoding resistance to the antibiotic kanamycin.
Figure 8:
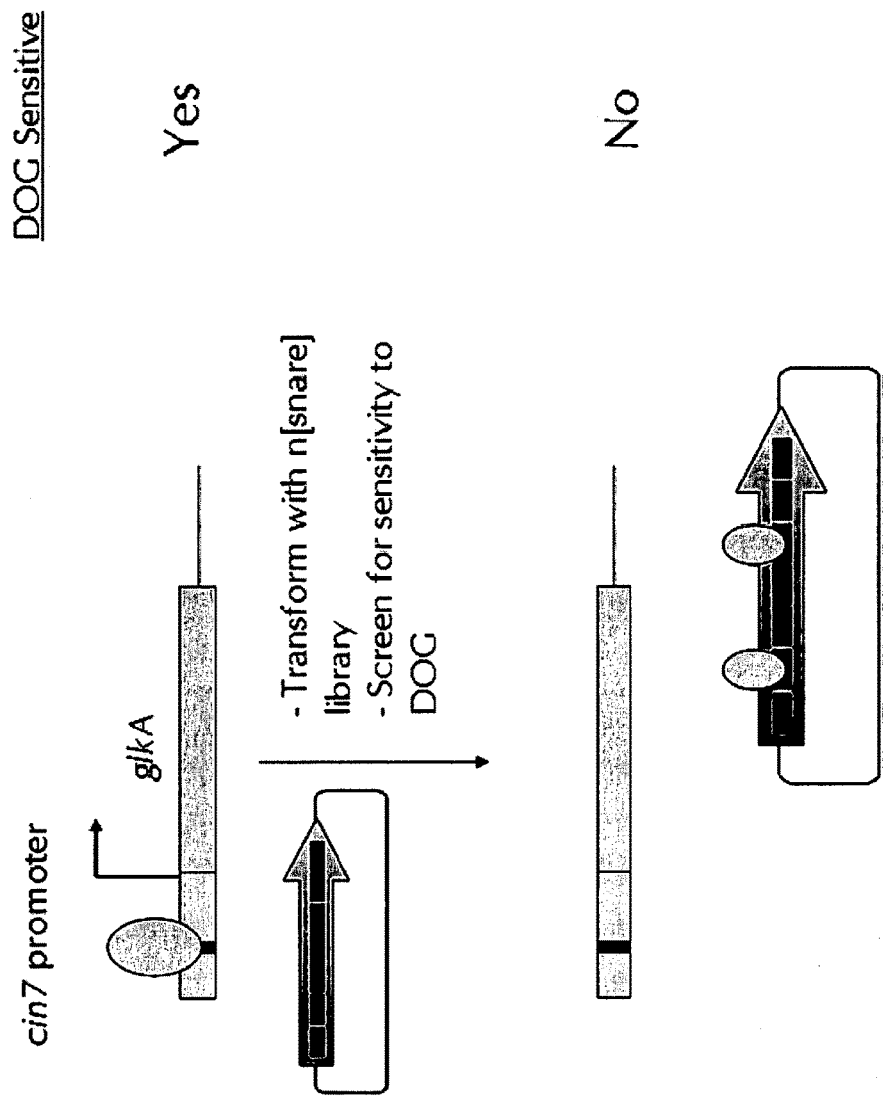
FIG. 8. Detecting negative cis-regulators of cinnamycin production using a generic reporter system and a custom n[snare] library. A simple adaptation makes the reporter system capable of detecting positive regulation by creating a cassette consisting of a chimeric reporter gene incorporating the coding sequence of the glucose kinase gene (glkA) driven by the targeted promoter.

Hence the inventors have adapted the n[snare] library approach described herein to address these issues by developing generic reporter-based assay systems. In this iteration, negative and positive regulators are detected by their effect on reporter genes encoding antibiotic resistance (FIG. 7) or metabolite sensitivity (suicide reporters) as shown in FIG. 8. The target promoters are introduced into the reporter cassettes to allow detection of either negative regulation (transcriptional repressors) or positive regulation (transcriptional activators). This approach solves the problem of needing a scoreable phenotype as under normal circumstances each reporter causes cell death, it is only when an n[snare] plasmid from the library relieves this by titrating off the transcription factor that the cells can grow. Hence selection for both reporters relies on cell survival, which greatly expedites the screening process. Another feature of the system is that such dead-or-alive screens can be readily automated as a basis of rapid, comprehensive or high-throughput screens. It is also possible to identify regulatory sequences controlling promoters which in their natural context have no easily scoreable phenotype.

The plasmid or plasmid library is introduced to host cells in the present methods by any suitable means. Suitable means are known in the art. If the n[snare] plasmid is conjugative, the plasmid may be introduced by conjugation. Other means such as transfection/transformation may also be used.

Typically host cells are then monitored for stable propagation of the plasmid by selecting for expression of a detectable marker gene on the plasmid as described herein, e.g. an antibiotic resistance gene. Cells are cultured under conditions which select for cells expressing the particular marker, e.g. in the presence of the antibiotic.

Preferably the method comprises the use of one or more suitable controls. For example, such controls include host cells untreated with plasmid, host cells into which has been introduced an empty plasmid vector, and host cells into which has been introduced an n[snare] plasmid comprising a scrambled putative cis-regulatory sequence.

Once the plasmids have been introduced into the cells, the cells are screened for expression of the gene or genes operably linked to the cis-regulatory sequence (or promoter) of interest. Expression in the presence of the snare sequence (in the n[snare] plasmid) is compared to expression in the absence of the snare. Clones which produce an alteration in expression of the test gene(s) (e.g. an alteration of cell phenotype) are selected as likely to comprise a cis-regulatory sequence. DNA from these clones is isolated, and the putative cis-regulatory sequence (or decoy sequence) isolated.

Screening for an alteration in gene expression may be carried out by any suitable method. Screening may comprise detecting or measuring the expression product of the gene(s), e.g. by assaying for the function of the gene product, or may comprise determining a change in a host cell phenotype associated with expression of the gene(s).

For example, changes in expression of a gene(s) encoding production of a metabolite, e.g. an antibiotic, may be monitored by determining expression of the given metabolite, e.g. the amount (or presence of absence) of metabolite or function of the metabolite.

For example, actinorhodin and undecylprodigiosin are pigmented antibiotics. Actinorhodin is blue and undecylprodigiosin is red. Thus expression of these antibiotics can be easily monitored by colorimetric techniques.

Production of some metabolites or antibiotics can be monitored by using indicator bacterial strains and suitable plate assays. For example, production of cinnamycin can be detected by a plate assay using the indicator strain *Bacillus subtilis*, and suitable media e.g. solid R2YE agar. Cells are typically cultured on agar plates which have been seeded with the indicator strain. The expression of the antibiotic is determined by the extent of reaction, e.g. killing, of the indicator strain, e.g. by the diameter of a halo on an agar plate.

Expression of antibiotic resistance gene(s) or phenotype, e.g. vancomycin resistance, kanamycin resistance, may be determined by culturing host cells in the presence of the antibiotic and determining sensitivity to the antibiotic. Typically cells are also cultured in the absence of the antibiotic as a control.

Similarly, genes encoding solvent tolerance, e.g. butanol tolerance, may be monitored by culturing the cells in the presence of the solvent (again typically a control is carried our in which cells are cultured in the absence of the solvent).

In some instances, screening for expression of the relevant gene(s) comprises determining host cell viability under suitable culture conditions. For example, when the gene or genes encode antibiotic resistance, screening may comprise culturing cells in the presence of the antibiotic and determining whether the cells are viable. In a screen comprising the "dead or alive" reporter host cells, under the given culture conditions, cells are only viable if the n[snare] plasmid introduced into the cells comprises a sequence which can compete with the cis-regulatory sequence of interest. Thus screening the cells comprises culturing the cells under conditions in which expression of the reporter gene(s) (the gene(s) operably linked to the cis-regulatory sequence of interest) is determinative for host cell viability, and isolating viable cells.

The present methods may comprise culture of the host cells in liquid media, as described herein, e.g. if the cell phenotype which is being determined is cell viability. This may have the advantaged that only a small number of cells remain to be analysed.

Screening may comprise use of DNA subtraction techniques as described herein. This may be particularly useful where expression of the relevant gene(s) affects cell viability (under suitable culture conditions).

Typically a DNA subtraction step comprises subtracting a population of DNA from cells with a given phenotype and from cells without the phenotype.

For example, in some instances, introduction of a sequence comprising a competing cis-regulatory sequence, will result in host cells becoming non-viable under suitable culture conditions. This may be the case if, for example, the cis-regulatory sequence of interest activates expression of an antibiotic resistance gene(s) or represses expression of a lethal gene (expression product lethal under particular culture condition). When a competing cis-regulatory sequence is introduced into the cells, e.g. in a snare of an n[snare] plasmid, the competing sequence titrates transcription factor and results in reduced expression of the antibiotic resistance gene or expression of the lethality gene.

Transformed cells are typically cultured (a) under conditions in which cells with disrupted expression from the cis-regulatory sequence will be non-viable; and (b) under conditions in which the cells will be viable. Populations of DNA are isolated from the two cultures (typically after isolation and/or amplification of the introduced DNA, e.g. the n[snare] plasmid or plasmid insert), and subtracted (e.g. by hybridisation). It is then possible to determine the DNA that is missing from the cells in culture (a) and which comprises the likely competing cis-regulatory sequence.

For example, if the phenotype under investigation is antibiotic resistance, a cis-regulatory sequence of interest introduced into a host cell, e.g. in a snare of an n[snare] plasmid, may restore sensitivity to the antibiotic. Transformed cells are cultured (a) in the presence of antibiotic; and (b) in the absence of antibiotic. Cells containing the cis-regulatory sequence of interest will die in the presence of the antibiotic. DNA is isolated from both cultures, and nucleic acid comprising the snare sequences isolated, e.g. by PCR amplification. By subtracting the populations of snare sequences, it is possible to isolate those missing from the antibiotic treated samples.

In one aspect, the enriched population of snare sequences may then be recloned and the selection process repeated.

Once cells displaying altered gene expression or phenotype have been isolated, DNA from these cells is isolated. Typically, the DNA which was introduced into the cells, e.g. the n[snare] plasmid DNA and/or the plasmid insert, is isolated. The snare which caused the altered expression, and which comprises the likely cis-regulatory (or decoy) sequence can then be determined. This may be done, for example, by PCR amplification.

When the present method comprises use of an n[snare] plasmid library, the method may additionally comprise one or more further steps.

For example, the method may comprise a library hybridisation step. Due to the complexity of libraries used in these sorts of enrichment procedures it is rare to generate samples that entirely consist of the desired sequences. Generally there is a background of false negatives within the enriched sample that need be rejected and not carried forward for further analysis. The library hybridization strategy is designed to do so by detecting n[snare] plasmids that are common to all independent repeats of the screening process, the logic being that if plasmids carrying the same sequence are detected in independent repeats at an occurrence above background then those should be the ones carried forward for further analysis. An overview of the process is given in FIG. 9.

Typically when using the library hybridization strategy, x independent repeats of the above screening method (comprising steps (1) (2) and (3)) are carried out. For example, x may be 2, 3, 4, 5, 6, 7 or 8.

In each repeat, clones producing an alteration in gene expression/phenotype are selected as described. Plasmid DNA is isolated from the clones and labelled to create a pooled probe sample (P). For example, the plasmid DNA may be labelled by random priming PCR, e.g. using a DIG-labelled dUTP molecule as in the present Examples.

The clones are also plated onto suitable media at a concentration which allows individual colonies to be distinguished. Typically at this stage, a sample of each colony is taken and further cultured to provide a source of plasmid DNA if necessary at a later stage.

Total DNA is extracted from each colony and immobilised on a suitable matrix, e.g. a nylon membrane, for example by hybridisation. DNA from each colony is at an addressable position on the matrix. Each matrix is then separately hybridised with each of the probe sets. Samples which are common to more than one repeat are typically selected for further analysis.

Thus for example, if x=4, four probe sets and four matrices, e.g. 4 nylon membranes are prepared. Each of the 4 probe sets, P1, P2, P3 and P4 is hybridised to each of the 4 filters, F1, F2, F3 and F4. Hybridisation of P1 with F1 produces a chromatogram where every sample is detected. F2, F3, or F4 samples which hybridise with P1 would be potential candidates for further analysis. The more probe samples that a colony hybridises with, the stronger that clone is as a candidate.

Self hybridisation (e.g. P1 with F1) may also be use to detect false positives in a screen.

The method of the invention may further comprise repeating the selection process one or more times, so that selection is iterative. Thus, clones selected from a first screen may be used to transform the host cells again and the screen is repeated.

The n[snare] library approach described herein could be used to identify cis-regulatory sequences that affect bacterial phenotypes with important medical consequences, an example being prevention of induction of antibiotic resistance mechanisms in pathogenic bacteria infecting humans (FIG. 6). The schematic in this figure shows how a library of n[snare] plasmids is used to identify cis-regulatory sequences controlling antibiotic resistance when nothing is known about the genetic pathway of the mechanism. In this example the genes conferring antibiotic resistance are moved into a convenient bacterial host, such as *S. coelicolor* or *E. coli*, by horizontal gene transfer to create a convenient bacterial model. This can be done without prior knowledge of what the genes are by screening for the gain of antibiotic resistance. A similar mechanism will have moved the same resistance genes into the pathogenic strains detected in the clinic. Libraries of n[snare] plasmids are created from the genomic fragment carrying the resistance genes, the entire genome of the naturally resistant or clinical isolate, or from random oligonucleotides to create universal libraries conceivably containing every possible cis-regulatory sequence. Such libraries are introduced into the bacterial model and the transformant screened for increased susceptibility to the targeted antibiotic. This is either accomplished by direct scoring of the phenotype or by using established DNA-subtraction techniques. Depending on the complexity of the system, the process is performed singly or iteratively to identify a single cis-regulatory sequence or cocktail of such sequences, which is then used to synthesize or manufacture corresponding TFDs. These are then validated on either the resistant or clinical isolates, before proceeding to an appropriate animal model, such as a mouse model, where the efficacy of the decoys is tested by treating an animal infected with a pathogenic strain which is resistant to treatment with antibiotic alone.

As stated, the biology of the genome, the pattern of gene expression and timing of replication, is primarily controlled by DNA-protein interactions, and mapping these interactions may be a prerequisite to the attempts to control the genes. Microarray analysis can produce a survey of entire genomes to identify which genes are expressed, but to date no technology exists to identify, on a similar scale, the proteins (trans-regulators) and their cognate binding sites (cis-regulatory elements) that determine the pattern of expression. Example 4 herein and the embodiment of the invention described therein addresses this deficiency and develops our current technology to form a generic tool capable of rapidly identifying the cis-regulatory elements throughout the genome, to delineate genetic networks and assert control over them. The method according to this aspect of the invention identifies regulatory elements throughout the genome which control expression of targeted genes. As a fast and generic system for delineating regulatory networks, the tool has the potential to produce gold-standard data to support the drive towards systems biology, and utility in defining regions for knowledge-based genetic engineering and accelerate the mapping of disease-causing genetic variation.

In some instances there is a priori knowledge of the genetic machinery underpinning the targeted phenotype, e.g. known promoters within the cinnamycin cluster. More commonly, little information is known about the genetic networks and their regulation underpinning targeted phenotypes. For example many mechanisms of antibiotic resistance amongst pathogenic infections appearing in clinics are not understood at the genetic level, and this fact presents a serious barrier to the development of treatments to solve this problem. Likewise, in the context of industrial biotechnology, a technique which could favourably alter complex characteristics of bacteria without need of prior knowledge of genetic determinants would be valuable. An example of this would be engineering a bacterium to be solvent tolerant to improve its efficiency in fermenting sugars in the process of biofuel production. Examples of both clinical and industrial applications of the instant technology are given herein.

To demonstrate the efficacy of this approach to detect cis-regulatory elements without prior knowledge of a genetic pathway, the inventors used n[snare] libraries to increase butanol tolerance in *Eschericihia coli* (Example 4). One of the libraries was derived from the entire *E. coli* genome using similar techniques as described in Example 2. The second library was a 'universal n[snare]' library conceivably consisting of direct copies of every possible 9 nucleotide sequence, or any such length desired. The universal n[snare] library is made using similar methods to that described in Example 2 for the creation of a single AfsR n[snare] plasmid with the exception that instead of having an oligonucleotide sequenced containing a central section with a defined cis-regulatory sequence, random sequence is inserted instead (and at this stage the length of the sequence can be controlled). The procedure for using such n[snare] libraries to detect novel cis-regulators of butanol tolerance is similar to that described in Example 3 in the sense that the targeted phenotype is scored by measuring viability against increasing concentration of solvent.

n[snare] plasmid libraries as described and/or prepared according to the methods herein, may also be used to identify cis-regulatory sequences by screening the library directly for binding by one or more transcription factors.

The present methods to identify and characterise cis-regulatory elements may further comprise the use of a mapping procedure using a combination of footprinting and exonuclease as described herein.

Methods for Mapping Boundaries of Cis-Regulatory Sequences

In one aspect the invention provides a method for mapping the boundaries of protein binding sites in DNA. This method may be used for more precisely mapping the boundaries of such binding sites.

The method may be used to map the boundaries of cis-regulatory sequences. The method may be used in combination with the method described herein for identifying and characterising cis-regulatory sequences, e.g. a method using an n[snare] plasmid or a plasmid library as described herein. By providing more precise sequence information about cis-regulatory elements and thus the binding sites for protein regulators such as transcription factors, the method is useful for designing decoy oligonucleotides which, when introduced into a suitable cell, will compete with a cis-regulatory sequence in the cell for binding of the protein regulator.

The present method uses a combination of an enzyme or chemical agent with non-specific DNA nicking capacity, (e.g. DNAse I) and a 5'-3' exonuclease enzyme (e.g. T7 exonuclease) in a modified footprinting protocol. Alternatives to. DNaseI would include treatment of the cells with potassium permanganate or free radicals generated by hydroxides. Another example of a suitable exonuclease that could be used would be lambda exonuclease. The protocol is designed to map the 5' boundaries of the protein-DNA complex on each strand of the DNA and hence define the protected region of DNA within the complex, comprising the cis-regulatory element. The DNAse I introduces nicks into the DNA surrounding the complexes. These serve as substrates for the 5'-3' exonuclease activity of the 5'-3' exonuclease enzyme. The combined action of the two enzymes demarcates the 5' boundaries of the protein-DNA complex on each strand of DNA. Thus the present method has the advantage that it can detect all of the boundaries of DNA-protein complexes in a given region, e.g. a promoter region, not just those closest to restriction sites.

Figure 13:
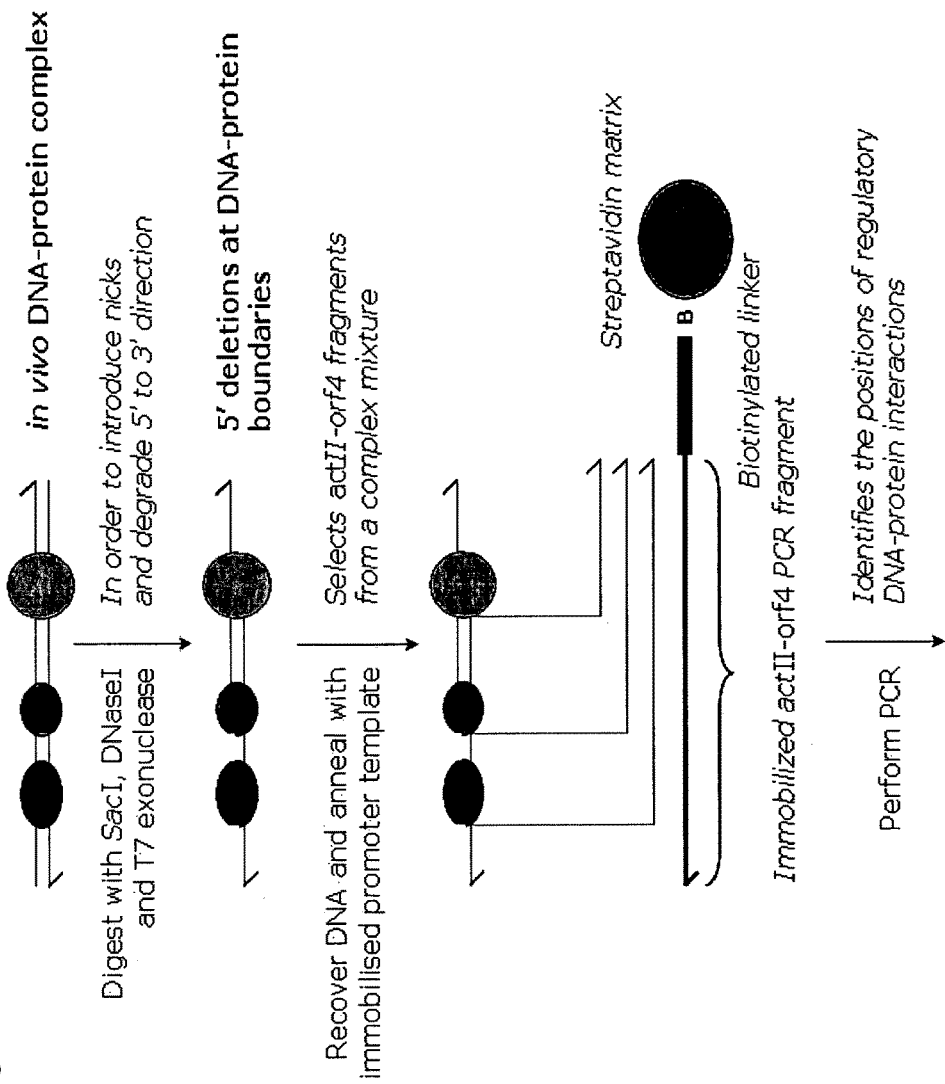
FIG. 13. Schematic overview of the protocol for in vivo T7 exonuclease/DNaseI mapping procedure. The novel combination of T7 exonuclease and DNaseI in a footprinting protocol allows detection of all the boundaries of DNA-protein complexes within a promoter region, and not just those closest to a chosen restriction site.

The principle of the present mapping method is illustrated in FIG. 13. Typically the method comprises:
1. providing a protein-DNA complex;
2. carrying out a digestion with
   a. an enzyme having non specific DNA nicking ability e.g. DNaseI,
   b. a 5'-3' exonuclease (T7 exonuclease);
   c. optionally, a restriction enzyme that cuts a short distance upstream of the likely position of the DNA-protein complex; in the case of the actIIorf4 gene this was determined to be SacI; and
3. determining the position of the 5' deletions generated in each DNA strand in (2) relative to a known fixed point on the DNA strand.

The protein-DNA complex may be any complex of interest. In one example, the method is used to map the boundaries of protein-DNA complexes in a DNA promoter region, e.g. of protein-DNA complexes at cis-regulatory sequences. In one example, the protein-DNA complex may be a transcription factor-DNA complex which regulates expression of one or more antibiotic resistance genes in a prokaryote or eukaryote. In another example, the method may be used to map protein-DNA binding sites in the *S. coelicolor* actII-orf4 promoter as in the present Examples.

Mapping may be carried out during a transcriptional state of interest e.g. during repression if the cis-regulatory element of interest is involved in repression i.e. bound by a transcriptional repressor, or during active expression from a promoter if the cis-regulatory sequence of interest is bound by a transcriptional activator.

Thus, for example, in one aspect, mapping may be carried out in vivo (e.g. using freshly harvested cells) at a stage when gene expression in the cells is known to be repressed or activated. Typically cells are cultured and isolated at the appropriate transcriptional stage. Cells may be permeabilized with detergents which allow enzymes to enter the cells. Thus, if the protein-DNA complexes to be mapped function to repress expression of a given gene(s) or phenotype, the protein-DNA complexes are tested at a point when expression of the gene(s) or phenotype is repressed. Conversely, if the protein-DNA complexes to be mapped function to activate expression of a given gene(s) or phenotype, the protein-DNA complexes are tested at a point when expression of the gene(s) or phenotype is active. Typically, cells can be monitored for expression of the given gene(s) or phenotype, and isolated at the appropriate stage.

For example, if the cis-regulatory sequence of interest (in the protein-DNA complex) has a role in repression of antibiotic production and antibiotic production is known to occur late in cell growth then the producing cells are cultured and harvested prior to this late stage of growth.

Cells may be prokaryotic or eukaryotic. In one example, the cells are prokaryotic, e.g. bacterial cells. For example, an actinomycete such as a *streptomyces* species, e.g. *S. coelicolor*, for example *S. coelicolor* A3 (2), (strain M145 or M600), *S. lividans*, *S. cinnamoneous*, or *E. coli* may be used.

Typically, the amount of non-specific enzyme (DNaseI) and exonuclease (e.g. T7) to be used in the method is determined empirically, as describe herein in the present Examples.

Use of a restriction enzyme (c) which cuts at a restriction site upstream of the likely position of the DNA-protein complex produces a standard 5' end for all of the complexes, to which oligonucleotides can be annealed in subsequent capture and amplification steps.

Once digestion in (2) is complete, the digested nucleic acid is recovered. Digestion creates 5' deletions on each DNA strand. By determining the position of these 5' deletions on each strand, e.g. relative to a known fixed point on the strand, it is possible to precisely map the protein binding site on the DNA.

One way of determining the position of the 5' deletions on each strand is as follows. Once recovered, the digested DNA is denatured either by heating or treatment with basic solutions, such as 1M NaOH, and hybridised to a strand of complementary DNA comprising the binding site(s) of interest. For example, the complementary DNA may comprise a fragment of a promoter (containing the cis-regulatory sequence(s) of interest). A PCR fragment of the promoter can be used. In general the complementary DNA strand comprises a linker at one end. An amplification reaction can then be carried out, e.g. PCR, using a labelled primer that binds to the promoter or linker.

The sizes of the labelled amplification products are then determined, e.g. by PAGE, or other methods such as capillary electrophoresis. In general, although the precise boundaries of the protein-DNA complex are not known, the approximate position, and hence the sequence of the DNA region comprising the protein binding site of interest can be determined from this data. For example, as the sequence of the promoter region will be known, a comparison of the size of the labelled fragments, and the position of the primer binding site with the sequence of the DNA region comprising the protein binding site(s), will make it is possible to determine the precise position in the DNA sequence of the 5' boundary of the protein-DNA binding complex.

Boundaries on the opposite DNA strand are mapped in the same way, but using a DNA strand with a linker at the opposite end.

Typically, the complementary DNA strand is immobilised. For example, the linker may allow immobilisation to a solid matrix. For example, the linker may be biotinylated for immobilisation to a streptavidin matrix. Immobilisation has the advantage that the digested DNA strands of interest can be easily isolated from the total digested DNA sample.

In one aspect the invention relates to a method for identifying a cis-acting regulator of gene expression of a prokaryotic or eukaryotic gene, which comprises either or both:
(a) conducting mapping of protected nucleic acid sequences;
(b) providing a library of n[snare] molecules wherein said library contains sequences representing all possible regulatory sequences from the genome of said prokaryote or said eukaryote, and either (i) identifying factors which bind to said library or (ii) introducing said library of n[snare] molecules into an organism which can indicate differential activation or suppression of a target gene as compared to when said n[snare] molecules are not introduced. The method may be conducted in vivo. Where the method is in vivo, it may be conducted with a bacterium and may comprise contacting the bacterium with effective amounts of DNase 1 and T7 exonuclease such that regulatory sequences protected by transcription factors remain intact while the remainder of the genome of said bacterium is destroyed.

Once identified according to the methods herein, cis-regulatory sequences may be used in screening assays to identify transcription factors.

Methods for Modulating Gene Expression and/or Phenotype

The n[snare] plasmids and methods herein may be used to identify and characterise sequences which compete with a given cis-regulatory sequence in a cell for binding to the cognate transcription factor.

Such sequences may be used to prepare decoy sequences. A decoy sequence mimics the native binding site (cis-regulatory sequence) for a regulatory protein (e.g. transcription factor). When introduced into suitable host cells comprising the cis-regulatory sequence (by a method described herein or otherwise), the decoy sequence competes with the cis-regulatory sequence in the cell for binding to the cognate transcription factor.

When such competition occurs, there is a concomitant alteration in expression of a gene(s) whose expression is regulated by the cis-regulatory sequence. This may cause a modulation in cell phenotype, e.g. antibiotic production, antibiotic resistance, solvent tolerance, as described herein.

It will be appreciated that an n[snare] plasmid which causes an alteration in gene expression or phenotype according to the methods described herein may be used as a decoy molecule in the present methods. A snare sequence identified as competing with a cis-regulatory sequence for transcription factor binding according to the methods described herein may be used as a decoy sequence.

Accordingly, in one aspect the invention relates to methods for modulating gene expression and or phenotype in a cell, comprising use of decoy sequences.

In general, a method for modulating expression of a gene or genes according to the invention comprises:
(a) providing a polynucleotide comprising a binding site for a transcription factor (a decoy sequence); and
(b) introducing the polynucleotide into a cell, wherein the cell comprises the gene or genes operably linked to a cis-regulatory sequence which comprises the transcription factor binding site or which competes with the transcription factor binding site for binding of transcription factor.

Generally, the decoy sequence (transcription factor binding site) in the polynucleotide is not operably linked to a gene. The transcription factor binding site may be isolated from any other elements of a cognate promoter.

The polynucleotide comprising the decoy sequence may be referred to as a decoy polynucleotide.

The decoy polynucleotide may comprise a plasmid vector. For example the decoy polynucleotide may comprise an n[snare] plasmid as described herein and/or prepared according to a method described herein.

The decoy polynucleotide may comprise more than one copy of the decoy sequence. The polynucleotide may comprise a multimeric molecule comprising multiple copies of the decoy sequence. For example, from 1 to 1000 copies. Typically there are two or more copies, for example, 2-1000 copies, e.g. at least 10, 20, 30, 40, 50, 60, 70, 80, 90, 100, 200, 300, 400, 500, 600, 700, 800 or 900 copies. For example, there may be 10-200, 10-150, 20-120, 20-100, 30-100, 30-80, 30-50, 30-40 copies. For example, there may be 30 copies of the decoy sequence. Typically there are multiple copies of the decoy, for example, multiple direct repeats of the decoy sequence.

The decoy polynucleotide may comprise additional sequence to the decoy sequence. Typically the additional sequence results in increased resistance to degradation of the decoy sequence due to the action of exo- and/or endonucleases. The decoy polynucleotide may comprise at least one element of secondary structure. Typically this secondary structure results in increased resistance to degradation of the decoy sequence due to the action of exo- and/or endonucleases. The decoy polynucleotide may comprise modified bases or sugars to confer greater nuclease resistance. The decoy polynucleotide may comprise 2' OH nucleotides or amines at the termini of the polynucleotide to reduce or inhibit exonuclease activity. In one aspect, the decoy polynucleotide may comprise a linear oligonucleotide. The decoy polynucleotide may comprise circular double stranded DNA (a so-called dumbbell structure). In one aspect, the decoy polynucleotide may comprise a cholesterol modification at one or at each 5' end of the molecule.

The decoy polynucleotide may comprise any one or more of the above features in any suitable combination.

When introduced into a suitable host cell, a decoy sequence in a decoy polynucleotide is able to compete with a cis-regulatory sequence in the cell for binding of the transcription factor which binds to the endogenous cis-regulatory sequence. Sequences can be screened for this function by the methods described herein. The cis regulatory sequence with which the decoy sequence competes may be any of the cis-regulatory sequences described herein and/or identified according to the methods herein.

For example, the cis-regulatory sequence may be one which regulates expression of a gene or genes which have a role in metabolite production, e.g. where the metabolite is an antibiotic (e.g. actinorhodin, undecylprodigiosin or cinnamycin), enzyme or pharmaceutical. Metabolite production may be increased in the cell.

The cis-regulatory sequence may be one which regulates expression of a gene or genes which have a role in determining antibiotic resistance. Antibiotic resistance in the cell may be decreased. The cis-regulatory sequence may be one which regulates expression of a gene or genes which have a role in determining solvent (e.g. butanol) tolerance. Solvent tolerance in the cell may be increased.

For example, the cis regulatory sequence may comprise sequence encoding a binding site for AfsR protein (a pleitropic regulator of antibiotic synthesis in *S. coelicolor*). An AfsrR binding site is shown in bold in SEQ ID NO: 1 (Example 1).

In another example a cis-regulatory sequence may be one in the *S. coelicolor* actII-orf4 promoter, for example a repressor cis-regulatory sequence. For example a cis-regulatory sequence may comprise sequence A24.1, A24.2, A24.3, A24.4. or A24.5 identified herein.

In a further example, a cis-regulatory sequence may comprise a binding site for the VanR transcription factor, for example, a VanR binding site located in the vanH promoter of, for example, *Entercoccus faecium* or *S. coelicolor*. An example of a 30 bp VanR binding site is shown in SEQ ID NO: 21 and a further example is in SEQ ID NO:26.

A cis-regulatory sequence may be one which functions to regulate expression of a gene or genes encoding a particular function or phenotype of interest, e.g. production of a metabolite(s) such as an antibiotic (e.g. cinnamycin, actinorhodin, undecylprodigiosin), tolerance to a particular solvent(s) or toxin(s), resistance to a particular antibiotic(s), or any other function or phenotype of interest. Typically the sequence will be located in the promoter region of such gene(s).

For example, a cis-regulatory sequence may regulate expression of cinnamycin biosynthetic genes in *S. cinnamoneus*, e.g. a cis-regulatory sequence from the cin7 promoter.

A cis-regulatory sequence may regulate expression of a gene(s) encoding solvent tolerance, e.g. in a prokaryote, e.g. butanol tolerance in *E. coli* K12.

A cis-regulatory sequence may be one which regulates expression of prokaryotic antibiotic resistance gene(s), typically a cis-regulatory sequence from the promoter of a gene(s) encoding antibiotic resistance. Any antibiotic resistance of interest may be targeted. For example, antibiotic resistance to: the class of antibiotics known as aminoglycosides (such a kanamycin); the carbapenems (such as meropenem); the cephalosporins (such as cefepime); the glycopeptides (such as vancomycin and daptomycin); the penicillins such an ampicillin, carbenicillin and penicillin); the polypeptide antibiotics (such as polymixcin B); the quinolines (such a levaquin); the sulfonamides (such a Bactrim); the tetracyclines (such as tetracycline); and variously, chloramphenicol, rifampicin and Zyvox.

In one aspect, a gene or genes encoding resistance to an antibiotic encode proteins which provide resistance to a specific antibiotic or, in some cases, a class of antibiotic, such as the antibiotics and classes listed above. Such antibiotic resistance genes may encode proteins which target a specific mechanism or structure of the antibiotic or class of antibiotics. Often such resistance genes are acquired by a bacterium after exposure to the antibiotic.

In one aspect, antibiotic resistance genes may include one or more of the following genes or types of genes:

The vanHAX operon genes, regulated by the VanR transcription factor, which occur in a number of bacteria including *Enterococcus* (e.g. *E. faecalis*, *E. faecium*), *Staphylococcus* (e.g. *S. aureus*) (Courvalin (2006) Clin. Infect. Dis. 42, S25) and has been reported as rare occurrences in other pathogenic bacteria (Werner (2008) Future Microbiol. 3, 547). These genes when expressed provide VanA type resistance to the antibiotic vancomycin. A decoy sequence targeting the vanHAX genes comprises a native VanR binding site (such as that in SEQ ID NO: 21 or SEQ ID NO: 26) or a variant of a native site, which competes with the native site for VanR binding in the cell of interest.

Those genes encoding beta-lactamases, which cause resistance to the beta-lactam class of antibiotics (in particular the penicillins, cephalosporins, cephamycins and carabapenems). These genes are of particular medical importance in Gram-negative infections which contain a sub-class of beta-lactamases known as the extended-spectrum-beta-lactamases (ESBLs), which are manifest in bacteria including *C. freundi, P. aeruginosa* and increasingly *K. pneumonia, E. coli* and *Salmonella* spp. A survey of the currently found beta-lactamases can be found in Paterson (2005) Clin. Microbiol. Rev. 18, 657.

The main types of beta-lactamases, an example of an organism and the antibiotics they effect and the gene responsible are as follows: TEM beta-lactamases, most commonly by the TEM-1 gene affecting ampicillin resistance in most Gram-negatives, including *E. coli, K. pneumoniae, H. influenzae* and *N. gonorrhoeae*, though in excess of 140 TEM-type enzymes have been identified (George (2005) N. Eng. J. Med. 352, 380); SHV beta-lactamases, most commonly SHV-5 and SHV-12 which cause, for example, ampicillin resistance in *K. pneumoniae* (Paterson (2003) Antimicrob. Agents Chemother. 47: 3554); CTX-M beta-lactamases, causing, for example, resistance to cefotaximine and other oxyimino-beta-lactamases (such as ceftazidime, ceftriaxone or cefepime) in *E. coli* and *S. enterica,* 40 CTX-M enzymes have been described (Canton (2008) Clin. Microbiol. Inf. 14: 134); OXA beta-lactamases, causing, for example, resistance to oxacillin and cloxacillin in Enterobacteria, such as *E. coli* and *K. pneumoniae* and *P. aeruginosa*; inhibitor-resistant beta-lactamases, such as variants of TEM-beta-lactamases found, for example, in *E. coli* and *K. pneumoniae*, which are resistant to calvulinic acid and other inhibitors; AmpC-beta-lactamases found in many Gram-negative bacteria including *Enterobacter* species that give broad-spectrum resistance to cephalosporins; carbapenemases that encode resistance to cephamycins, cephalosporins and carbapenems, this type of beta-lactamase can be divided into IMP-type (present in Gram-negative bacteria, particularly *Pseudomonas* and *Acinetobacter*), VIM (an example being the dominant variant being VIM-2 found predominantly in *P. aeruginosa* and encoding resistance to all beta-lactams with the exception of the monobactams) and KPC (encoding carbapenem resistance in *K. pneumoniae*).

Those genes encoding efflux pumps which actively extrude antibiotics from the bacteria, of which there are five major superfamilies (Poole (2007) Ann. Med. 39: 162): major facilitator (MFS), ATP-binding cassette (ABC), small multidrug resistance (SMR), resistance nodulation (RND) and multidrug and toxic compound extrusion (MATE). Those antibiotics affected by each of these efflux system, the genes responsible and the organisms in which they most commonly occur are given in Table 1 of Poole (2005) J. Antimicrobial Chemother. 56, 20 and shown in FIG. 27. Medically important resistance genes include: Macrolide resistance is commonly encoded for by the Mef(A) gene, for example in Streptococci (Pozzi (2004) Curr. Drug Targets Infect. Disord. 4, 203) and Gram-Negative bacteria; MsrD encodes ketolides resistance, for example in *S. pneumoniae* (Daly (2004) J. Clin. Microbiol. 42: 3570); chloramphenicol resistance is encoded, for example, by the Cml/CmlAB efflux system, as described in *P. aeruginosa, K. pneumoniae* and *S. enterica* (Schwarz (2004) FEMS Microbiol. Rev. 28: 519); erythromycin resistance is encoded by MexCD-OprJ in *Pseudomonas* spp. (Tauch (2003) Mol. Genet. Genomics 268: 570); tetracycline resistances are encoded by the Tet family—commonly TetA, TetB, TetC, TetD, TetE, Tet30 and Tet39 in Gram-negative bacteria (Roberts (1996) FEMS Microbiol. Lett. 19: 1 and Butaye (2003) Int. J. Antimicrob. Agents 22: 205) and TetK and TetL in Gram-positive (Butaye (2003) Int. J. Antimicrob. Agents 22: 205); beta-lactam and aminoglycoside resistance in *H. influenzae* is encoded for by AcrAB-TolC (Rosenberg (2000) J. Bac. 182: 1754). Efflux pumps from the MATE superfamily confers resistance to fluoroquinolines amongst others, and those genes responsible have been identified in *E. coli* (NorE, Morita [1998] Antimicrob. Agents Chemother. 42: 1178), *N. gonorrhoaea* (NorM, Roquette-Loughlin [2003] J. Bac 185: 1101), *H. influenzae* (HmrM, Xu [2003] Microbiol. Immunol. 47: 937), *P. aeruginosa* (PmpM, He J. Bac. 186: 262), *C. difficile* (CdeA, Kaatz [2005] Antimicrob. Agents Ther. 49: 1857), *S. aureus* (MepA, Kaatz [2005] Antimicrob. Agents Ther. 49: 1857) and *E. coli* (AcrAB, Nishino [2001] J. Bac. 183: 5803).

Those genes encoding resistance to aminoglycosides (such as streptomycin, kanamycin, tobramycin, amikacin). Resistance is commonly encoded by genes which produce enzymes that modify the antibiotics most commonly by N-acetylation (aminoglycoside acetyltransferases, AAC), adenylylation (aminoglycoside nucleotidyltransferases, ANT) or O-phosphorylation (Aminoglycoside phosphotransferases, APH) (Shakil [2008] J. Biomedical Sci. 15: 5). Examples of such genes are found in both Gram-negative and Gram-positive bacteria: AAC(6')-Ie APH(2")-Ia confers broad spectrum aminoglycoside resistance in enterococci and staphylococci (Hedge [2001] J. Biol. Chem. 276: 45876); the AAC(3) family is the largest (Sunada [2003] J. Antibiot. (Tokyo) 52: 809) and, for example, confers broad resistance to aminoglycosides in enterococci (Draker [2004] Biochem. 43: 446); ant(2") and ant(4") genes encode resistance to gentamicin and tobramycin in gram-negative bacteria whilst ant(4') and ant(6) and ant(9) do so in Gram-positive bacteria (Jana [2006] Appl. Microbiol. Biotechnol. 70: 140); in Gram-positive organisms the aph(3') gene is widely spread and confers resistance to a broad range of aminoglycosides, especially in staphylococci and enterococci (McKay [1996] Antimicrob. Agents. Chemother. 40: 2648).

Additionally the ermB gene is implicated in determining resistance to erythromycins, such as Zithromax/Azithromycin, particularly in Streptococcal infections (Richter [2005] Clin. Infect. Dis. 41: 599).

In one aspect, the present methods may be used to target regulation of expression of any one or more of the above resistance genes or types of genes, e.g. genes encoding beta-lactamases, genes encoding aminoglycoside modifying enzymes, to thereby alter resistance to the corresponding antibiotic(s), e.g. in a bacterial strain listed above. Decoy sequences for targeting regulation of a gene(s) may be identified and tested as described herein.

A decoy sequence may comprise a cis-regulatory sequence itself or, for example, a variant or fragment thereof which retains the necessary competing function. The cis-regulatory sequence may comprise any of those described herein and/or identified according to any of the methods described herein. A decoy sequence may comprise a snare sequence as described herein and/or as identified herein, or a variant or fragment thereof which retains the necessary competing function.

A decoy sequence for targeting a specific set of genes, e.g. antibiotic resistance genes, may be prepared based on the native transcription factor binding site in a cell. For example, sequences are available in published literature. In one aspect, a test decoy sequence may comprise an endogeneous binding site or a consensus sequence or a variant or fragment of a native site.

A test decoy sequence can then be assessed for decoy function. Typically, the decoy sequence is prepared as a decoy polynucleotide as described herein. The decoy polynucleotide is introduced into a host cell which comprises a binding site for the given transcription factor, operably linked to a gene or genes, the expression of which can be detected directly or indirectly: For example, screening may comprise testing directly for expression of a regulated gene, or testing for a phenotype which is causally linked to expression of the gene. A decoy sequence which causes an alteration in the expression of the gene or genes is said to have decoy function.

Suitable methods for testing decoy function, e.g. using the n[snare] plasmids, reporter systems, are described herein.

Test decoy sequences can also be determined by the methods described herein using n[snare] plasmid libraries, and/or methods for identifying boundaries of protein binding sites. These methods can be used to examine the genetic basis for phenotype in cells. For example, to examine the genetic basis for antibiotic resistance in a clinical isolate.

A decoy polynucleotide may comprise any of the decoy sequences described herein and may also comprise additional sequence as described.

A decoy polynucleotide may comprise any of the decoy sequences and/or decoy polynucleotides described in the Examples. Thus, for example, a decoy polynucleotide comprising the AfsR binding site may comprise an n[snare] plasmid of Example 1 or the snare comprised therein, or the oligonucleotide of SEQ ID No. 3 which forms a cyclised decoy dumbbell decoy structure. A decoy polynucleotide may comprise an n[snare] plasmid identified as causing an upregulation in cinnamycin production in Example 2 or 3, or a snare comprised therein. A decoy polynucleotide may comprise an n[snare] plasmid identified as causing an increase in butanol tolerance in Example 4, or a snare comprised therein. A decoy polynucleotide may comprise any of SEQ ID No. 8, 9, 10, 11 or 12 as described in Example 5. A decoy polynucleotide may comprise the oligonucleotide of SEQ ID No. 21 which forms a circular dumbbell decoy, or SEQ ID NO:26, or a species variant of the VanR binding site.

Decoy polynucleotides may be prepared by any suitable method. For example, dumbbell decoys may be prepared by PCR using appropriate primers, as described in Example 7.2. Each primer generally contains a portion which will form the stem loop of the dumbbell structure. Examples of such primers are given in SEQ ID NOS: 24 and 25. PCR amplification using the primers is typically followed by restriction digest of the amplification product and ligation to form the closed circle dumbbell.

Alternatively, dumbbells can be prepared by restriction digest of a plasmid as described in Example 7.3. Digestion is followed by ligation to form the closed circle dumbbell structure.

The present methods may be used to alter gene expression in prokaryotic or eukaryotic cells. In one aspect, when the method is applied in eukaryotic cells, the decoy polynucleotide comprises an n[snare] plasmid as described herein and/or the decoy sequence competes with a cis-regulatory sequence identified according to the methods described herein and/or the decoy sequence comprises a cis-regulatory sequence identified according to the methods described herein or a variant or fragment thereof.

A decoy polynucleotide may be introduced to a host cell by any suitable means. For example, transformation, transfection, conjugation. For example, where the polynucleotide comprises a conjugative plasmid, this may be introduced by conjugation. Decoy polynucleotides, e.g. circular dumbbell structures, may be introduced to cells by transfection. Cells may be in liquid culture and the decoy added to the liquid. Alternatively, cells may be cultured on solid media and decoys transfected from absorbent paper discs saturated with decoy and overlaid on the media. Typically, decoy polynucleotide is added to the culture medium and taken up by cells. Where cells are cultured on solid media, decoy polynucleotides may be added to a filter disc and taken up by cells from the disc. A permeability buffer may be used to aid transfection.

In one aspect, transfection of decoy polynucleotides may comprise the use of cholesterol. In particular, the methods may use linear decoy polynucleotides, bearing a cholesterol modification at one or both 5' ends. The modification is believed to facilitate uptake by the cells.

Decoys may additionally be labelled, e.g. at a 5' end with a detectable label such as a fluorescence dye, e.g. Cy5. This will facilitate monitoring of uptake and maintenance in the cell.

Cholesterol and/or detectably labelled decoys may be prepared using cholesterol and/or detectable labelled primers, as described in Example 7.1.

Transfection of decoy polynucleotide into a cell may comprise use of R9-cholesterol, which consists of a cholesterol molecule attached to a linear chain of nine D-arginines (Kim W. J., et al., Mol. Ther. 2006 14: 343-350).

In general, the uptake and/or maintenance of the decoy polynucleotides in the cells is monitored. For example, a plasmid decoy may comprise a detectable marker e.g. encoding antibiotic resistance, which allows positive selection for the presence of the plasmid and monitoring of plasmid propagation. Presence of a decoy polynucleotide can also be monitored by qrt-PCR.

In general, the cells into which the decoy is introduced are those which comprise the cis-regulatory sequence (typically the promoter containing the sequence) with which the decoy competes for transcription factor binding, operably linked to the gene(s) whose expression is to be modulated. Suitable host cells are described herein. Typically, where the method is used to alter a cell phenotype, the host cells display the phenotype in the absence of the decoy. Decoys for alteration of a medically or therapeutically relevant phenotype, e.g for increasing antibiotic sensitivity, may be screened in a series of cells. For example, decoys may be tested first in a bacterial model of the phenotype, e.g. a model of antibiotic resistance, then further validated in e.g. a pathogen or clinical isolate. Decoys may be further validated in an animal model, as described herein.

Once the decoy polynucleotide has been introduced into the cells, typically the cells are screened for modulation of gene expression. Screening may be direct or indirect. Methods of screening for modulation of gene expression and/or phenotype in cells are described herein in relation to methods for identifying cis-regulatory sequences.

In a further aspect, more than one decoy polynucleotide may be introduced into a cell to alter phenotype. For example, a combination of n[snare] plasmids may be used, provided that the plasmids are compatible.

In one aspect, the methods described herein are in vitro methods.

The methods for modulating phenotype described herein have a number of applications, for example, in industry and in therapeutics.

The methods may be used to alter phenotype in industrially important cells, for example, to increase the production of useful metabolites. Accordingly, in one aspect the invention provides a method of modulating (increasing or decreasing) production of a metabolite in a cell comprising a method described herein. Typically, in the methods the cis-regulatory sequence of interest regulates expression of a gene(s) encoding protein(s) necessary for production of a metabolite.

In one aspect the cis-regulatory sequence comprises one of A24.1, A24.2, A24.3, A24.4. or A24.5 identified herein. The invention relates to a method of modulating antibiotic production comprising use of any of A24.1, A24.2, A24.3, A24.4. or A24.5 identified herein, e.g. A24.1. A24.3 A24.5, such as A24.5, or of decoy molecules which compete with any of the aforementioned for binding of transcription factor. The invention further relates to a method of modulating antibiotic production comprising use of any of SEQ ID NOS 8-12.

The methods may also be used to render cells, e.g. bacterial cells, more sensitive to antibiotics. Accordingly, the invention further provides a method for modulating (increasing or decreasing) antibiotic sensitivity of cells, e.g. bacterial cells comprising a method described herein. Typically, in the methods the cis-regulatory sequence of interest regulates expression of a gene(s) encoding protein(s) necessary for antibiotic resistance.

Thus in one aspect the invention provides the use of a decoy polynucleotide for modulating antibiotic resistance of a cell. In general the modulation is caused by an alteration in expression of antibiotic resistance gene or genes in the cell. The effect may be specific to a particular antibiotic or in some cases, class of antibiotics.

Generally, the cell comprises a gene or genes operably linked to a cis-regulatory sequence comprising a binding site for a transcription factor and the decoy polynucleotide comprises a decoy sequence with the same binding site or a site that competes with the cellular binding site for transcription factor binding. Introduction of the polynucleotide into the cell reduces binding of the transcription factor to the cis-regulatory sequence in the cell and causes an alteration in expression of the gene or genes in the cell, thereby modulating antibiotic resistance of the cell.

Typically the targeted cis-regulatory sequence in the cell regulates expression of an antibiotic resistance gene or genes as described herein. The decoy disrupts regulation of expression of the gene(s) and thereby causes an alteration (e.g. a decrease) in antibiotic resistance in the cell.

The cell may be a laboratory model of resistance or a native resistant strain, e.g. a pathogen or clinical isolate. Suitable cells are described herein.

In one aspect, the invention relates to a method for altering the phenotype of a prokaryote, other than the level of expression of $CO_2$-responsive genes in *Cyanobacterium*, which comprises providing a decoy comprising an excess of a nucleic acid encoding a sequence to which a prokaryotic transcription factor binds, wherein said sequence is identified according to a method described herein, such that upon contacting said decoy with said prokaryote, the transcription factor is competitively inhibited from binding to its cognate binding site in the genome of said prokaryote.

The invention may also relate to a method for altering the phenotype of a prokaryote, other than the level of expression of $CO_2$-responsive genes in *Cyanobacterium*, which comprises providing a decoy comprising an excess of a nucleic acid encoding a sequence to which a prokaryotic transcription factor binds, such that upon contacting said decoy with said prokaryote, the transcription factor is competitively inhibited from binding to its cognate binding site in the genome of said prokaryote. The decoy may comprises a portion of a promoter of a prokaryotic gene. The decoy may comprises a transcription factor binding site from the promoter of a prokaryotic gene, e.g. an antibiotic synthetic or regulatory gene. Binding of the decoy to the transcription factor may results in susceptibility of the prokaryote to an antibiotic to which the prokaryote is otherwise resistant. For example, the prokaryote may be normally resistant to the antibiotic vancomycin but, in the presence of said decoy, the prokaryote is no longer resistant. The prokaryote may be a pathogen. Alternatively, binding of the decoy to the transcription factor results in increased production by the prokaryote of an antibiotic.

In one instance, when the phenotype to be altered according to the present methods is antibiotic resistance, a putative decoy sequence is tested first in a laboratory model cell or reporter cell as described herein. Candidate decoy sequences are then generally tested in a native resistant cell, e.g. a pathogen cell or a clinical isolate. In general, the method additionally comprises testing candidate decoy sequences in a suitable animal model. For example, a mouse model may be used. In general, the animal model is infected with a pathogenic strain that is resistant to treatment with antibiotics alone.

In some cases, when a decoy sequence (based on a binding site sequence in a model bacterial species) is tested against a panel of clinical isolates, it may be found that there are some isolates which are refractive to the treatment. In such cases those isolates may be identified and sequence analysis performed to determine if there are any variations within the regulatory sequence the TFD mimics. If so the occurrence of those variations can be estimated and a cocktail of the TFD created that contains both model and variant sequences in rough proportion to their incidence in the clinic.

The present decoy polynucleotides have a number of applications, including medical and veterinary applications, as well as in vitro uses.

For example, decoy polynucleotides which increase cell susceptibility to one or more antibiotics can be used to treat bacterial infections in humans or animals, or in ex vivo methods for killing or inhibiting prokaryotes, e.g in antibacterial cleaning compositions.

Typically in use, a decoy will be used in combination with the antibiotic(s) which it makes the cell more sensitive to. The antibiotic may be administered simultaneously with, or before or after the decoy. The antibiotic and decoy may be administered in the same or in separate compositions.

Thus, for example, a decoy which targets VanR regulation of the vanHAX operon to lower resistance to vancoymcin will typically be used in combination with vancomycin antibiotic.

The particular infection or associated condition which the decoy is used to treat is in general dependent upon the pathogenic cell that the decoy targets.

For example, vancomycin resistant Enterococci (VRE) such as *E. faecium* and *E. faecalis* are associated with abdominal infections, skin infections, urinary tract infections, blood infections. Therefore a decoy targeting VanR regulation of vancomycin resistance genes in a VRE, may be used for treatment of such infections, typically in combination with vancoymcin.

For example, Gram-negative infections (such as *E. coli* and *K. pneumoniae*) carrying genes encoding for Extended-Spectrum beta-lactamases show broad resistance to penicillins are associated with serious infections of the urinary tract and gut. In one aspect, treatment with decoys designed to prevent or downregulate the expression of those genes encoding the beta-lactamases (such as the CTM-X family of genes) in combination with a penicillin may be used for treatment of such an infection.

In one aspect, Zithromax resistance, caused by expression of mefA or ermB genes in *S. aureus, S. pneumoniae* or *C. pneumoniae*, and evident in infections of the ear and throat could be treated by application of decoys targeting mefA and ermB regulation in such organisms, typically in combination with the antibiotic.

In one aspect. fluoroquinolone-resistant infections, such as *S. pneumonia*, causing pneumonia could be treated by decoys targeting norA (the gene encoding the efflux pump) regulation and administered in combination with the antibiotic.

In one aspect, macrolide-resistance, such as clarithromycins (for example Biaxin) in *C. pneumoniae* infections, causing pneumonia, could be treated by administration of the decoy targeting the regulation of the resistance gene ermB in combination with the antibiotic.

In one aspect, decoys targeting the ampC gene, that encodes resistance to beta-lactams (such as penicillin, for example, Augmentin), could be used as a therapy against a wide range of Gram-positive and Gram-negative nosocomial infections by injection with the antibiotic in a hospital setting.

In one aspect the invention relates to a pharmaceutical composition comprising a decoy polynucleotide and a physiologically acceptable carrier or excipient. The composition may additionally comprise one or more antibiotics as described.

Acceptable carriers or diluents for therapeutic use are well known in the pharmaceutical art, and are described, for example, in Remington' Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder, lubricant, suspending agent, coating agent, solubilising agent.

Decoys may be administered by any suitable means, for example by intravenous injection, topical application or oral delivery. As above, administration may be in combination with a suitable dose of antibiotic, with the antibiotic(s) being administered at the same time as the decoy, or separately.

Decoy polynucleotides which increase antibiotic resistance can also be used in cleaning compositions such as disinfectants, again typically in combination with the antibiotic(s) to which they make the cell more sensitive and/or in combination with one or more antibacterial agents. In one aspect the invention relates to such a cleaning composition.

The invention further provides a kit comprising a decoy polynucleotide as described herein and one or more antibiotics or antibacterial agents, wherein the decoy and the antibiotic(s) or antibacterial agent(s) are for combined used in killing or inhibiting prokaryotes such as bacteria.

In one aspect therefore the invention further relates to the use of a decoy polynucleotide as described and/or identified herein, for the manufacture of a medicament for treating bacterial infection in a subject. The invention further relates to the decoy polynucleotide for the treatment of bacterial infection and to a method for treating a subject for bacterial infection comprising administering the decoy polynucleotide as described herein.

The invention further relates to compositions and medicaments comprising a decoy polynucleotide as described and/or identified herein. Further aspects include combination therapies in which a decoy polynucleotide as identified, and/or as described herein, is administered to a subject in combination with one or more antibiotics or other antibacterial therapies.

In further aspects, the invention relates to cis-regulatory sequences identified according to the methods described herein, and to their use, e.g. in decoy sequences. In particular, the invention relates to cis-regulatory sequences identified in the present Examples, e.g. cis-regulatory sequences comprising A24.1, A24.2, A24.3, A24.4. or A24.5 identified herein and decoy polynucleotides comprising them. The invention further relates to decoy polynucleotides as described herein and/or as described herein, e.g. to SEQ ID NOS: 3, 8-12 and 21.

The invention further relates to any of the n[snare] plasmids, or plasmid libraries described herein and/or prepared according to the methods described herein, including those prepared in the present Examples.

The invention further relates to host cells comprising n[snare] plasmids and/or decoy polynucleotides as described herein. In particular the invention relates to such hosts which display altered gene expression and/or phenotypes. For example, the invention relates to host cells which display increased production of a given metabolite, e.g. antibiotic, increased susceptibility to antibiotic or increased tolerance to a given solvent, including those prepared in the present Examples.

Thus in one aspect the invention relates to host cells (such as those described herein) comprising a decoy polynucleotide as described herein, including n[snare] plasmids or plasmid libraries as described herein. Included particularly are those cells having altered susceptibility to antibiotics (e.g. increased susceptibility) and prepared according to the methods herein. Thus in one aspect the invention relates to pathogens or clinical isolates which have been rendered more susceptible to antibiotics using decoy polynucleotides as described herein.

Further Description of Specific Embodiments of the Invention

In a first embodiment according to this invention, we provide a generic method for identifying cis-regulatory elements. As with most good science, the Genome Sequencing projects posed more questions than they answered. Essentially what they delivered was a list of all the genes within an organism (the genome), but this raised the question of which of these were being used (expressed) at any one time, and under what conditions. This is an important consideration, as patterns of expression provide clues to the function of the genes and identify those responsible for important characteristics (phenotypes). Consider human cells: all contain the same genes, but the pattern of expression will depend upon (and possibly determine) whether that cell is from the liver or brain (tissue-specific regulation). Novel technologies have been developed (microarray technology) capable of describing the pattern of gene expression, and can, for example, identify sets of genes responsible for medically-important phenotypes, such as resistance to disease. One of the promises of the Genome Sequencing projects was that such knowledge will help speed the design of new drugs and strategies for treating disease. However new tools will be needed to realize this potential.

As we now have the ability to identify genes determining phenotypes, the next challenge becomes to gain control of these genes, and by so doing, gain control over phenotypic expression. This would be of fundamental importance, to our understanding of biology in general, the identification of novel targets for drugs, and also to allow us to improve production of medically and commercially important compounds from industrial bacteria, (e.g. so-called fermentation products). Fermentation products range from foods, medicines, and, increasingly, industrial enzymes and fuels. It is a worthy goal to derive these products from a sustainable source (bacteria) as opposed to relying on traditional and environmentally costly (petro)-chemical methods of manufacture.

Genes are turned on and off by specialist proteins, i.e., transcription factors. These have a dual function: they bind to specific DNA sequences (regulatory elements), usually close to a target gene, and they alter the likelihood of that gene being expressed. Earlier attempts focused on changing the properties or abundance of the transcription factors themselves. Our approach is to target the regulatory elements to which the transcription factor binds. One strategy we have developed is to introduce an excess of these regulatory elements (termed 'decoys'), so as to competitively prevent the transcription factor from binding to the genomic version and so block any influence on the downstream gene (see the discussion below pertaining to second and third embodiments according to this invention). In this embodiment of the invention, we build libraries of decoys, (containing either all the regulatory elements from a species, or a universal version with all possible regulatory elements) that can be rapidly tested to identify which sets of regulatory elements have the desired effect. A key part of the approach consists in building a generic 'reporter system', such that, instead of looking for changes in complex phenomena, such as increased yield from an industrial bacterium, successful modification rather is monitored by changes in expression of an introduced reporter gene which confers resistance to antibiotics and which is easy to detect. The system is so designed that screening can be performed at high-throughput. Thus, this aspect of the invention represents a technology born of the genomic age where it must be possible to produce high quality data at speed and relevant to the entire genome. The mixture of a universal decoy library and a generic reporter system is anticipated to rapidly improve the delivery of biotechnology products and be an invaluable research tool.

More specifically, according to this embodiment of the invention, we have adapted the 'decoy' oligonucleotide approach to control genetic regulation in a prokaryote and effect control of antibiotic production in *Streptomyces coelicolor*. Decoys, however, are sensitive to degradation, and the approach is not amenable to high-throughput. We address both of these issues in the method according to this invention, (see Examples 1-4). Generally, using Rolling Circle-Mechanism of DNA amplification, an oligonucleotide was converted into a series of (about thirty) double-stranded direct repeats. These were cloned into a high-copy shuttle vector (capable of propagation in both *E. coli* and *Streptomyces*) and introduced into *S. coelicolor* by conjugation. The plasmid was maintained by antibiotic selection. We have found that this system performed better than decoys: there was greater repression of antibiotic production and it persisted for the length of the experiment. The method of constructing the library has been adapted so that generic libraries can be made from synthetic random oligonucleotides, or species-specific libraries made from fragments of the entire genome. To create a universal screening system, reporters for negative and positive selection are created in the common host for heterologous expression, *Streptomyces lividans*. The targeted promoter is cloned upstream of a kanamycin resistance gene or glkA, which determines sensitivity to the metabolite 2-deoxyglucose (DOG). Following transformation of a library the transformants are screened in liquid culture for increased tolerance of kanamycin (detecting negative regulation) or increased sensitivity to DOG (detecting positive). As selection is in liquid culture, the vast majority of clones are lost, leaving only a small and manageable number to take forward for analysis. A validation system is developed where sets of colonies from independent screens are tested to see which cross-hybridize with members of other sets. In this way it is possible to identify clones that recur in the library and are good candidates for sequence analysis.

In a second embodiment according to this invention, (see Example 5), we used decoy oligonucleotides to study the regulation of the blue-pigmented antibiotic actinorhodin in *Streptomyces coelicolor* A3(2). This organism contains (for a prokaryote) a relatively large genome (8.7 Mb) with a complex and adaptive pattern of gene regulation, particularly with respect to the developmental and environmental cues that control antibiotic production (Bibb (2005) *Curr. Opin. Microbiol.* 8: 205-215). *S. coelicolor* is also the model organism for the actinomycetes, and increasing the level of understanding of the regulation of antibiotic production in this strain may inform new strategies for gaining access to the wide variety of secondary metabolites produced by these organisms. Many of these compounds have important applications in medicine, for example as antibiotics, and in agriculture (Berdy (2005) *J. Antibiot.* 58: 1-26), and actinomycetes continue to be a profitable source of new drugs and enzymes (Ward (2006) *Curr. Opin. Microbiol.* 9: 279-286).

Perhaps as a consequence of the complex regulation of antibiotic production, many pleiotropic mutants identified by genetic screens are conditional; for example, the antibiotic non-producing phenotype of a relA null-mutant is highly medium-dependent (Chakraburtty (1997) *J. Bacteriol* 179:5854-5861). The occurrence of nutritionally conditional phenotypes implies that genetic screens may underestimate the number of regulatory factors influencing antibiotic production. Inactivation of a bona fide transcription factor may be missed if, under the conditions used, activation of target genes can be mediated by an alternative transcription factor or regulatory pathway. One of the advantages of decoys is that they identify and manipulate the sequence component of DNA-protein interactions controlling gene expression, potentially blocking the interaction of numerous transcription factors with a single site. In this embodiment according to the invention (see Example 5), we demonstrate the relative ease of targeting regulatory sequences and the ability to rapidly identify novel regulatory genes in a manner that is complementary to conventional genetic screens.

In a third embodiment according to this invention, (see Example 6), we demonstrate the utility of decoy oligodeoxynucleotides to confer sensitivity to an antibiotic on a bacterium that is otherwise resistant to that antibiotic. Those skilled in the art will appreciate the extreme significance of this aspect of the invention in an age where so-called "superbugs" are to be found everywhere, including in our hospitals. Frequently attributed to the widespread use of antibiotics, the development of these so-called superbugs has the potential for generating pandemic infections. By means of this aspect of the invention, however, those skilled in the art will appreciate that by properly understanding the mechanisms by which pathogens achieve resistance to specific antibiotics, decoy oligonucleotides identified according to the methods of this invention may be used prior to, at the same time as, or both prior to and at the same time as administration of the particular antibiotic.

Many genes are controlled at multiple levels through the interaction of regulatory factors with cis-regulatory sites. The nucleoprotein complexes formed may do so in a tissue-specific, developmental stage-specific, or stimulus-dependent manner. In short, in vivo DNA-protein interactions are physiologically determined and represent the interaction between two dynamic components: the DNA-binding proteins that constitute the trans-acting environment, and the cis-regulatory sequences. While our knowledge of the patterns of gene expression has grown substantially in recent years, this growth has not been paralleled by a comparable increase in our knowledge of regulatory factors that control specific genes affecting specific cellular processes. We anticipate that application of the techniques herein is likely to give fresh insights into the complexities of prokaryotic genetic regulation and establish them as a complementary approach to conventional genetic analysis.

All documents referred to herein are hereby incorporated by reference.

EXAMPLES

Having generally described this invention, including its preferred embodiments and best mode, the following specific examples are provided, together with further description, to fully enable and extend the written description of this invention. Those skilled in the art will appreciate, however, that this invention should not be construed to be limited to the specifics of the Examples. Rather, for purposes of apprehending the scope of this invention, reference should be made to the claims appended to this disclosure, including equivalents thereof.

Although in general many of the techniques mentioned herein are well known in the art, reference may be made in particular to Sambrook et al, 1989, Molecular Cloning: a laboratory manual.

Example 1

Demonstrating the Creation of Plasmid-Borne Versions of Decoy Oligonucleotides and their Utility in Modifying Phenotypes To achieve this work, it was first necessary to develop a molecular biology protocol capable of creating an n[snare] plasmid. A desired feature of such a plasmid vector is that it should contain a section consisting of direct copies of the same fragment of DNA. Usually these copies number 30, but may range in number from one to a thousand, and the length of the repeated sequence is in the range of 35-54 bp, but can be longer, e.g., up to 1000 bp. In the example of construction given below, within this repeated sequence, there is a segment (27 bp) which is common to all n[snare] plasmids and is a consequence of the method of manufacture. Also in this example the plasmid vector was chosen: (i) to allow transformation and propagation of *E. coli* and *S. coelicolor*; (ii) to contain a selectable marker gene encoding resistance to the antibiotic apramycin; and (iii) to maintain a high-copy number within the cell, typically approaching 100 copies per cell.

Method to Create n[Snare] Plasmid Containing the AfsR Binding Site

An overview of the process is given in FIG. 1. Single-stranded oligonucleotides are synthesized with a chimeric structure: (A) an annealing site for the T7 primer, and (B) a region containing the sequence of the cis-regulatory or putative cis-regulatory sequence. The oligonucleotide is circularized by the action of Taq ligase, in the presence of a universal joining oligonucleotide. Following digestion with exonuclease to digest linear DNA, monomeric circles are recovered from a preparative acrylamide gel. These are subsequently used as templates in a Rolling Circle Mechanism amplification reaction using Bst polymerase and the T7 primer. The same primer is used again in a PCR reaction and the products separated on an agarose gel. High molecular weight fragments, typically containing 30-50 repeats, are isolated and are cloned into a PCR vector before subcloning into a high-copy shuttle vector, to form an n[snare] plasmid. To determine function, the n[snare] plasmid is transformed either into the native strain or into a generic reporter strain. This protocol can also be used to produce 'generic' n[snare] libraries, made from random oligonucleotides, or species-specific libraries, from fragmented genomes. An illustration of how n[snare] plasmids affect expression of targeted genes is given in FIG. 2. In the top left of this figure, a gene (represented by a horizontal bar "A") is transcriptionally inactive due to the binding of a repressive transcription factor (circles "B") to a cis-regulatory sequence (horizontal bar "C") within the promoter of the gene. The sequence of the cis-regulatory sequence that constitutes the binding site for the transcription factor may be determined by various techniques including bioinformatic analysis, 'footprinting' of the promoter or the various n[snare] methods described herein. This sequence is incorporated into a decoy oligonucleotide to affect the expression of the gene, but is shown here cloned into a selectable plasmid in numerous (typically 30) direct repeats, to create an n[snare] plasmid. The plasmid is usually a 'shuttle' plasmid, meaning it can be propagated both in *E. coli* (for ease of genetic manipulation) and the targeted organism; in addition the plasmid is usually 'high copy', typically meaning it will produce approaching 100 copies of itself into the host cell. The n[snare] plasmid is introduced into the targeted prokaryote, by standard means, and its stable propagation is ensured by selecting for its marker, usually a gene encoding resistance to an antibiotic.

When thus introduced into a cell the n[snare] plasmid is able to affect expression of the targeted gene by titrating off the transcription factor "B" from the genomic promoter to relieve transcriptional repression of the downstream gene (shown as horizontal box "D", top right).

A decoy oligonucleotide containing the AfsR binding site was synthesized. It had the following sequence:

SEQ. ID. 1
5'-Phosphate- aat acg act cac tat agg ggc gtt gag cga acg ttt ttc gcg gcc gc- 3' where the AfsR binding site is shown by the sequence in bold and a restriction site for NotI is underlined. The oligonucleotide is synthesized with a phosphate group at the 5' end.

Also synthesized was a 'joining' nucleotide, R-T7, so called as it contains a partial complement of a commonly used primer, T7:

5'- ccc tat agt gag tcg tat tgc gg -3'    SEQ. ID. 2

Both primers were resuspended at final concentrations of 250 pmol/µl in a reaction buffer consisting of 1× Taq ligase buffer (as supplied by the manufacturers, New England Biolabs) and 50 U Taq ligase. The mixture was heated to 95° C. for 10 minutes before being allowed to cool to 45° C., upon which the reaction was supplemented with 4 U/ml Taq ligase and the reaction incubated overnight at 45° C.

1 µl of the reaction was used as a template for rolling circle amplification (RCA) in an incubation mixture consisting of 1× Thermopol reaction buffer (as supplied by the manufacturers, New England Biolabs), supplemented with 0.2 mM dNTPs, 70 nM T7 primer (the complement to R-T7) and 120 U/µl of Bst polymerase (New England Biolabs). The mixture was incubated overnight at 60° C.

The amplified DNA was recovered following a clean-up step on a commercially available column system, (Qiagen PCR Purification kit), and 1 µl of this DNA was used in a standard PCR reaction consisting of 1× Taq polymerase buffer (supplied by the manufacturers, Roche Diagnostics) supplemented with 0.2 mM dNTPs, 5% DMSO, 25 pmol T7 primer and 0.5 U Taq polymerase (Roche Diagnostics). PCR was performed using the following cycling parameters: 95° C. for 5 min, then 25 repeats of the following sequence: 93° C. 15 s, 55° C. for 15 s, 72° C. for 2 min, followed by 72° C. for 2 min.

The products of the reaction were analyzed by 1% agarose/TBE gel electrophoresis and visualized by trans-illumination of the ethidium bromide stained gel.

A successful preparation appears as a 'ladder' of sequences with a repeat length of approximately 50 bp and with sufficient amount of the material migrating with an apparent size of 1.5 kb to allow purification (equivalent to approximately 30 repeats of the 50 bp monomer).

In general, when carrying out this procedure, if the size of the products are predominantly small (less than 500 bp in size) then the amplifications are initially repeated varying the amounts of templates used, and in the PCR reaction, the number of cycles of amplification employed. In the event this fails to produce products of the desired size, an alternate strategy is followed where a NotI partial digest of product of Bst-amplification is performed, the fragments are size-fractionated to isolate a 1.5 kb template that is ligated to NotI compatible linkers in order to allow efficient amplification in a standard Ligation-Mediated PCR reaction (LM-PCR).

The 1.5 kb fragment is subcloned into the commercially available pGEMT-Easy vector from Promega, which is adapted with 3'T overhangs for efficient cloning of PCR products. Using standard molecular biology techniques the fragments are recovered following EcoRI digestion of DNA isolated from an aliquot of the pGEMT-Easy library and gel purified. The collection of EcoRI fragments are then subcloned into a similar restriction site in a shuttle vector, in our case pIJ86, which is capable of replicating in both *E. coli* and *S. coelicolor*. The pIJ86-borne n[snare] fragment is then introduced into *S. coelicolor* by conjugation using standard methods (Kieser et al. (2000) Practical *Streptomyces* Genetics. John Innes Foundation).

Use of the afsR n[Snare] Plasmid to Alter the Antibiotic Production Phenotype in *S. coelicolor*

Figure 3:
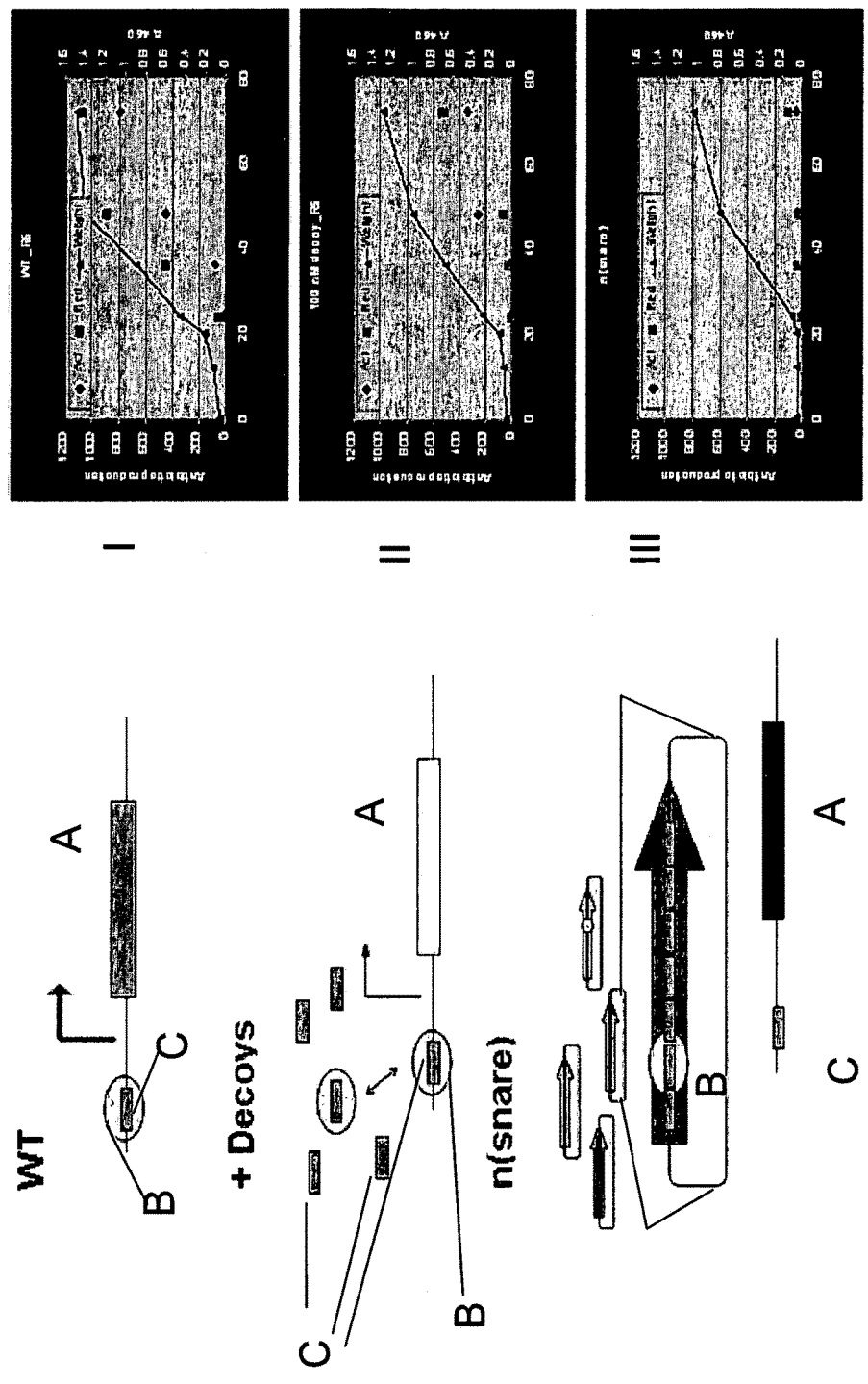
FIG. 3. Demonstration of n[snare] approach. n[snare] plasmids are capable of modifying control of gene expression in a predictable way with a concomitant change in phenotype. These plasmids are cheaper to produce and easier to transform into the cells than decoys, give a more sustained effect and crucially, they allow a library approach to discovering key regulatory elements.

AfsR is a pleiotropic regulator of antibiotic production in *S. coelicolor* and engineered deletions of this gene have shown that it is essential for the production of the two pigmented antibiotics, actinorhodin (which is blue) and undecylprodigisin (which is red) in *S. coelicolor* (Hong et al. (1991) J. Bacteriology 173: 2311-2318). A key cis-regulatory sequence that acts as a binding site for AfsR is found upstream of the afsS gene (Lee et al. (2002) *Molecular Microbiology* 43: 1413-1430), and it was this sequence that was used to test the n[snare] plasmid. It was reasoned that a decoy (made in parallel for comparison sake) or an n[snare] plasmid containing this site would be expected to inhibit expression of afsS by titrating off the activating AfsR protein from the promoter, with a resultant decrease in production of both of the pigmented antibiotics. Hence, three growth curves were monitored for untreated *S. coelicolor* that would serve as a control, a culture treated with a cyclized TFD containing the AfsR site (as described above and shown in bold, using the oligonucleotide: 5'-Phosphate-ata gcg ttg agc gaa cgt ttt tc gcg tttt cgc ga aaa acg ttc get caa cgc tat ag tttt ct-3' SEQ ID. 3) and a strain transformed with the AfsR n[snare] plasmid (FIG. 3). In this figure the wild-type promoter of afsS is shown top left "A", AfsR (oval "B") binds to its cognate site (rectangle "C") to activate expression of the regulatory gene. The graph "I" in the top right shows the growth curve of the culture and production of the two pigmented antibiotics, actinorhodin (Act) and undecylprodigiosin (Red); (the left ordinate=antibiotic production, the right ordinate=bacterial growth, the solid line shows bacterial dry weight measurements, diamonds represent actinorhodin (Act) production and squares represent undecylprodigiosin (Red) production). The graph "II" shows introduction of a circular dumb-bell decoy (+Decoys; middle left) which provide competition for AfsR binding, repressing expression of the regulator encoded by afsS, with a concomitant decrease in antibiotic production (middle right graph II). n[snare] plasmids containing homopolymeric repeats of the cis-regulatory sequence "C" (bottom left) prove more effective in suppressing antibiotic production (n[snare]) likely due to positive selection for the plasmid, and the repressive effect is observed through the course of the experiment (graph III bottom right). n[snare] plasmids are capable of modifying control of gene expression in a predictable way with a concomitant change in phenotype. These plasmids are cheaper to produce and easier to introduce into the cells than decoys, give a more sustained effect and, crucially, they allow a library approach to discovering key regulatory elements.

Hence, what was concluded was that, compared to the control culture (FIG. 3, top row), antibiotic production is suppressed in both decoy- and n[snare]-treated cultures. However, with the decoy-treatment, the effect is largely transient with antibiotic production recovering after 48 h, whereas with the n[snare] treatment, the suppressive effect persisted beyond the course of the experiment. Control experiments using scrambled versions of the AfsR-binding sequence either in the decoy format or incorporated into an n[snare] plasmid failed to significantly suppress antibiotic production. These observations support the conjecture that n[snare] plasmids can be used to identify and characterize cis-regulatory sequences, and in some respects (stability and extent to which the phenotype is modified) they are better than the extant technique of decoy oligonucleotides.

Example 2

A Method for Identifying Cis-Regulatory Elements and, Therefore, Decoys for Modifying Phenotype in Prokaryotes or Eukaryotes, Using n[Snare] Libraries In this example the n[snare] library is made from short DNA fragments isolated from the 17.083 kb cinnamycin biosynthetic cluster (Widdick and Bibb (2003) *Proc. Natl. Acad. Sci. USA* 100: 4316-4321), and the library reintroduced into the producing strain of *Streptomyces cinnamoneus*. Detection of the antibiotic is performed using a plate assay where colonies of the producing strain are allowed to grow on an agar plate which is overlaid with a soft nutrient agar seeded with an inoculum of the reporter strain *Bacillus subtilis*. A halo of clear nutrient agar appears around the producer colonies where the antibiotic has killed the indicator strain where elsewhere the nutrient agar appears turbid due to the strain's continuing growth. The diameter of the halo is an indicator of the amount of cinnamycin produced and, following introduction of the n[snare] library, can be used as a convenient screen for over-producing exconjugant colonies. In this way it is possible to determine whether members of the library can upregulate production of the antibiotic and confirms utility of the approach as a discovery tool to scan sizeable genomic fragments for candidate cis-regulatory elements that can be incorporated into TFDs. The logic of the approach can be expanded to develop strategies for n[snare] libraries to detect candidate sequences in much larger surveys (including entire genomes) and demonstrations of these approaches and their potential utilities are discussed in later Examples. Those skilled in the art will appreciate, however, that the method is not limited to the specifics of this exemplification and other prokaryotic or eukaryotic phenotypes may be similarly explored using this methodology to achieve phenotypic alterations of essentially any trait of interest.

1. Construction of Custom n[Snare] Libraries

A schematic of the procedure to generate these fragments is shown in FIG. 4. n[snare] plasmid libraries are created from large pieces of DNA in such a fashion that every cis-regulatory sequence within that DNA should be represented in the library. It is shown in this figure that genomic DNA or fractions of genomes, such as biosynthetic clusters, are fragmented by sonication and the free ends repaired by treatment with Taq polymerase and dNTPs, to generate ends with a single dA overhang at the 3' end of the DNA. To these biotinylated linkers are ligated, containing restriction sites for Nt.BbvCI (dark box), MmeI (light box), and a complementary 5' dT overhang. Unligated adaptor is removed from the ligation mixture before the modified fragments are digested with MmeI, an enzyme which cuts 20/18 nucleotides downstream of its recognition site, allowing for the dT introduced in the overhang; the resultant molecules consist of the intact biotinylated adaptor plus a 19/17 nucleotide stretch of genomic DNA, which we refer to as the 'snare'. These molecules are captured onto a streptavidin-coated matrix and denatured to leave the top strand (containing the 19 nt stretch) attached to the beads. A further oligonucleotide is now annealed designed to recreate the Nt.BbvCI site, and this is subsequently digested with that enzyme to release a single stranded piece of DNA consisting of a portion of the adaptor plus the snare sequence. This is used in subsequent steps to create n[snare] libraries.

1.1 Preparation of DNA Fragments

A DNA fragment containing the approximately 17 kb of the cinnamycin biosynthetic cluster was isolated from the cosmid it had been previously cloned into. The fragment was gel purified and sonicated to an average length of 500 bp as judged by analyzing an aliquot of the DNA by electrophoresis on a TBE/agarose gel. Sonication produces a heterogeneous population of DNA terminating with 3' and 5' overhangs of varying lengths and blunted DNA where a double stranded break has occurred. In order to convert these to a homogenous population consisting of ends with a 3' dA overhang, the DNA was treated with Taq polymerase.

1.2 Creation of 'Snares' of 18 Nucleotide Length from a Genomic Fragment

The term 'snare' is used to refer to the short single stranded portion of DNA derived from the fragments of genomic sequence that are used to create the n[snare] plasmids.

Using standard methods a biotinylated adaptor, of the following sequence (where P stands for Phosphate), is prepared and ligated to the treated DNA fragments:

```
                                     Nt.BbvCI       MmeI
5'-Biotin- ggt ccg ggc cac ggt ggt cta cga gcc tca gcc agg tcc gac t- 3'  SEQ ID. 4
3'- agt cgg tcc agg ctg-P- 5'                                             SEQ ID. 5
```

The DNA fragments are then separated from unincorporated linker using the Qiagen PCR Purification kit and resuspended in 30 µl of Elution buffer (10 mM Tris.HCl pH8). The adapted DNA fragments are then digested at 37° C. for 16 h in a 200 µl volume reaction buffer (1× Buffer 4 [New England Biolabs] supplemented with 50 µM S-adenosylmethionine) containing 20 Units of MmeI restriction enzyme (New England Biolabs). Following digestion the fragments are precipitated and separated on a 12% non-denaturing acrylamide gel and the bands analysed. The free adaptor is evident as are a slower migrating species of adapter plus the 19/16 nt overhang generated by the asymmetric digestion of the genomic fragment by the type IIS restriction enzyme MmeI. This band is excised from the gel and the fragments recovered using standard techniques. The 19 nt on the upper strand is the portion of genetic material incorporated into the n[snare] plasmids as candidates for decoy sequences. As these fragments are biotinylated they are captured onto a paramagnetic matrix coated with streptavidin, such as M-280 beads from Dynal. The DNA on these beads is denatured in 0.5 M NaOH followed by heating to 80° C. and the resultant single stranded DNA washed in 1×Buffer 4 (New England Biolabs). 100 pmol of a Bbv complementary oligonucleotide (containing the Nt.BbvCI site which is underlined) of the following sequence:

```
                                           SEQ. ID. 6
5'- gga cct ggc tga ggc tcg tag acc acc gtg gcc cgg acc -3'
``` is annealed to the captured single stranded DNA in order to make a restriction site for Nt.BbvCI. Before digestion the beads are washed thoroughly to remove any oligonucleotides that fail to ligate. The mixture is now supplemented with 25 Units of the enzyme and the reaction incubated for 4 h at 37° C., after which the mixture is heated to 60° C. for 15 min to denature the nicked DNA. The 'snare' portion is released from the beads whilst the remainder is retained (FIG. 4). Following capture of the beads onto a magnetic stand, the DNA from the supernatant is recovered and used to create n[snare] plasmids using similar methods, as previously described.

2. Use of a Library of n[Snare] Plasmids to Upregulate Production of the Antibiotic Cinnamycin in its Natural Host The n[snare] library created from the cinnamycin biosynthetic cluster was introduced into the producer strain *S. cinnamoneus* by conjugation and plated onto R2YE agar (Kieser et al. (2000) Practical *Streptomyces* Genetics. John Innes Foundation) and allowed to grow for 3 days. Parallel control experiments were performed where *S. cinnamoneus* was untreated or conjugated with a donor strain containing an empty vector (containing none of the direct repeats). These controls allowed an estimate of the average size and distribution of 'halo' sizes so that measurement of halo sizes in the n[snare]-treated sample is used to determine the statistically significant over-producers. An example of an increase of halo size in a n[snare] exconjugant is shown in FIG. 5. When plated on solid R2YE medium *S. cinnamoneus* secretes an antibiotic, cinnamycin, into the agar that is capable of killing *Bacillus subtilis* cells when the producing colony is overlaid with a culture of that strain (left hand side). The diameter of this halo is used as a measure of the amount of cinnamycin produced. Production is increased by introduction of an n[snare] library containing fragments derived from the 17.083 kb cinnamycin biosynthetic cluster. Following introduction of members of the library by conjugation, clones are selected on the basis of increased production of cinnamycin (right).

Using this approach it was possible to identify n[snare] plasmids capable of upregulating antibiotic production, and, by extension, to find the key cis-regulatory sequences within the cinnamycin biosynthetic cluster controlling production. In one application, such sequences in n[snare] plasmids, or incorporated into TFDs, could be used to manipulate production of antibiotics, and other industrially valuable biologics. Using this approach, we have been able to enhance the level of production of previously identified actinomycete-derived compounds (FIG. 5). This is often a major stumbling block in the commercial development of a natural product, and this technology is suitable to exploit the full commercial potential of actinomycetes by activating or greatly enhancing the expression of so-called "cryptic" secondary metabolic gene clusters (Zazopoulos (2003) *Nat. Biotech.* 21: 187-190), or increase yields in general for industrial biotechnology. This platform technology is thus anticipated to benefit both human and animal healthcare, and it exemplifies the collaborative exploitation of both genome sequencing and developments in genomics.

Example 3

A Method for Using n[Snare] Libraries to Identify Cis-Regulatory Elements and, Therefore, Decoys, for Modifying Phenotype Using Engineered Reporter Systems.

1. Identifying Regulators of Cinnamycin Production with n[Snare] Libraries and Cin7-Reporter Strains The cinnamycin biosynthetic cluster has been previously described (Widdick and Bibb (2003) *Proc. Natl. Acad. Sci. USA* 100: 4316-4321) and the role of some of the identified genes confirmed by bioinformatical and genetic analysis. The cin7 gene is known to be preceded by the promoter that controls transcription of the cinMXTH operon that encodes the short protein (cinA) that is converted enzymatically to give the cinnamycin antibiotic (Sean O'Rourke and Mervyn Bibb, unpublished data). We created a reporter system driven by the cin7 promoter and introduced this construct into a *Streptomyces lividans* strain carrying the entire cinnamycin biosynthetic pathway (strain 1326). In order to demonstrate the approach, the cinnamycin custom n[snare] library (described in Example 2) was introduced into the strain by conjugation and exconjugants screened for survival in normally lethal concentrations of kanamycin.

2. Procedure for Detecting Negative Regulation with n[Snare] Libraries and a Reporter Based System The promoter of the targeted gene (cin7) is positioned upstream of a gene conferring kanamycin resistance, neo, as shown in FIG. 7. In this figure the targeted promoter of the cin7 gene from the cinnamycin biosynthetic cluster of the producing strain of *S. cinnamoneus*, is used to drive expression of the neo gene encoding resistance to the antibiotic kanamycin. A cis-regulatory sequence within the cin7 promoter is shown as a bar "A", to which a transcriptional repressor is bound (oval "B"), rendering the downstream neo gene inactive and consequently the strain is kanamycin sensitive. Typically, this chimeric gene is introduced into the genome of the producer strain by use of integrative vectors. A custom n[snare] library, in this instance created from the fractionated DNA of the *S. cinnamoneus* genome reporter strain, is introduced and transformants/exconjugants screened for resistance to increasing concentrations of kanamycin. Those cells that are more resistant are carried forward for further analysis.

Hence when there is no or little transcription in the cinnamycin biosynthetic cluster in the heterologous production strain *S. lividans* 1326, the cin7 promoter is transcriptionally inert and the host cell susceptible to kanamycin selection, with cell death occurring in strains containing a plasmid with a promoterless neo gene encoding resistance to kanamycin at concentrations lower than 5 µg/ml (Labes et al. (1997) *Microbiology* 143: 1503-1512). The cin7-neo chimeric gene is carried on an integrative plasmid (based on the pSET152 backbone Kieser et al. (2000) Practical *Streptomyces* Genetics. John Innes Foundation) that also carries the aacC gene encoding resistance to the antibiotic apramycin. We introduced the cassette into *S. lividans* strain 1326 (containing the cinnamycin biosynthetic cluster) by methods well known in the art to create a new strain (MM14) with chimeric gene stably integrated into the genome. The cinnamycin-custom n[snare] library made as described in Example 2 was introduced into MM14 bp standard methods to generate a spore suspension of the library. A fixed number of spores were used to inoculate R3 liquid media (Shirahama et al. (1981) *Agric. Biol. Chem.* 45: 1271-1273) and growth in the presence of an increasing concentration of kanamycin was monitored. Cell viability at each concentration was determined by withdrawing aliquots of the same volume from the cultures and spreading these onto agar plates (DNA agar) to determine colony forming units/ml culture, and from this the percentage of viable cells. These data show that in this experiment viability at 650 µg/ml kanamycin was less than 0.01%, which is estimated as equating to 1200 colony forming units in a 50 ml culture. This was considered to be the optimal concentration of kanamycin as it greatly enriched for those with increased resistance to the antibiotic, resulting in a manageable number of cells. Viability at 150 µg/ml was 85%, establishing the baseline activity of the cin7-neo construct.

A library hyrbidisation step was carried out. In this example, in four independent replicates, the MM14 strain was conjugated with the cinnamycin custom library. The optimal concentration of kanamycin for each repeat was determined empirically. Finally 96 clones from each repeat that survived at the optimal concentration were cultured in R3 media and then split into two aliquots. From one, plasmids were extracted from the cells using standard procedures, taking care to prevent contamination either by RNA or genomic DNA. This plasmid DNA was then labeled by random priming PCR using a DIG-labeled dUTP molecule according to standard methods (Roche manual) to create a Probe sample. The second aliquot was diluted and spread onto DNA agar plates at a concentration where individual colonies could be clearly seen. The plates were incubated at 30° C. for a period of 16 h, after which the colonies still maintained a waxy consistency and had not yet hardened. 96 such colonies were scrapped with a toothpick, which was first used to make a streak on a second DNA plate (supplemented with 50 µg/ml apramycin) and then mixed in 25 µl dimethylsulfoxide (DMSO), heated to 95° C. for 10 min and then cooled to create a solution of total DNA derived from the clone. Both the streak and the solution of DNA were numbered so that if subsequently the DNA sample was found to contain a candidate n[snare] plasmid a viable exconjugant (MM14 strain plus n[snare] plasmid) could be easily recovered.

Figure 9:
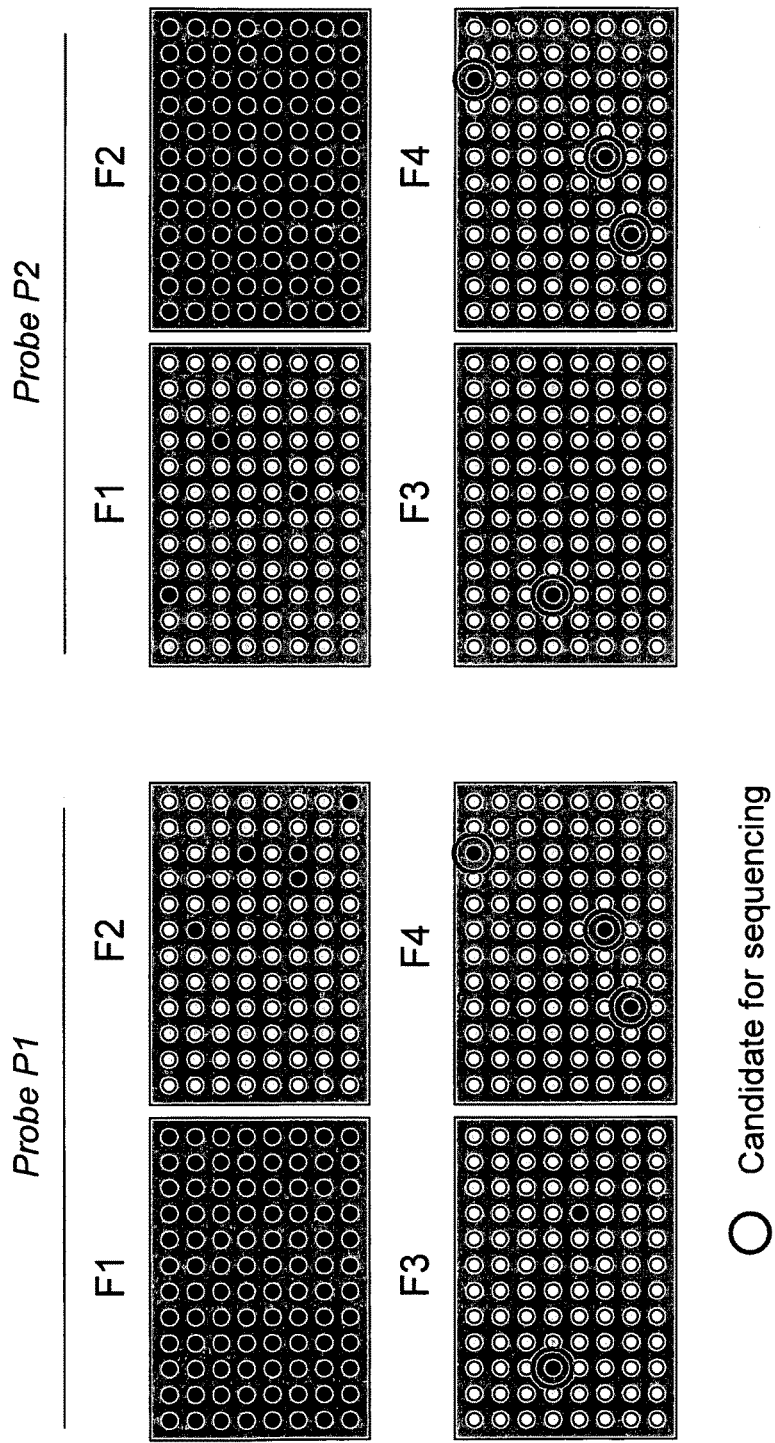
FIG. 9. Library hybridization to identify candidate clones. To distinguish 'background' members that form a considerable part of the 'total signal' from n[snare] plasmids genuinely able to interfere with transcription, a library hybridization strategy was developed using standard methods.

To identify n[snare] plasmids genuinely able to interfere with transcription (to distinguish 'background' members that form a considerable part of the total signal from n[snare] plasmids genuinely able to interfere with transcription), a library hybridization strategy was developed. In this example, using standard methods, DNA samples from 96 clones of each repeat were processed and hybridized to a nylon membrane each with an addressable position. The strategy pursued is shown in FIG. 9. For each repeat, four such filters (F1, F2, F3 and F4 derived respectively from each repeat) were made and then separately hybridized with different probes, so eventually all of the probe sets are hybridized to each of the filters. Hybridization of P1 and F1 detects a chromatogram where every sample is detected. Detection is not expected to be homogenous as n[snare] sequences that occur multiple times in the library are proportionally brighter. In this example, hybridizations of P1 and P2 with F3 and F4 detect samples common to all libraries. These samples would be considered strong candidates for continued scrutiny.

Figure 10:
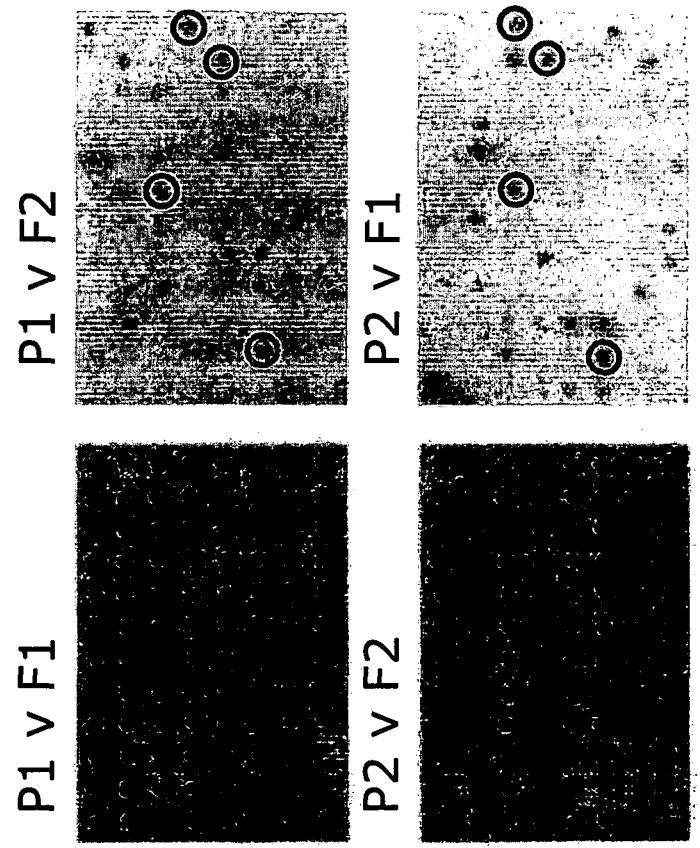
FIG. 10. Hybridization screens to detect candidates from independent repeats of the procedure to detect cis-regulators capable of regulating cinnamycin production using a generic reporter system and a custom n[snare] library. In this example two independent S. cinnamoneous libraries were tested with reporter strains and 96 of the most kanamycin resistant clones from each used to make a filter containing the n[snare] plasmids for each clone (F1 and F2), and two probe sets (P1 and P2). All of the clones identified by cross-hybridization (F1 versus P2 and F2 versus P1) were considered strong candidates, and priority was given to those common to both cross-hybridization experiments (circled in red).

Exemplary data of such a screen is shown in FIG. 10. In this example two independent repeats of the cinnamycin library were tested with reporter strains and 96 of the most kanamycin resistant clones from each used to make a filter containing the n[snare] plasmids in each replicate (F1 and F2), and two corresponding probe sets (P1 and P2). All of the clones identified by cross-hybridization (F1 versus P2 and F2 versus P1) were considered strong candidates, and priority was given to those common to both cross-hybridization experiments (circled in red). The sequence of three of the six clones studied identified a portion of the cin7 promoter and another two surrounding a potential cis-regulator from another gene within the cinnamycin cluster, cinR, which has been proposed to have a role in regulation of the cluster. The final sequence was not identified and was presumed to be derived from the *S. lividans* chromosome or be artefactual.

In some contexts the P1 with F1 hybridization, and other self hybridization experiments, may be capable of detecting false positive clones due to enrichment of, for example, repetitive sequences in eukaryotic libraries. These would generate far stronger signals due to their abundance in the library, i.e. greater than true positives that may be expected to occur more than once in the library but not as many times as repetitive DNA (types of which can account for 10% of the human genome by mass).

3. Adapting Reporters to Detect Positive Regulation

A simple adaptation is used to make the reporter system capable of detecting positive regulation, by creating a cassette consisting of a chimeric reporter gene incorporating the coding sequence for the glucose kinase gene (glkA) driven by the targeted promoter. This enzyme converts the metabolite 2-deoxyglucose (DOG) to the toxic, phosphorylated version of the compound. Hence by making a chimeric reporter gene consisting of the cin7 promoter linked to the glkA gene and stably integrating this into a *S. lividans* strain containing a glkA$^-$ deletion such a reporter system is provided (FIG. 8).

In the context of this experiment, the TK24 strain of *S. lividans* is used. This does not contain the cinnamycin biosynthetic cluster (as did the strain used in detecting negative cis-regulatory elements controlling production), and as such any activity of the cin7 promoter shall be due to positive regulators derived from the *S. lividans* genome. Hence, by searching for positive cis-regulatory sequences in this background it is expected to find up-regulators of heterologous expression from the chromosome of the *S. lividans* host. Titrating these positive regulators off the cin7 promoter and onto an n[snare] plasmid, prevents expression of glkA the cells grow in the presence of DOG. To date considerable work has been done, using conventional genetic screens, to detect such generic regulators of heterologous production, which may be caused by overexpression of certain components of the transcriptional machinery, such as sigma factors and components of the translational machinery. In addition a class of transcription factors known as SARPs (Butler et al. (2003) *Appl. Microbiol. Biotechnol.* 61: 512-516) have been identified and the cis-regulatory elements to which these bind are potential targets for this screen. The screen is conducted in the same way as described previously with similar advantages; compatibility with high-throughput processing, standardized methods and easily scoreable phenotypes.

Example 4

A Method for Using n[Snare] Libraries to Identify Cis-Regulatory Elements and, Therefore, Decoys for Modifying Phenotype in Undefined Genetic Systems 1. Creation of Genomic n[Snare] Libraries Purified *E. coli* K12 strain genomic DNA was sonicated to give an average size of 500 bp. The fragments were then treated as described in Example 2: adapted with a biotinylated linker containing convenient restriction sites, digested to produce adaptors plus a 19/17 nucleotide overhang, captured on a streptavidin matrix, before restriction and denaturation to release a single stranded DNA fragment containing a portion of the adaptor plus the 19 nucleotide overhang. These types of molecules are then used to create libraries of n[snare] plasmids using techniques as described in Example 2.

Figure 11:
FIG. 11. Restriction digest analysis of the Escherichia coli K12 genomic n[snare] library confirms it has the expected sequence properties. This mixture of plasmids was digested with EcoRI to regenerate the fragments used to create the n[snare] libraries, and these were subjected to MmeI digestion to confirm the molecular biology of construction had worked: as expected the inserts were of large size and these collapsed to a 30 bp monomer on digestion to completion with MmeI.

One version of the *E. coli* K12 genomic n[snare] library (hereafter referred to as 'K12 library') was estimated to have 1,560,000 members, which, considering the size of both the genome and the fragments used to construct the n[snare] library, corresponds to up to 99.8% coverage of the entire genome using standard analysis. Hence if there is no sequence bias in the creation of the libraries, then three independent versions of the K12 library should allow complete coverage of the genome. In order to assess whether there was any bias in the library, plasmids were isolated from an aliquot of said grown-in-liquid culture. This mixture of plasmids was digested with EcoRI to regenerate the fragments used to create the n[snare] libraries, and these were subjected to MmeI digestion to confirm the molecular biology of construction had worked: as expected the inserts were of large size and theses collapsed to a 30 bp monomer on digestion to completion with MmeI (FIG. 11), while partial digestion gave rise to intermediate products with sizes which were multimers of the 30 bp repeat. Sequencing of the collection of plasmids clearly confirmed the sequence of the 'spacer' element derived from the adaptor and that spacing was well preserved over at least ten copies. As expected the 'snare' portion of the plasmid collection was essentially random sequence with little nucleotide bias at any of the 19 positions.

2. Creation of Universal n[Snare] Libraries

Oligonucleotides were synthesized with the following sequence:

SEQ. ID. 7
5'-Phosphate- aat acg act cac tat agg gnn nnn nnn <u>ngc ggc cgc</u>- 3' where a restriction site for NotI is shown underlined, and a randomized nucleotide is represented by 'n'. In this example the number of randomized nucleotides is 9, but this number can be varied. The type of sequences encoded by the variable region can also be modified, for example by inclusion of constant regions in the sequence (i.e. a defined core sequence flanked by variable sequences), or by introducing nucleotide bias to the variable regions (i.e. by stipulating that 'n' should be a dGTP or dCTP 60% of the time to create randomized sequences with a higher GC-content). The protocol for creating n[snare] plasmids with this oligonucleotide containing randomized sequence, and hence, a universal n[snare] library is the same as that given in Example 2. We refer herein to these n[snare] libraries derived from randomized oligonucleotides as Universal libraries.

The titre of one version of the library was found to exceed 2 million. Using standard analysis, the confidence that a library of such titre would contain all possible combinations of 9 bp sequences would be $7.5 \times 10^5$. However, it is felt unlikely that such a library shall ever be truly universal as certain sequences will be depleted from the library for many reasons such as PCR-bias against GC-rich sequences or sequences with extensive secondary structure and those sequences in the collection that contain either/or MmeI or NotI sites. However it will be appreciated that what has been created has the potential to be a substantial and comprehensive collection of potential cis-regulatory sequences to use in the n[snare] library approach.

Figure 12:
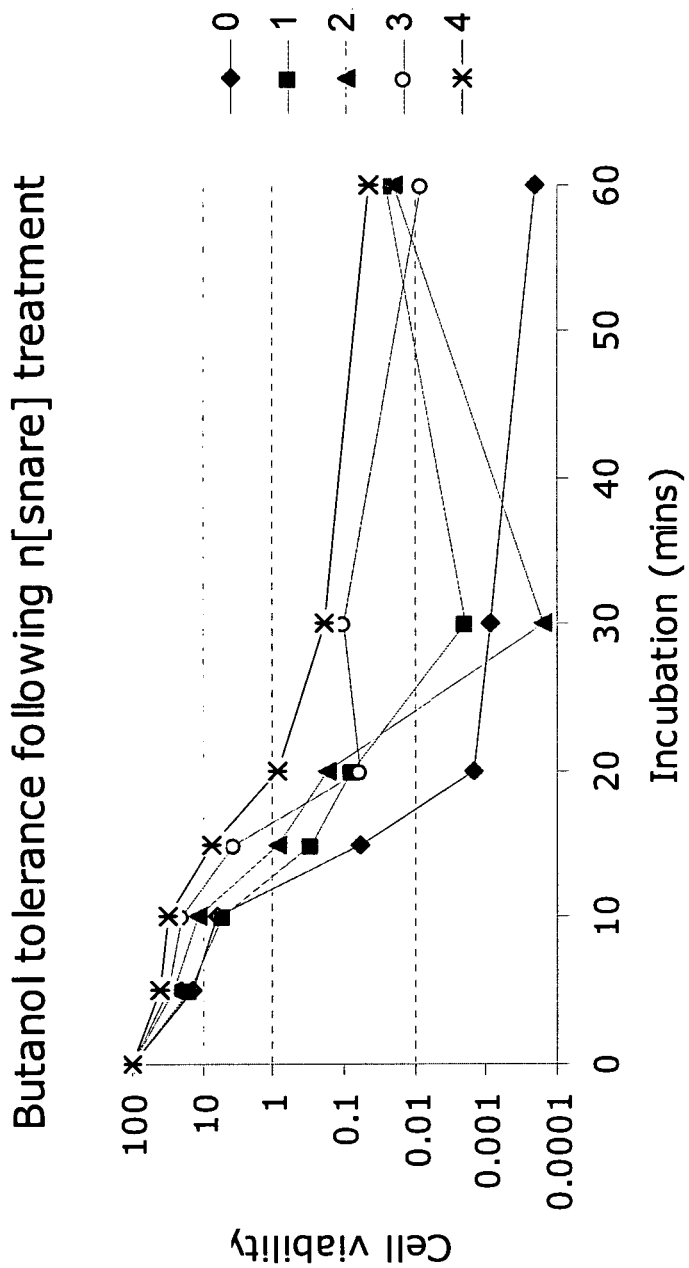
FIG. 12. n[snare] libraries are used to engineer phenotypes without prior knowledge of the genetic network. This process was repeated four times and the cell viability measured each time.

3. Procedure for Using n[Snare] Libraries to Detect Cis-Regulators of Phenotypes with Undefined Genetic Network The *E. coli* strain K12 was transformed with either the genomic n[snare] library or a version of the universal library and grown in liquid culture. When growth had reached mid log-phase as estimated by reading the absorbance of the culture (an $A_{600}$ reading of 0.4) and aliquots used to seed media supplemented with either no solvent or concentrations of butanol varying from 0.5% to 5%. The cultures were incubated for a further 1 h and then colony-forming units were measured in order to calculate cell viability. Cells were isolated from cultures in which viability had decreased 10,000 fold (to 0.01% or less) and washed in media free from solvent and used to reinoculate fresh medium without solvent. The experimental cycle was repeated; this culture grown to a density of 0.4 and used to inoculate media supplemented with increasing concentrations of butanol. This process was repeated four times and the cell viability measured each time (FIG. 12). Iteration of the selection process (meaning the library from existing members following one passage through butanol, were extracted and used to transform *E. coli* K12) increased the viability count as a function of the number of repeats of the selection procedure. *E. coli* that were not treated with the K12 n[snare] library were designated '0' (represented by the filled diamonds), those with 1 treatment were represented by filled squares, those with 2 by filled triangles, those with 3 by hollow circles and those with 4 by asterisks. What became evident was that bacteria transformed with either n[snare] library compared to control transformations, consisting of plasmid backbone with no n[snare] insert or untransformed, gave substantially higher cell viability accounts when cultured in the presence of high concentrations of butanol. In addition, it became evident that iteration of the selection process increased the viability count as a function of the number of repeats of the selection procedure.

The *E. coli* K12 custom library performed better than the universal n[snare] library, consistent with this library being more representative of the genome of the strain.

Example 5

Manipulating and Understanding Antibiotic Production in *Streptomyces coelicolor* A3(2) with Decoy Oligonucleotides What has been described to this point is a suite of innovative approaches to identify key cis-regulatory sequences implicated in the control of phenotypes. The technologies are universally applicable to all organisms. It was next demonstrated that knowledge of these sequences could be used to create tools capable of modifying gene expression in vivo. These tools are again functional in all organisms, but the focus of the following examples is use in prokaryotes. The transcription factor decoy approach is adapted for use in prokaryotes and shown to be a powerful way to mobilize the information generated by the n[snare] protocols to develop a system capable of modifying gene expression. The combination of the two approaches is referred to herein as "regulatory engineering".

In the example below the cis-regulatory sequences influencing antibiotic production in *Streptomyces coelicolor* are determined by a novel mapping procedure and these sequences used to design decoy oligonucleotides. The decoys are tested by introduction into *S. coelicolor* and their uptake, stability and effect of antibiotic production monitored. A complete description of the methods used is given in section 7 of this example.

1. Mapping Regulatory Elements within the actII-Orf4 Promoter

The DNA-protein interactions controlling expression of actII-orf4 were studied by in vivo DNaseI/T7 exonuclease mapping. This method was developed to identify the boundaries of cis-acting regulatory elements so that the deduced sequences could be used to design decoy oligonucleotides for functional studies. A schematic summary of the approach is given in FIG. 13. To map the in vivo boundaries of DNA-protein complexes at specific locations within the *S. coelicolor* genome, high concentrations of DNaseI and T7 exonuclease were added to freshly harvested cells. The DNaseI introduced 'nicks' into the DNA surrounding the complexes which then served as substrates for the 5' to 3' exonuclease activity of T7 exonuclease. Hence, the joint actions of the enzymes demarcate the 5' boundaries of the complexes. DNA is recovered from the treated cells and the fragments from the targeted promoter (actII-orf4) captured by hybridization to an immobilized strand of a PCR fragment of the promoter, which incorporates a biotinylated linker. The positions of boundaries within the population of captured fragments are mapped by performing a PCR reaction using a second DIG-non-radioactively labeled primer (incorporating digoxygenin, DIG [Roche]) that hybridizes to the biotinylated linker. The sizes of the labeled products are determined by PAGE and chemo-luminescent detection. Boundaries on the opposite strand are mapped in a similar manner, using a PCR product with the biotinylated linker at the opposite end. The labeled PCR fragments were size fractionated following 12% polyacrylamide gel electrophoresis and the presence of the fragments and their size determined following chemo-luminescent detection. The novel combination of T7 exonuclease and DNaseI in a footprinting protocol allows detection of all the boundaries of DNA-protein complexes within a promoter region, and not just those closest to a chosen restriction site.

Figure 14:
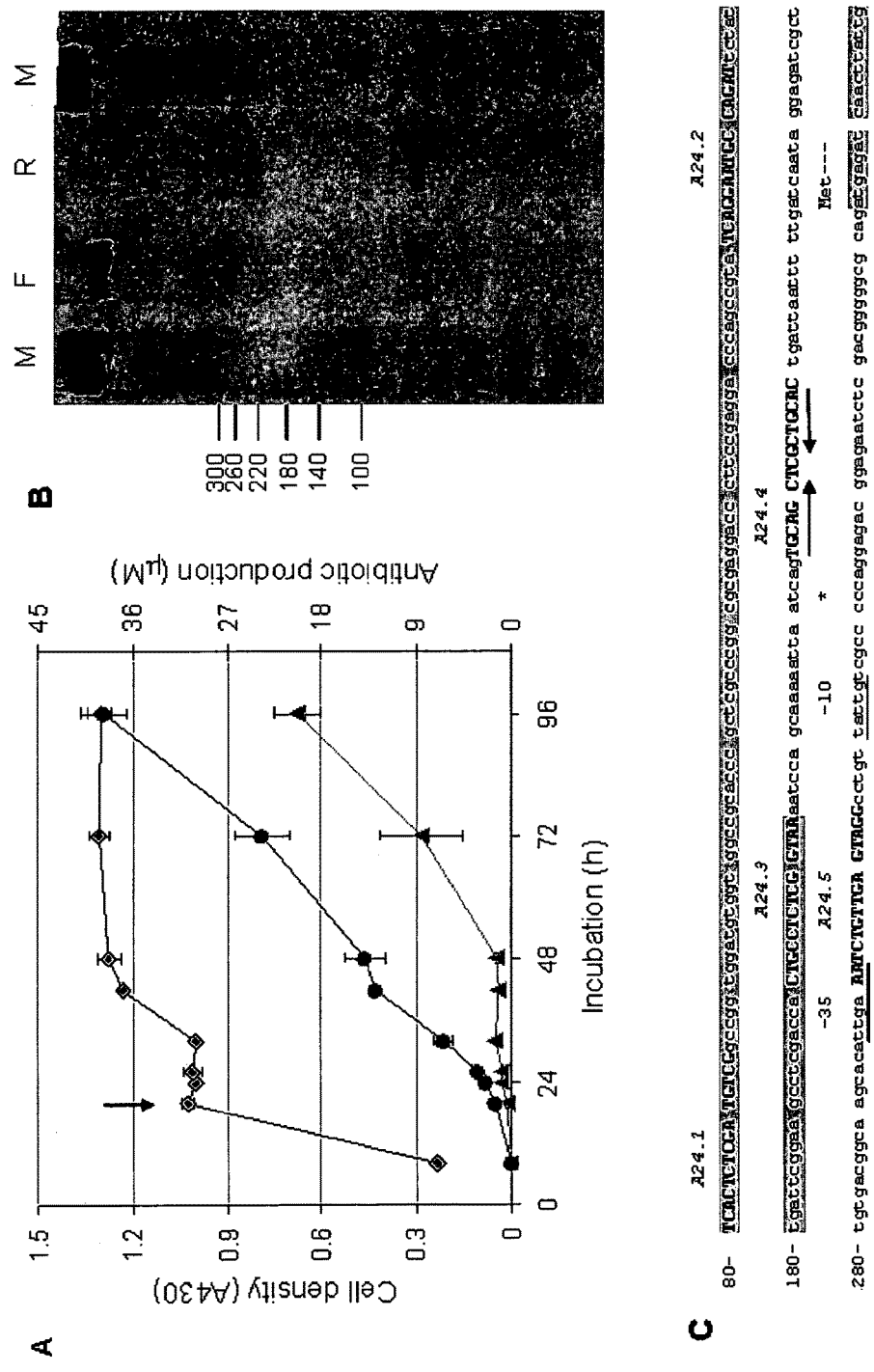
FIG. 14. T7 exonuclease/DNaseI mapping of candidate regulatory motifs within the promoter of actII-orf4. (A) Cells of S. coelicolor M145 were harvested from a culture grown in rich (R5) media at a time point (indicated by arrow) preceding visible actinorhodin production. (B) Boundaries were mapped on both strands, as described in FIG. 13, and their positions determined following size analysis by 12% non-denaturing PAGE, followed by chemoluminescent detection of DIG-labeled products. (C) The sequence of the actII-orf4 promoter (SEQ ID NO:27) showing the positions of the putative cis-regulatory elements (relative to the primers used in the mapping protocol).

Since our aim was to discover regulatory elements involved in the repression of actII-orf4 expression, we mapped the transcriptionally down-regulated promoter in a rich liquid medium (R5). Under these conditions repressors may occupy the promoter and prevent expression. Growth curves were derived by measuring cell density ($A_{430}$ of the culture), and production of the two pigmented antibiotics (the blue actinorhodin, and the red undecylprodigiosin [Kieser et al. (2000) Practical *Streptomyces* Genetics. John Innes Foundation), and the transcriptional activity of actII-orf4 determined. The latter is known to be induced during later stages of growth and thus samples for mapping were harvested prior to the visually detectable onset of actinorhodin production (indicated by the arrow in FIG. 14A). Cells of *S. coelicolor* M145 were harvested from a culture grown in rich (R5) media at a time point (indicated by arrow) preceding visible actinorhodin production. Cell growth (diamond) and production of actinorhodin (triangle) and undecylprodigiosin (circle) were monitored throughout. The amounts of the enzymes required for digestion were determined empirically, with the concentration of DNaseI needing careful optimization. For example, an excess of DNaseI resulted in loss of signal clarity due to cutting within the DNA-protein complexes, whereas too little enzyme was ineffectual for mapping. 250 U of T7 exonuclease per reaction worked well in most cases; it was necessary to add an excess of the enzyme as it is not highly processive, nor was the digestion performed in an optimal buffer. Boundaries were mapped on both strands, as described in FIG. 13, and their positions determined following size analysis by 12% non-denaturing PAGE, followed by chemo-luminescent detection of DIG-labeled products. (FIG. 14B), and by comparison with a standard size ladder it was possible to define the boundaries of the DNA-protein complexes in the transcriptionally silent actII-orf4 promoter region (FIG. 14C). The sequence of the actII-orf4 promoter showing the positions of the putative cis-regulatory elements (relative to the primers used in the mapping protocol). Boxed areas indicate the coding sequences of the upstream gene (actII-orf3) and actII-orf4 itself. Capitalized sequence marks the candidate regulatory elements with their names shown above. The underlined sequences indicate the −35 and −10 boxes for the actII-orf4 promoter, the asterisk shows the position of the transcriptional start site, and the convergent arrows indicate the inverted repeat present in A24.4.

We referred to the sequences defined by these regions as regulatory elements, and in total five were seen. The regulatory elements were labeled A24.1 to A24.5 (going towards the transcriptional start site) and these sequences were used to design the decoy oligonucleotides used in the subsequent functional studies.

2. Rapid Screening for Decoy Function on Agar Plates

Figure 15:
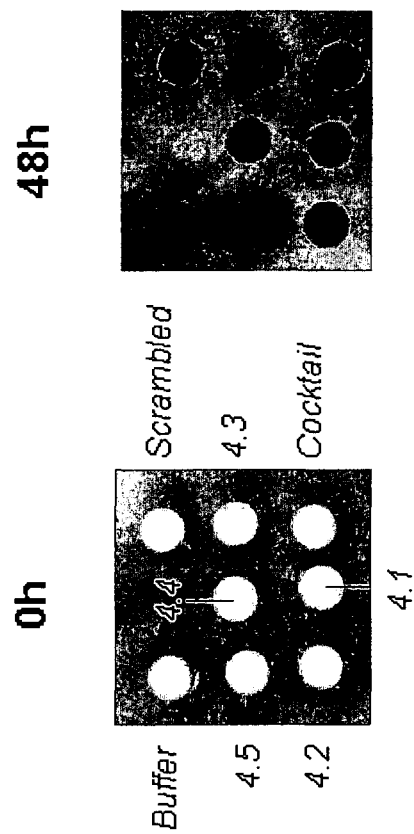
FIG. 15. Plate assays demonstrating that decoy oligonucleotides can influence antibiotic production in S. coelicolor. Filter discs were saturated with solutions of decoys or, as control, buffer (as shown) and applied to a lawn of S. coelicolor M145 overlaid with SNA medium.

We developed a rapid agar plate-based assay to test whether the decoys had any effect on antibiotic production. R2YE agar was used since it promotes the production of both of the pigmented antibiotics at levels that are readily detectable by eye. Plates were inoculated with a dilute spore suspension and incubated for 24 h at 30° C. so that confluent lawns of S. coelicolor formed. At this stage undecylprodigiosin (which is red) production had begun but not actinorhodin (which is blue). The plates were covered with a thin layer of SNA in 0.5% agarose and before this set, small disks of Whatman paper (Antibiotic Assay disks) were laid onto the medium and saturated with 15 µl of a 10 pmol/µl solution of decoy oligonucleotide, or control solution, as indicated in FIG. 15 Filter discs were saturated with solutions of decoys or, as control, buffer (as shown) and applied to a lawn of S. coelicolor M145 overlaid with SNA medium (Soft Nutrient Agar: 0.5% Difco Agar w/v). As the bacteria continued to grow, incidences of enhanced antibiotic production could be recognized by early accumulation of the pigmented antibiotics within and around the disks (evident 48 hours after addition of the decoys). Negative controls (buffer alone or a 'scrambled' version of decoy A24.5) did not show precocious production. All samples were prepared in a buffer containing 0.5% (v/v) of the two non-ionic detergents NP-40 and Triton X-100, which were found to improve the efficiency of transfection. The controls consisted of the buffer alone or a scrambled decoy oligonucleotide, where the sequence of the A24.5 decoy was randomized. The plate was incubated further at 30° C. and inspected regularly to determine whether there were any effects on the amount or the timing of antibiotic production. A purple/red halo was seen around the disk soaked with A24.5, and to a lesser extent A24.3 and the cocktail of decoys A24.1 to A24.4 (FIG. 15, 48 h; at earlier time points actinorhodin appears red as the molecule acts as a pH indicator, though the halos were clearly visible above the background of secreted undecylprodigiosin). To confirm that actinorhodin synthesis had begun, the disks at 48 hours were recovered, pigments extracted and quantified spectrophotometrically; decoy A24.5 strongly activated early actinorhodin production, while A24.3 and the cocktail of decoys did so to a lesser extent (data not shown). No early actinorhodin production was seen surrounding the control disks. By 96 hours the entire lawn of S. coelicolor M145 had produced large amounts of both antibiotics (not shown), and no zones of growth inhibition were apparent around any of the disks. The ability of some of the decoys to enhance production of actinorhodin at early time points, potentially by interfering with the binding of repressors to their identified sites within the actII-orf4 promoter region, demonstrated the efficacy of the approach and stimulated us to perform more extensive functional studies by introducing the decoys into cells grown in liquid culture.

3. Uptake and Stability of Decoys in Liquid Cultures

Figure 16:
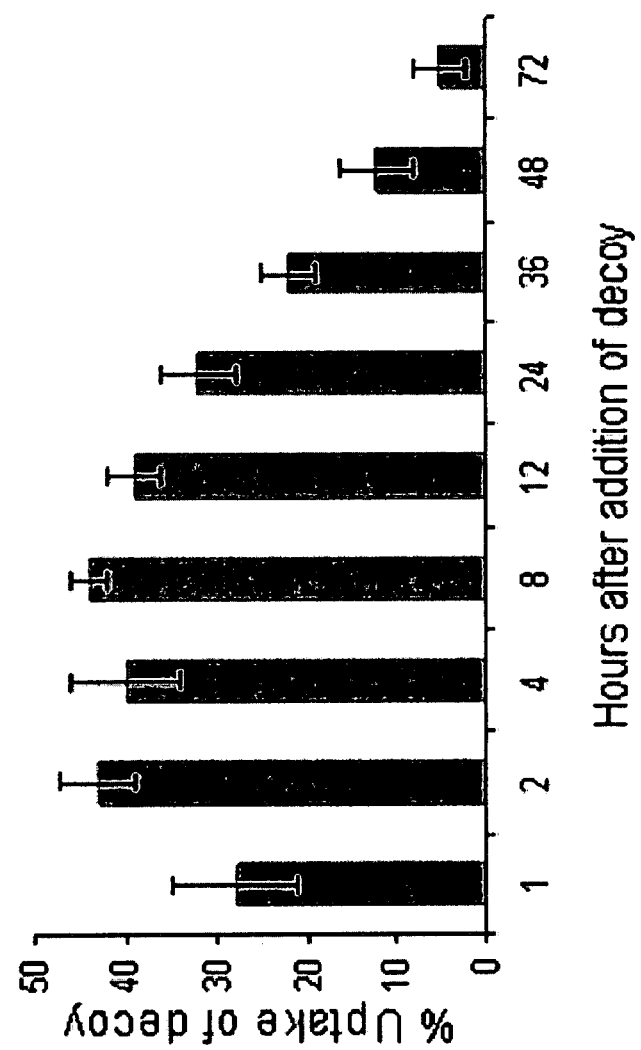
FIG. 16. Uptake and stability of decoy oligonucleotide. Actively growing cells were transfected with a solution containing decoy and the uptake of the oligonucleotide and its stability estimated by quantitative real-time PCR (qrt-PCR).

The next issues to address were whether or not a decoy could be efficiently introduced into mycelium in liquid culture, and if so, for how long would it persist? Six liquid cultures of S. coelicolor M145 were set up in SMM media (Kieser et al. (2000) Practical Streptomyces Genetics. John Innes Foundation) and grown to mid-exponential phase. Cells were collected by gentle centrifugation and resuspended in one tenth of the original volume of a permeabilizing buffer (containing the same concentrations of detergents as used in the plate assays) before transfection with varying amounts of decoy A24.1 (0 mM, 5 mM, 10 mM, 20 mM, 50 mM and 100 mM). Following brief incubation, the cells were resuspended in the retained media and incubation continued. Uptake of the decoy oligonucleotide was measured by qrt-PCR, using primers designed to amplify a small fragment (40 bp) spanning the join introduced in the formation of the dumbbell decoy. Reference to a standard curve was used to calculate the absolute number of copies of decoy present within the cells (following centrifugation and two wash steps), and this was corrected by reference to a genomic control. To assess stability, aliquots were withdrawn at various time points (0 to 72 hours). The rate of uptake saturated above concentrations of 20 mM. Optimal uptake was achieved with a 20 mM transfection, 2 hours following which 45% of the decoy had entered the cells (FIG. 16). Actively growing cells were transfected with a solution containing decoy and the uptake of the oligonucleotide and its stability estimated by quantitative real-time PCR (qrt-PCR). Following transfection with 20 mM A24.1, cells were harvested and washed before qrt-PCR was used to estimate copies of decoy remaining in the cell as a function of time. The data represents three independent determinations. The decoy could be detected intracellularly 72 hours after addition, with 22% (corresponding to half that had entered the cells) persisting after 36 hours. Since the cultures were transfected when nearing stationary phase, it was assumed that the decoys were being slowly degraded by endogenous nucleases as opposed to being lost due to dilution. Thus the decoy was able to enter the mycelium and persist for a prolonged period, suggesting that this approach could be used to alter gene expression in liquid cultures.

4. Use of Decoy Oligonucleotides to Control Antibiotic Production

Figure 17:
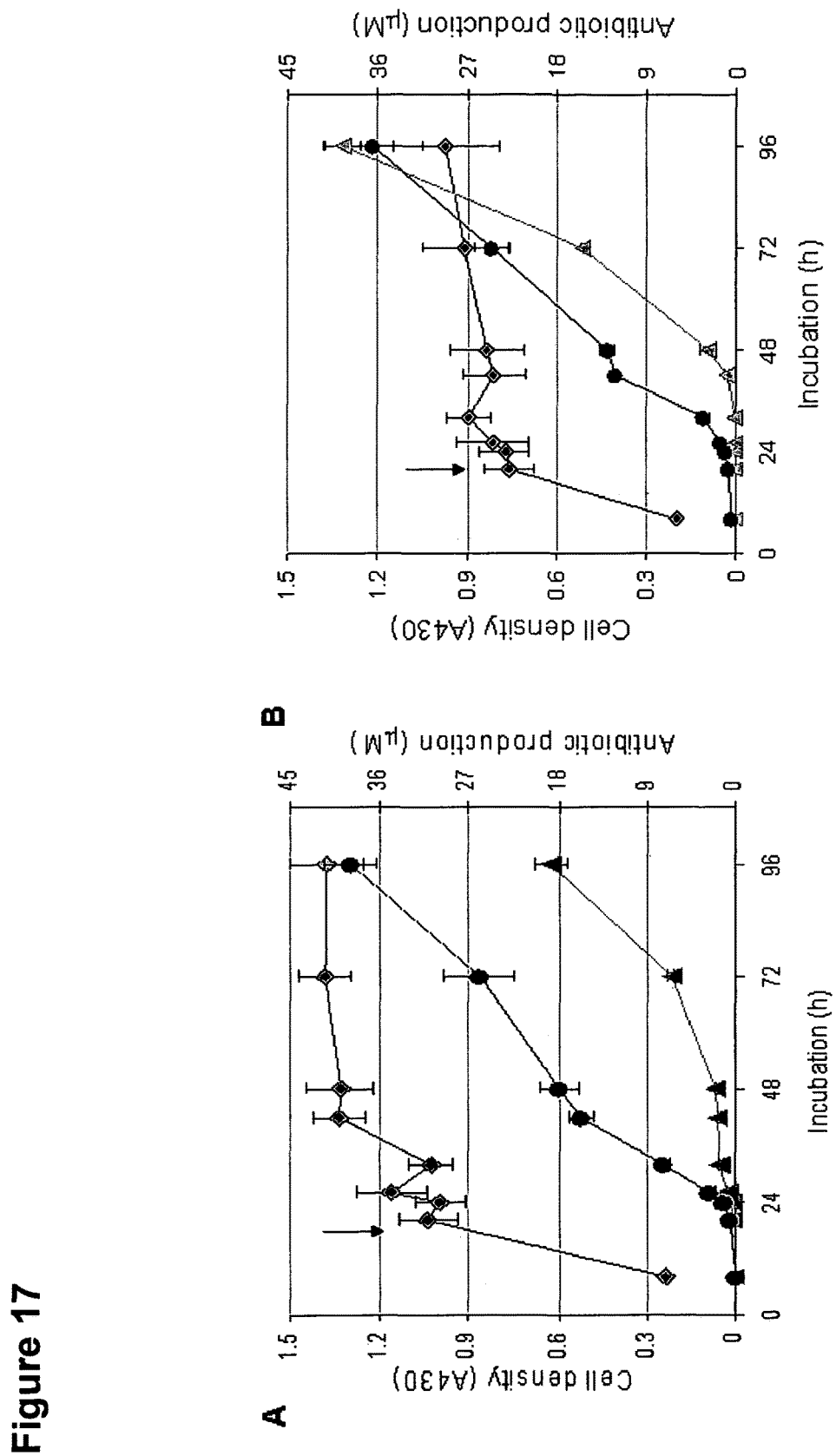
FIG. 17. Decoy-mediated increase in actinorhodin production in cultures grown in R5 liquid medium. S. coelicolor M145 was grown for 20 hours before transfection (indicated by arrows) with (A) a no-decoy control or with (B) the A24.5 decoy.
Figure 18:
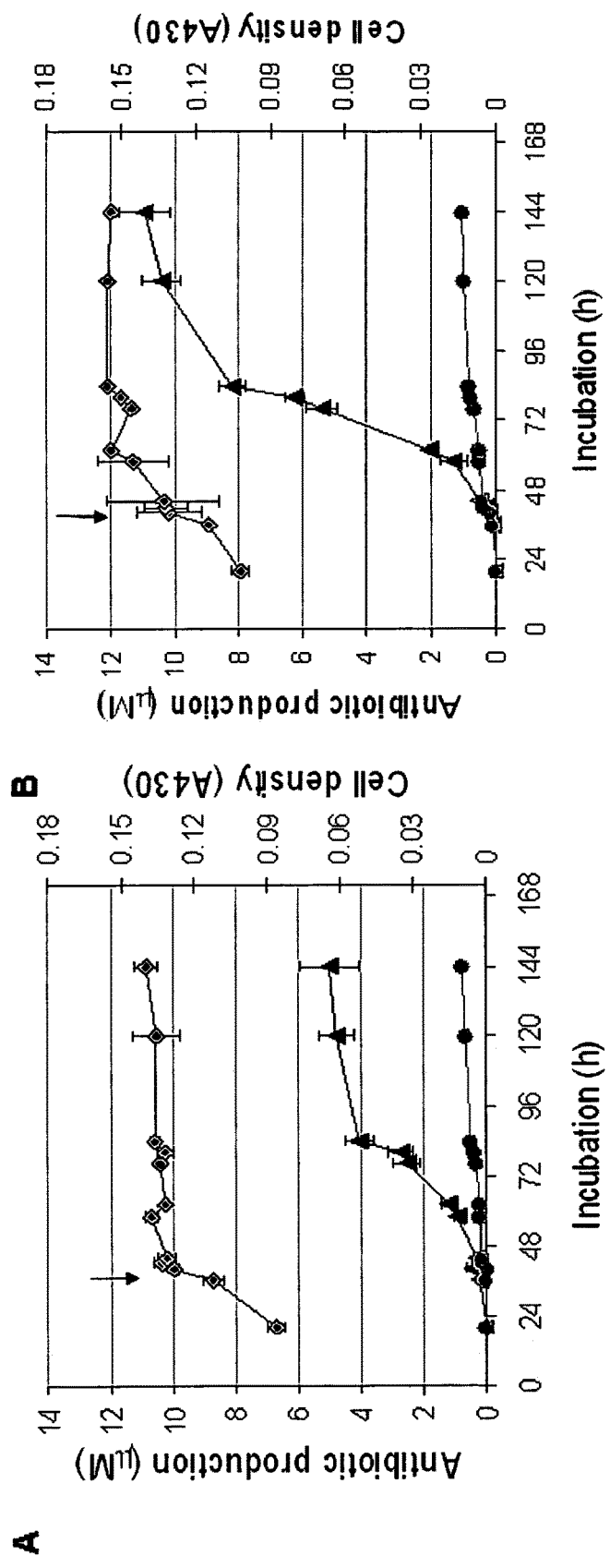
FIG. 18. Decoy-mediated increase in actinorhodin production in cultures grown in SMM liquid medium. Comparison of the data obtained with (A) a mock-transfected control and (B) a decoy A24.5-treated culture revealed that the decoy oligonucleotide caused a pronounced increase in actinorhodin production.

The five decoys, corresponding to the identified regulatory elements, were used to transfect liquid cultures of S. coelicolor M145 grown in R5 or SMM liquid media. Transfection was timed to precede the expression of actII-orf4, providing the decoys with the opportunity to interact with their cognate transcription factors and potentially influence actinorhodin production. Control experiments were similar to those used in the plate assays and consisted of either a mock transfection procedure or the introduction of three scrambled decoys (based on the sequences of decoys A24.1, A24.3 and A24.5). In each experiment, the growth of the culture was measured, as well as the production of the pigmented antibiotics and the expression of actII-orf4, at fixed intervals following transfection. None of the decoys altered the growth of the cells, but several did have an effect on the production of actinorhodin, and in some instances undecylprodigiosin. In R5 medium, where antibiotic production is relatively high, decoy A24.5 up-regulated actinorhodin production, increasing yield by 95% at the 96 hour time point (FIGS. 17A and B). S. coelicolor M145 was grown for 20 hours before transfection (indicated by arrows) with (A) a no-decoy control or with (B) the A24.5 decoy. Cell growth (diamonds) and the amount of undecylprodigiosin produced (circles) was similar in the two cultures, and the only variation seen was in the accumulation of actinorhodin (triangles), which was stimulated following treatment with decoy A24.5. The data represent the average of three independent determinations and the bars show the standard error. Decoys A24.1 and A24.3 had milder effects, causing up-regulation of both pigmented antibiotics. In all of the treatments where an increase in actinorhodin production occurred, there was a corresponding increase in the absolute level of actII-orf4 expression (determined by qrt-PCR; data not shown). Hence the results were largely consistent with those seen on the plates, suggesting that the effect of the decoys is specific and predictable. The decoys were also tested in SMM medium, a minimal medium that supports less antibiotic production than R5. Transfection with decoy A24.5 led to a doubling in actinorhodin production (FIGS. 18 A and B). Comparison of the data obtained with (A) a mock-transfected control and (B) a decoy A24.5-treated culture revealed that the decoy oligonucleotide caused a pronounced increase in actinorhodin production. The data are presented as in FIG. 17 and are is the average of three independent determinations; bars show the standard error. In this medium, increases in actinorhodin production were also seen for decoys A24.1 and A24.3 (data not shown). Hence, the decoys acted as convenient tools to validate the identification of cis-acting regulatory elements within the actII-orf4 promoter, allowing us to influence the onset of antibiotic production. As indicated above, several of the decoys also upregulated undecylprodigiosin production and possible reasons for this co-regulation are addressed below.

5. Discovery of a New Modifier of Actinorhodin Production

Figure 19:
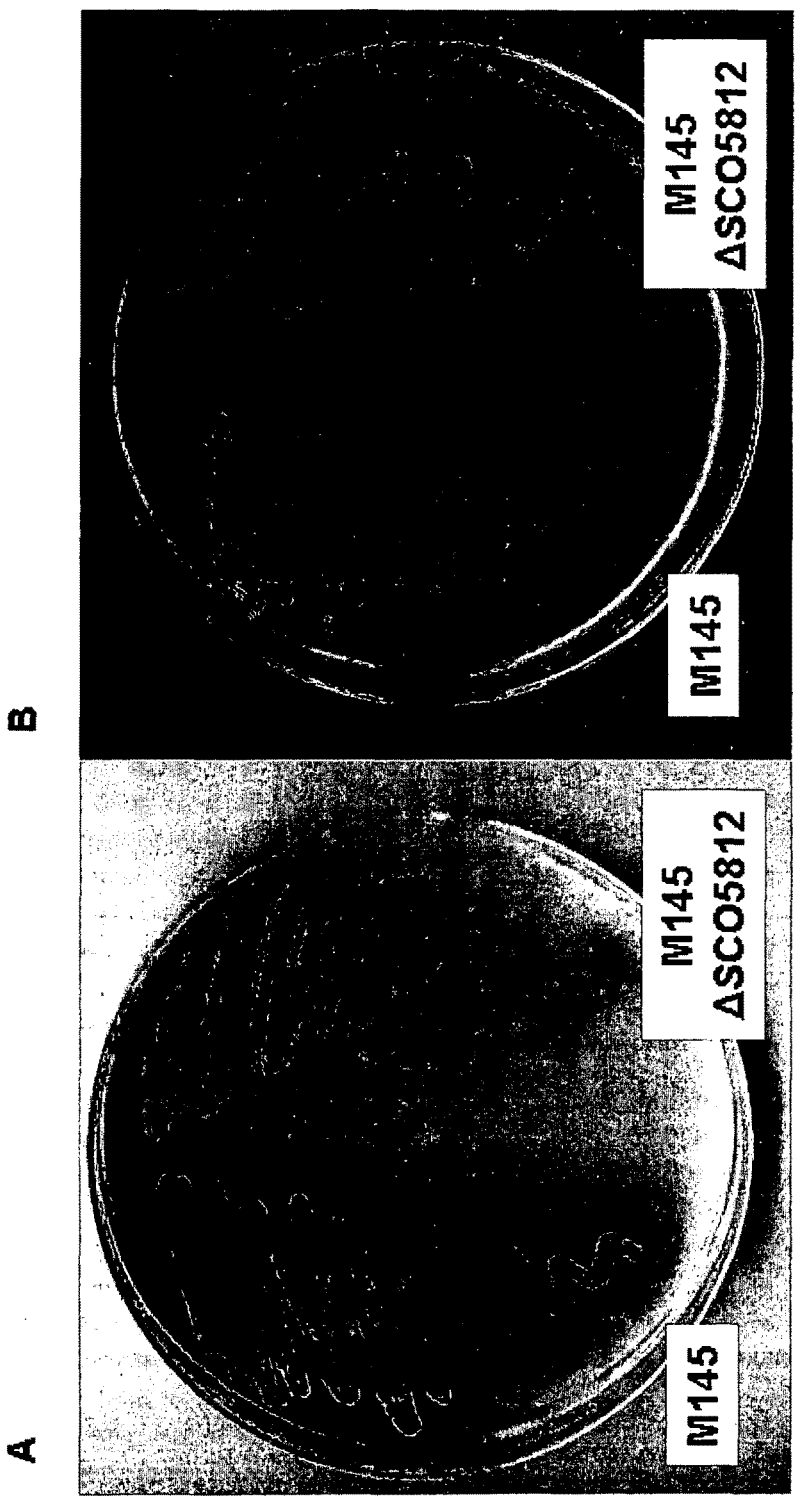
FIG. 19. Deletion of SCO5812 leads to underproduction of actinorhodin on R5 agar and overproduction of undecylprodigiosin on SMMS agar. M145 (left side of plates) and M145 ΔSCO5812 (right side of plates) were streaked on (A) R5 agar medium or (B) SMMS agar medium and incubated for 72 hr and 96 hr, respectively.

The combination of a novel mapping technique and decoy oligonucleotides has been used to validate three regulatory elements controlling expression of the actinorhodin regulatory gene actII-orf4. We next asked whether these regulatory motifs occurred in the promoter regions of any other genes; such genes might also be involved in the regulation of antibiotic production. Performing a BLAST search with all five decoy sequences identified one such gene. SCO5812 contained strong matches to A24.1 (a run of 10 out of 14) and A24.3 (a run of 11 out of 18). The gene itself is a potential homologue of ribonuclease HII, and as such may have a similar function to a previously identified pleiotropic mutant in antibiotic production, absB (SCO5572; Adamidis & Champness (1992) *J. Bacteria* 174:4622-4628), which is a homologue of RNaseIII and thought to be involved in transcript processing (Chang et al. (2005) *J. Biol. Chem.* 280:33213-33219). To establish the role, if any, of SCO5812 in antibiotic production, we deleted the gene from M145 and compared production with the parental strain on R5 and SMMS media (FIG. 19). In this figure M145 (left side of plates) and M145 ΔSCO5812 (right side of plates) were streaked on (A) R5 agar medium or (B) SMMS agar medium and incubated for 72 hr and 96 hr, respectively. While deletion of SCO5812 dramatically reduced actinorhodin production on R5 agar, it enhanced undecylprodigiosin production on SMMS. It is of interest to note that cells transfected with either A24.1 or A24.3 showed a slight up-regulation of undecylprodigiosin production, suggesting that the transcription factors that bind to these sites may influence the expression of both of the antibiotic biosynthetic gene clusters. Also one of the decoys tested, A24.4, which contains a 6 bp inverted repeat (FIG. 14), was found to have a match (8 out of 12) in the promoter region of redD, the pathway-specific activator gene of the undecylprodigiosin biosynthetic cluster (Takano et al. (1992) *Mol. Microbiol.* 6:2797-2804). This motif is a predicted binding site for the nucleoid protein IHF (on the basis of sequence homology to previously identified sites), raising the possibility that the site has an architectural role in the nucleoprotein complex instead of directly affecting transcription.

6. Concluding Remarks

We have used novel techniques to identify and validate a binding site for a repressor of antibiotic production in *S. coelicolor*. Validation was performed with decoy oligonucleotides: transfection of copies of these regulatory elements led to derepression of the targeted gene and increased production of actinorhodin. The intention of our work was to demonstrate that decoy oligonucleotides can be a valuable tool in prokaryotes to rapidly delineate genetic networks. Has it been successful? In two senses it has been. Three of the five decoys tested showed the expected activity. The decoy with the strongest effect, A24.5, has been shown recently to be bound by a TetR-like transcriptional regulator, AtrA, when the promoter is active (Uguru et al. (2005) *Mol. Microbiol.* 58:131-150). Our own work, using affinity purification to identify repressors of actII-orf4, has similarly identified TetR-like transcription factors bound to this site; it is our assumption that as decoy A24.5 is added prior to transcription of actII-orf4, it allows expression by diminishing the binding of these putative repressors.

7. Materials and Methods 7.1 Strains and Growth Conditions

A standard reference for general techniques concerning the handling of streptomycetes is Kieser et al. (2000) Practical *Streptomyces* Genetics. John Innes Foundation. Spores of *S. coelicolor* A3(2) strain M145 were germinated synchronously by heat treatment and grown in SMM or R5 medium at 30° C. with continual shaking. Growth of the culture and actinorhodin production were measured as described previously. R2YE and SNA were used for agar plate assays of decoy-induced antibiotic production. Deletion of SCO5812 was accomplished by PCR-targeting (Gust et al. (2003) *Proc. Natl. Acad. Sci. USA* 100: 1541-1546).

7.2 In Vivo T7 Exonuclease-Mapping

Prior to treatment with the footprinting reagent, cultures of *S. coelicolor* mycelial fragments were supplemented with 0.5 mM $CaCl_2$ and 50 units DNaseI (to remove extracellular DNA) and incubated for a further 15 min at 30° C. The mycelium was harvested by low speed centrifugation and washed extensively in TES buffer (13) supplemented with 5 mM EDTA. For DNaseI footprinting, the cells were washed in TES supplemented with 0.5% (v/v) NP-40 and 0.5% (v/v) Triton X-100, and incubated at 30° C. for 15 min. The cells were then washed in DNaseI Digestion Buffer (DDB) preheated to 30° C. and digested with varying amounts of DNaseI for 5 minutes. Reactions were stopped by addition of an equal volume of STOP buffer (50 mM Tris.HCl, 5 mM EDTA, 0.2% (w/v) SDS, 10 mg/ml Proteinase K, pH8) and incubated overnight at 55° C. Nucleic acids were ethanol precipitated following two rounds of phenol-chloroform extraction. The samples were digested with RNaseA before reprecipitation and quantification.

7.3 Decoy Oligonucleotide Studies

The sequences of all oligonucleotides used are listed in Table 1. Decoy oligonucleotides were synthesized (Invitrogen) and ligated with CircLigase (Epicentre) to create dumbbells (Mann & Dzau (2000) *J. Clin. Investigation* 106: 1071-1075). 100 pmol of each decoy oligonucleotide were mixed in a 20 µl reaction volume of 1× CircLigase buffer supplemented with 50 µM ATP, 2.5 mM $MnCl_2$, 500 U CircLigase, and incubated for 1 hour at 60° C. The mixture was treated with an excess of exonuclease I to remove linear DNA, and the remaining covalent circles precipitated. Each preparation was analyzed by 12% non-denaturing gel electrophoresis to check that the majority of products were monovalent covalent circles. The sample was resuspended at 200 pmol/µl in TE (10 mM Tris-HCl, pH 8.0, 1 mM EDTA) buffer. 10 µl of each decoy were spotted onto 3 mm antibiotic assay disks which were then pressed gently into a thin layer of SNA agar that had been poured over a 24 hour old confluent lawn of *S. coelicolor* M145 grown on an R2YE agar plate. Induction of antibiotic production would result in a localized increase in pigmentation surrounding the disk. Alternatively the dumbbell decoy oligonucleotides were used to transfect mycelium from exponentially growing cultures of *S. coelicolor* M145. Transfection involved washing the cells in equal volumes of TES buffer supplemented with 0.5% (v/v) NP-40 and 0.5% (v/v) Triton X-100, then resuspending them into $\frac{1}{10}^{th}$ of their original volume in TES plus detergents and supplemented with decoy oligonucleotide. The cells were incubated at 30° C. for 15 min with gentle mixing, diluted in the retained culture medium and incubation continued. Growth rate slowed temporarily following this treatment but soon recovered. Samples were taken thereafter to assess the levels of production of the two pigmented antibiotics, actinorhodin and undecylprodigiosin (13). Samples were simultaneously withdrawn for RNA analysis.

7.4 Gene Expression and Decoy Copy Number Analysis

Expression analysis was performed by quantitative real-time PCR (qrt-PCR). Preparation of cDNA was performed as previously described (Ryding et al. (2002) *J. Bacteriol.* 184: 794-805.). Briefly, 1 µg of RNA was thermally denatured (incubated at 70° C. for 10 min and then placed on ice) and mixed with 0.5 U AVM Reverse Transcriptase (Amersham), 1 mM dNTPs, 25 pmol custom primer in 20 µl of the supplier's recommended buffer. The reaction was incubated at three successive temperatures, 45° C., 50° C. and 55° C., each for 30 min. 4 µl of this reaction was used as a template in a 20 nl qrt-PCR reaction prepared in Invitrogen's SYBR Greener reaction mix supplemented with 10% (v/v) DMSO and 25 pmol of the custom forward and reverse primers for the target gene (actII-orf4) and an internal reference (SCO4742, a conserved hypothetical protein that was found to show little variation in expression following microarray analysis (Table 1). Amplification and analysis were performed on a BioRad Chromo4 machine. Determination of the copy number of decoys was similarly performed using SYBR-green detection. Primers were designed (Table 1) to detect circularized decoy oligonucleotides and their copy number determined by sonication of mycelium and comparison to known amounts of exonuclease-treated decoy; these values were corrected for the number of genomes in the sample by reference to the number of copies of SCO4742 present.

TABLE 1

| Name No. | Sequence | SEQ. ID. |
|---|---|---|
| Decoy oligonucleotides | | |
| A24.1 | 5'- P-atatcactctcgatgtcggcgttttcgc cgacatcgagagtgatatagttttct- 3' | 8 |
| A24.2 | 5'- P-atatcaggaatgccagatgcgttttcgc atctggcattcctgatatagttttct- 3' | 9 |
| A24.3 | 5'- P-atactgcctctcggtaagcgttttcgcttaccgagaggcagtatagttttct- 3' | 10 |
| A24.4 | 5'- P-atatgcagctcgctgcacgcgttttcgc gtgcagcgagctgcatatagttttct- 3' | 11 |
| A24.5 | 5'- P-ataaatctgttgagtagggcgttttcgc cctactcaacagatttatagttttct- 3' | 12 |
| A24.5 scrambled | 5'- P-atagcaattttagatggtggcgttttcgc caccatctaaattgctatagttttct- 3' | 13 |
| Quantitative PCR for decoy copy number | | |
| A24.1 copy f | 5'- cgacatcgagagtgatatagtttt- 3' | 14 |
| A24.1 copy r | 5'- gccgacatcgagagtgatat- 3' | 15 |
| Quantitative PCR for expression data | | |
| A24 custom | 5'- tgtcgccccaggagacggag- 3' | 16 |
| qA24f | 5'- cttaaatcctcgaaggcgacccag -3' | 17 |
| qA24r | 5'- tcctcgagccggttctcctcg- 3' | 18 |
| q4742f | 5'- gctggtggacatcggtct- 3' | 19 |
| q4742r | 5'- gccggtacttgtcgctctc- 3' | 20 |

The cis-regulatory sequences in each of the decoy oligonucleotides are underlined.

Example 6

Demonstration that Decoy Oligodeoxynucleotides May be Used in the Therapeutic Context to Overcome Antibiotic Resistance in Pathogens

Figure 20:
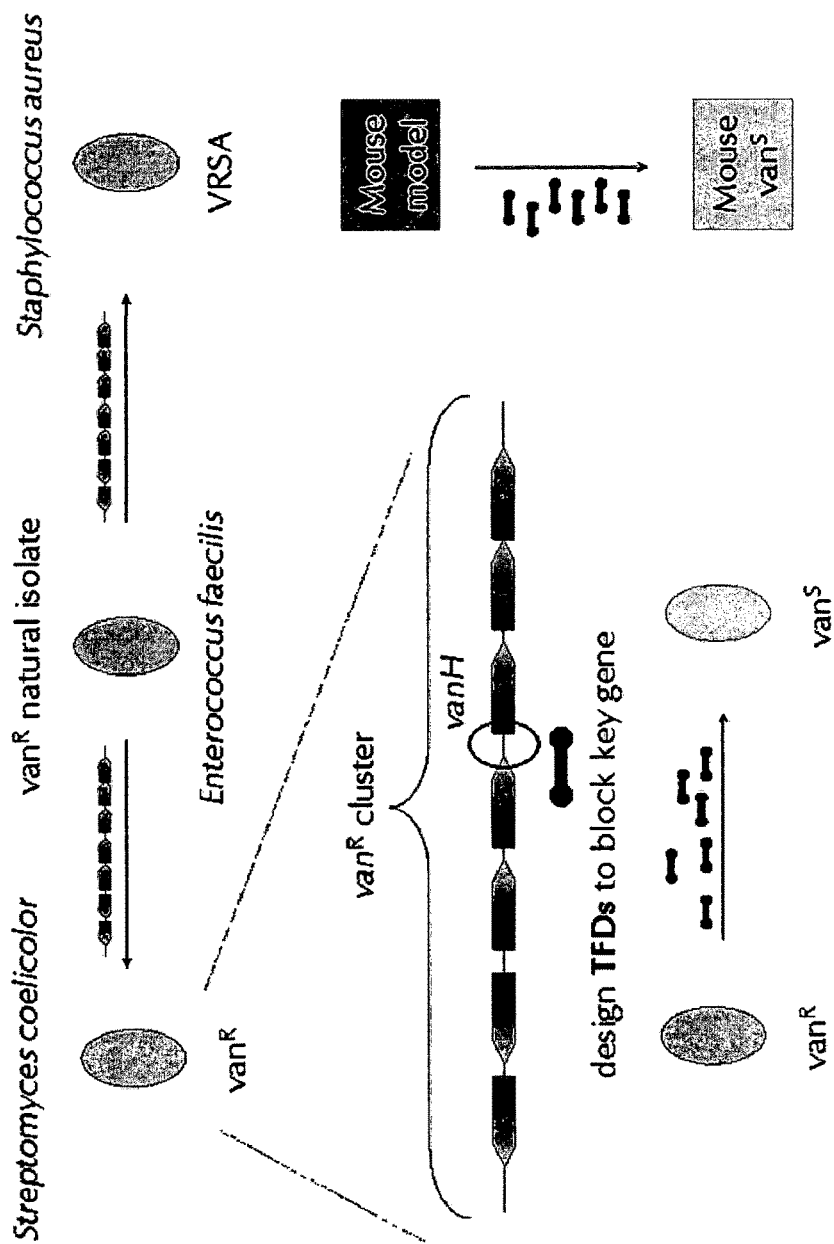
FIG. 20 provides application of the transcription factor decoy (TFD) approach to combating antibiotic resistance. The schematic demonstrates how TFDs are used to counter known resistance mechanisms in pathogenic bacteria. Resistance to the prescribed antibiotic vancomycin is used as an example.

The overall approach taken to identify a decoy capable of altering susceptibility to vancomycin, or indeed other antibiotic resistance mechanisms that have been characterized at the genetic level, is presented in FIG. 20. This schematic demonstrates how TFDs are used to counter known resistance mechanisms in pathogenic bacteria. Resistance to the prescribed antibiotic vancomycin is used as an example. This occurs in strains of *Entercoccus faecium*, a human pathogen, and *Streptomyces coelicolor*. In both bacteria resistance is encoded by the vanHAX operon which is induced by the VanR protein. By designing decoys to interfere with the binding of VanR to its cognate site in the genome it is possible to prevent induction of vanHAX and so render the bacteria susceptible to vancomycin. In this example decoys are functionally validated in bacterial (non-pathogenic) models containing similar resistance mechanisms to the pathogens or the actual mechanisms moved into the model by horizontal gene transfer. Subsequently the decoy is tested on pathogenic models, such as clinical isolates and finally moved to animal models, such as mice infected with vancomycin resistant *Entercoccus* (VRE) or vancomycin resistant *S. aureus*. It should be appreciated that the approach could be applied to a broad range of bacterial phenotypes which are controlled by such genetic switches. These include, but would not be limited to the discovery of other decoys or combinations of decoys that could render bacteria susceptible to other antibiotics such as penicillin, chloramphenicol, tetracycline, daptomycin, etc.

Figure 21:
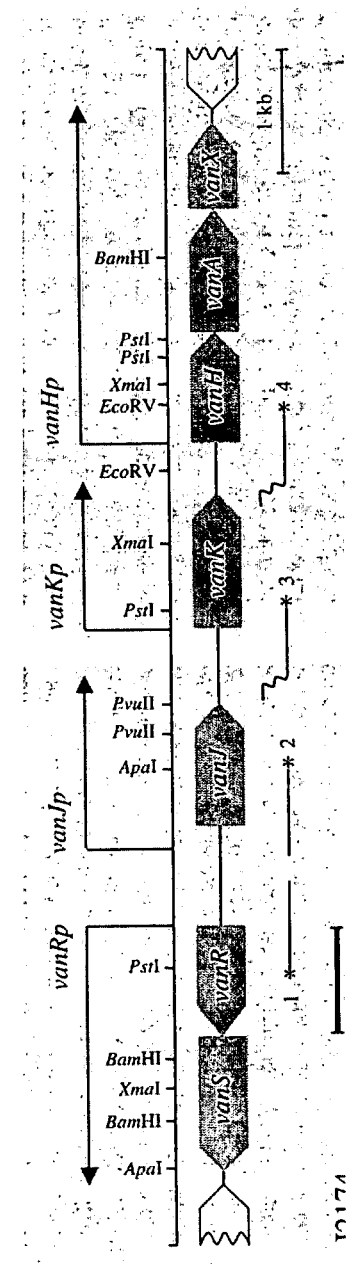
FIG. 21. The structure of the vancomycin gene. From Hong et al. 2004 *Molecular Microbiology* 52: 1107-1121.

The structure of the vancomycin resistance operon in *Streptomyces coelicolor* is shown in FIG. 21 (From Hong et al. 2004 Molecular Microbiology 52: 1107-1121). The vancomycin operons consist of four operons, as indicated by the arrows. The vanRS operon encodes a two component regulatory system that acts to sense the presence of vancomycin (directly or indirectly) and induce the expression of the vanHAX operon which encodes the vancomycin resistance mechanism. The vanHAX operon is induced by the phosphorylated version of VanR binding within its promoter, VanS in turn is the kinase that phosphorylates VanR on detection of vancomycin. We expect our decoy to disrupt the binding of phosphorylated VanR to the site in vanH promoter.

It should be noted that the evolutionary source of the resistance genes in *Entercoccus faecalis*, which is the cause of some of the vancomycin-resistant infections seen in the clinic is thought to be a vancomycin-producing actinomycete.

The sequence of the vanH5 decoy used is shown below, with the binding site for phosphorylated VanR capitalized:

```
                                          SEQ ID. NO. 21
5'-P- ata tctatatgaa gcgacgtggt cgatgagccg cagcg tttt cgctg CGG CTC ATC GAC CAC GTC GCT TCA TAT AGA tatag tttt ct- 3'
```

Figure 22:
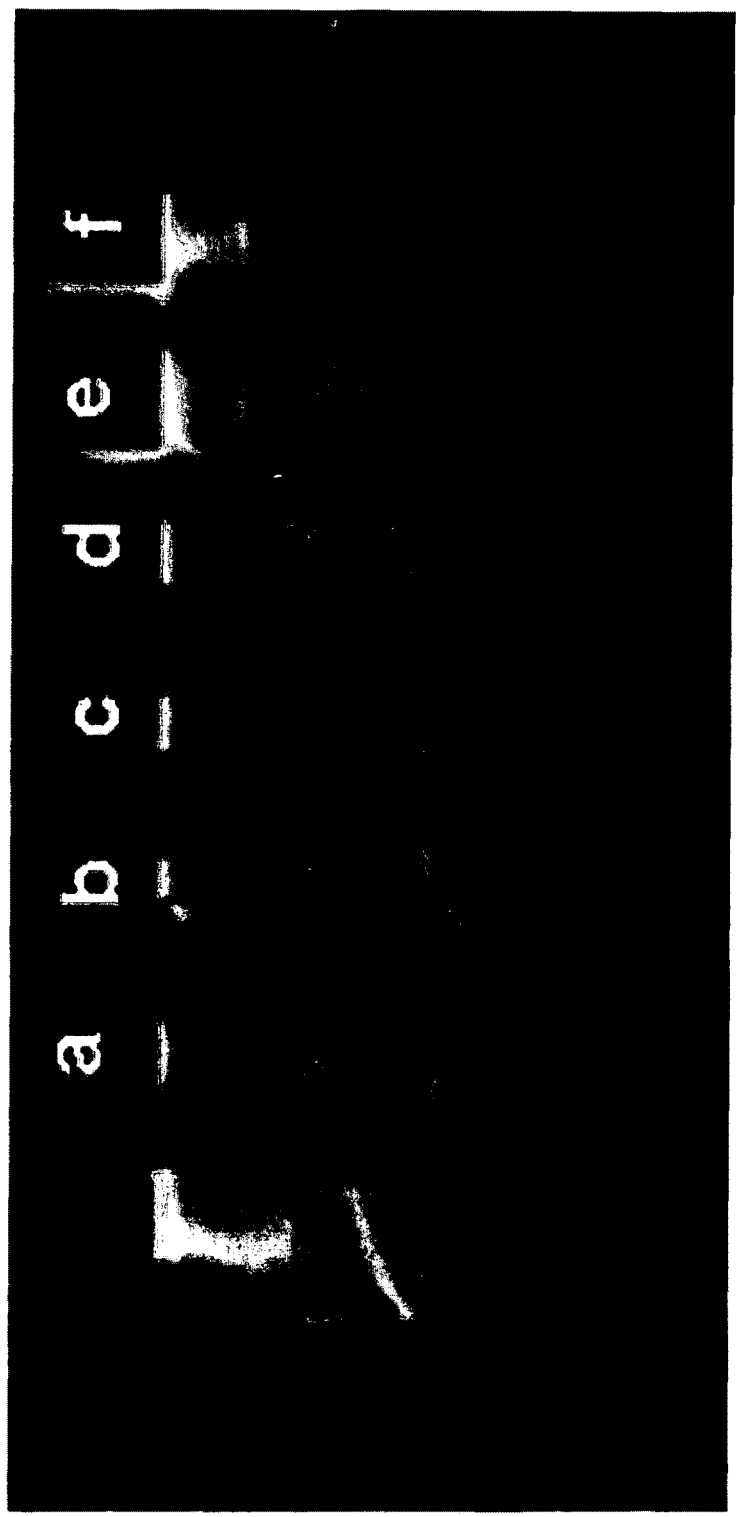
FIG. 22. Evidence of cyclization of the oligonucleotide decoy vanH5. The oligonucleotide was resuspended at a final concentration of 100 pmol/ul in a T4 DNA ligase buffer (as supplied by the manufacturer of the enzyme, New England Biolabs) and 400 U of T4 DNA ligase and incubated at 16 degrees Centigrade for various times.

The oligonucleotide was prepared as a circular dumbbell decoy as shown in FIG. 22. The oligonucleotide was resuspended at a final concentration of 100 pmol/ul in a T4 DNA ligase buffer (as supplied by the manufacturer of the enzyme, New England Biolabs) and 400 U of T4 DNA ligase and incubated at 16 degrees Centigrade for various times. During incubation the oligonucleotide formed a stem-loop structure which, due to the activity of the ligase, can become converted into a covalently joined single-stranded 'circular' molecule of DNA. The extent of this cyclization is dependent upon the incubation time with ligase; the longest incubation (16 h) led to near complete conversion. Hence, following incubation of the oligonucleotide with T4 DNA ligase for 0, 1, 2, 4, 6 and 16 h (a-f respectively), aliquots were taken from each reaction, heat treated to inactivate the enzyme and the DNA was recovered by ethanol precipitation before being analyzed by 6% polyacrylamide gel electrophoresis and vizualization with ethidium bromide staining. Lanes a-f show conversion of slower migrating linear single-stranded DNA molecule into a circular dumbbell closed circular duplex which migrates at higher rate, (lane f).

The decoy is in a 'circular dumbbell' configuration (Ahn J D, Kim C D, Magae J, Kim Y H, Kim H J, Park K K, Hong S, Park K G, Lee I K, Chang Y C (2003) Biochemical Biophysical Res Comm 310:1048-1053), although this is not required. Other forms of oligodeoxynucleotide may be used, including but not limited to, for example (a) longer double stranded oligodeoxynucleotides comprising this sequence, such that exonucleases would need to substantially reduce the length of the oligonucleotide before loss of decoy function; (b) oligodeoxynucleotides comprising modified bases or sugars to confer greater nuclease resistance; (c) 2'-OH nucleotides or amines attached to the termini of the oligonucleotides, which would block exonuclease activity (which is all the dumbbells are doing); (d) small circular double-stranded DNA molecules; or (e) multimeric molecules comprising multiple copies of the active decoy sequence.

Essentially, what is required is that the ODN used has a double stranded region incorporating the targeted sequence within the vanH promoter bracketed by small stem loop structures, or other sequences. For the circular dumbbell structure, the molecule is synthesized as a linear oligonucleotide and cyclized by incubation with T4 DNA ligase.

Figure 23:
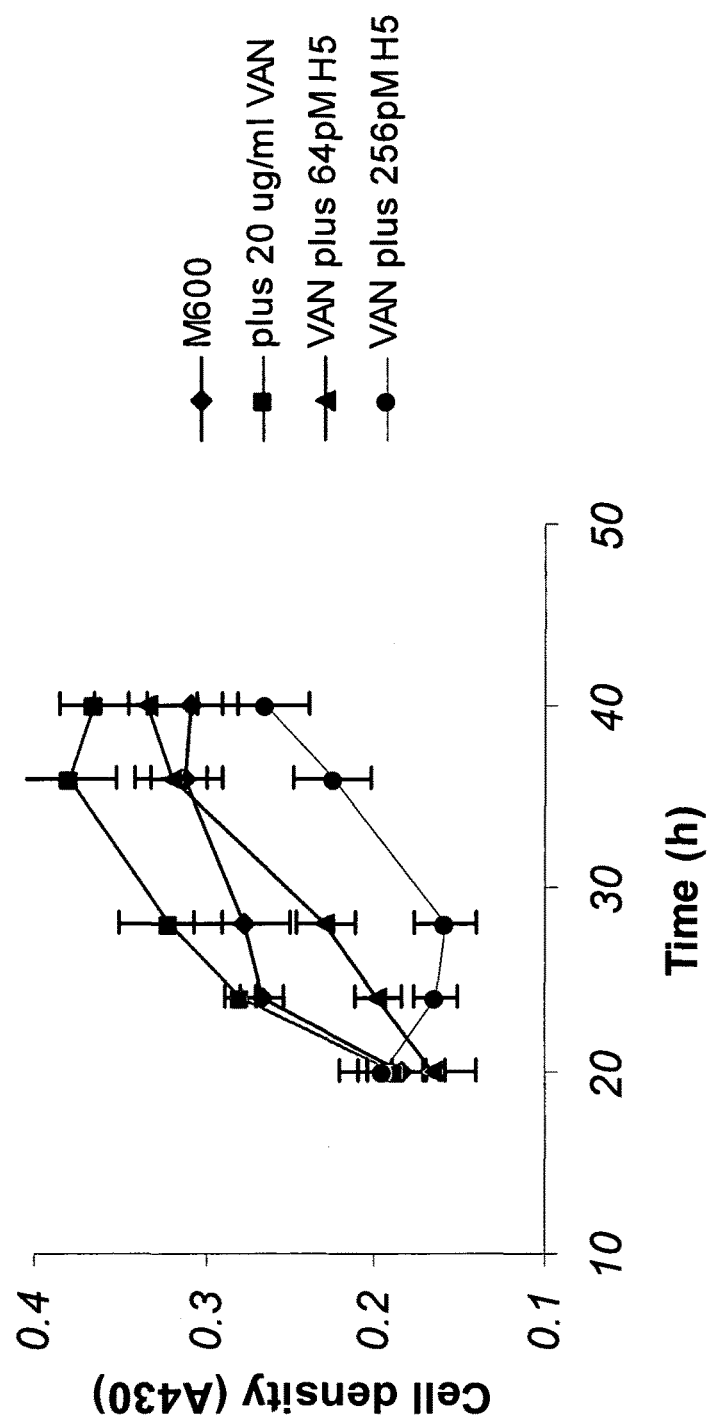
FIG. 23. Shows the effect of incubating a vancomycin resistant bacterium with and without increasing levels of the vanH5 decoy. *S. coelicolor* strain M600 was grown in liquid MMCGT medium (Molecular Microbiology 52: 1107-1121), growth was measured by recording the absorbance of the culture at 430 nm (Cell Density) and plotted as a function of time of incubation.

A diagram showing the introduction of a decoy called vanH5 into a liquid culture of *Streptomyces coelicolor* strain M600 is given in FIG. 23. *S. coelicolor* strain M600 was grown in liquid MMCGT medium (Molecular Microbiology 52: 1107-1121), growth was measured by recording the absorbance of the culture at 430 nm (Cell Density) and plotted as a function of time of incubation. Growth of four cultures was monitored: (1) with nothing added to the media (diamonds 'M600'); (2) the media supplemented with a sub-lethal concentration of 20 µg/ml of the antibiotic vancomycin at 0 h (squares 'plus 20 µg/ml VAN); as in (2) but with the decoy oligonucleotide H5 added to a final concentration of 64 µM following 20 h of incubation (triangles 'VAN plus 64 pM H5'); as in (2) but with the decoy oligonucleotide H5 added to a final concentration of 256 pM following 20 h of incubation (circles 'VAN plus 256 pM H5').

From this data, it is evident that M600 grows comparably well in the presence or absence of 20 ug/ml vancomycin (added or not added at the start of the culture process), confirming that the strain has resistance to vancomycin. In the presence of 20 ug/ml vancomycin, the addition of the cyclized decoy vanH5 to a final concentration of 64 pM has little detectable effect, while addition to 256 pM causes the cells to cease growing over a period of approximately 18 h. This may colloquially be referred to as a "therapeutic window", where the decoys have entered the cells, have interfered with the binding of the vanR regulator to the vanH promoter, and thereby prevented the induction of the resistance mechanism. After 18 h, our evidence from other systems suggests, degradation of the decoys (by endonucleases within the cell) occurs, which may affect their efficacy.

As for why the vanH decoy seemingly has a bacteriostatic effect, we believe this is due to the mechanism of resistance being a modification to the bacterial cell wall which prevents the action of vancomycin. When vancomycin is added to the culture, this is at the beginning of the experiment. The decoy is added at 20 hours. At this point, the bacteria will have been growing with a modified cell wall. Upon addition of the decoy, from that point on until the decoy is dissipated, the ability to modify the bacterial cell wall is blocked. As a result, any new bacterial growth is rendered sensitive to vancomycin, although older cells are able to persist. Upon depletion of the decoy, the persistent cells with residual vancomycin resistance are able to once again proliferate. Adding the decoy prior to the vancomycin would have little effect, as the resistance operon is not on. We anticipate, however, that administration of the decoy ODNs at the same time induces a bacteriocidal effect.

Thus, this example demonstrates sensitivity of *S. coelicolor* to vancomycin in the presence of the TFD's and not in their absence. This would be accepted by those skilled in the art as an acceptable surrogate for demonstrating this effect in a pathogen, such as *E. faecalis*. The *E. faecium* van operon is induced by the same mechanism (vanR binding to vanH), even though homology on a sequence level between the two systems is not very high. Those skilled in the art would be able to easily modify the decoy sequence for use in the pathogen.

The vanH5 decoy is one example of oligodeoxynucleotides which can bind to a prokaryotic transcription factor such that binding of the transcription factor to its cognate target in the genome of the prokaryote is diminished or obliterated.

2. Designing TFDs to Combat Antibiotic Resistance in Pathogens

The principle of how TFDs can be used to restore vancomycin sensitivity has been discussed above. For situations where the genes responsible are unknown, the universal n[snare] libraries or custom libraries created from the genomic DNA of the pathogen provided by this invention are used. As shown in FIG. 6 the library can either be introduced into the pathogenic bacteria under laboratory conditions or the genetic elements determining resistance can be cloned and introduced into a non-pathogenic laboratory strain to act as a model system, which can then be transformed. The cells will then be cultured in the absence of the chosen antibiotic and the library introduced into the cells by transformation whilst in liquid culture, the sample is now split and the antibiotic added to half of the sample and incubation continued. The populations of cells are recovered and the concatamerized TFDs amplified from the plasmids by PCR. These two populations are subtracted to isolate the TFDs missing from the antibiotic-treated sample, and hence those that conferred sensitivity. This enriched population of TFDs is recloned and the selection process repeated until it is sufficiently enriched in TFDs capable of rendering the cell antibiotic sensitive.

Potential targets for such an approach would include investigation of the mechanisms of resistance to many of the clinically prescribed antibiotics, and future ones for which antibiotic resistance begins to limit their efficacy. Examples of the current antibiotics that would be considered for investigation using the n[snare] methodologies and subsequent treatment with TFDs to defeat antibiotic resistance would include: those from the class of antibiotics known as aminoglycosides (such as kanamycin); from the carbapenems (such as meropenem); the cephalosporins (such as cefepime); the glycopeptides (such as vancomycin and daptomycin); the penicillins (such as ampicillin, carbenicillin and penicillin); the polypeptide antibiotics (such as polymixcin B); the quinolines (such as levaquin); the sulfonamides (such as Bactrim); the tetracyclines (such as tetracycline); and variously, chloramphenicol, rifampicin, Zyvox.

Example 7

7.1 Cholesterol Labeled TFDs in the Presence of Streptolysin-O

Using oligonucleotide primers, one of which has a 5' cholesterol modification and the other a similar modification at its 5' end or some other (such as a fluorescent dye, such as Cy5, so that the uptake of the TFD can be easily measured) a TFD is prepared by PCR. If the TFD has been previously cloned into a vector (pGEMT-Easy) the primers are designed to anneal to the vector sequences immediately flanking the insert, for example:

```
Chol_TEf:
                                        SEQ ID NO: 22
5' Cholesterol-TEG-ggc cgc cat ggc ggc cgc ggg aat tc Cy5_TEr:
                                        SEQ ID NO: 23
5' Cy5- AGG CGG CCG CGA ATT CAC TAG TG.
```

If the sequence to be used for a TFD has not been cloned it may either be directly synthesized (if short enough) and annealed to form the TFD, or amplified directly from genomic DNA using primers designed to anneal within the TFD.

The PCR product is ethanol precipitated and resuspended in TE buffer at a concentration of 500-1000 ng/µl. Typically antibiotic sensitivity assays are performed using 96 well plates, each well containing 200 ml of broth. For example, in the case of *Enterococcus faecium* this broth is BHI media (from Becton Dickinson) supplemented with 0.2 U/ml Streptolysin-O (Sigma) and 5 µg/ml of vancomycin antibiotic and inoculated with a vancomycin-resistant strain of *E. faecium*.

7.2 Preparation of Dumbbells by PCR

Dumbbell decoys are covalently closed single stranded DNA characterised by a double-stranded centre, containing the binding site for the targeted factor, flanked by stem-loop structures. The stem-loops stabilize the decoy by preventing action of exonucleases which would otherwise degrade the decoy polynucleotide. Hence Dumbbell decoys (DB) are so called because of their characteristic shape.

DBs are prepared by PCR using as a template a pGEMTEasy-derived plasmid containing the targeted binding site, as described in 7.1. The primers used in amplification are:

```
DBTEf:
                                        (SEQ ID NO: 24)
5' P- CTTGG TTTTT CCAAG AGAAGAGC ccg cca tgg cgg ccg cgg gaa ttc DBTEr:
                                        (SEQ ID NO: 25)
P- CCG TCT TTT TGA CGG CGA AGA GCA GGC GGC CGC

GAA TTC ACT AGT GA.
```

The portion of the primers which will form the stem-loops are underlined. Amplification with the appropriate vector gives the DNA product shown in FIG. 24 (SEQ ID NO:28 and SEQ ID NO:29, in the top portion of the Figure), where the portion of the DB which will bind to the transcription factor is given by 'NNN NNN'. The sequences in bold represent a binding site for the nicking restriction enzyme Nt.BspQ1. In the second part of FIG. 24 the consequence of digesting the PCR product with Nt.BspQ1 is shown (SEQ ID NO:30 and SEQ ID NO:31); this exposes the stem-loop structures as single stranded regions which will form a stem-loop and can subsequently be ligated by treatment with T4 DNA ligase to form a covalently closed circle and DB.

7.3 Preparation of Dumbbell Oligonucleotides by Restriction Digest of Plasmid

Alternatively DBs can be made by cloning the blunted PCR product shown in FIG. 24 into a suitable PCR-cloning vector, such as pGEMTEasy, confirming its identity and preparation of the plasmid. The plasmid can then be digested to release the insert which is additionally digested with Nt.BspQ1 to release the fragment shown in the second portion of FIG. 24. This can be similarly treated with T4 DNA ligase in order to covalently close the DNA molecule and form a DB.

The advantage of this approach is that is more amenable, both practically and economically, to scaling up should the DB be required in large quantities.

7.4 Transfection with R9-Cholesterol Agent.

R9-cholesterol has been described for its properties of aiding transfection of siRNA (or other nucleic-acid based therapy) molecules and the like in eukaryotic cells (US Patent: 20070207966). Here we describe its utility in transfecting various bacteria with TFDs.

R9-cholesterol, which consists of a cholesterol molecule attached to a linear chain of nine D-arginines, was synthesized as previously described (Kim W. J., et al., Mol. Ther. 2006 14: 343-350). TFDs were mixed with increasing amounts of R9-cholesterol in a TE based buffer supplemented with 5% glucose. The mixture was incubated at room temperature for 1 hour and then either used directly in transfections or analysed by agarose gel electrophoresis. Typically the minimum amount of R9-cholesterol was used that caused the complex with DNA not to run in the gel; i.e. the charge of the nucleic acid backbone had been neutralized by binding of poly-arginine. The cholesterol molecule helps the TFD associate with the bacterial membrane and so enter the cell.

TFD/R9-cholesterol conjugates were mixed at various concentrations into 200 µl of culture in a 96 well plate. For example, in the case of *Enterococcus faecium* this broth is BHI media (from Becton Dickinson) supplemented with 0.2 U/ml Streptolysin-O (Sigma) and 5 µg/ml of vancomycin antibiotic and inoculated with a vancomycin-resistant strain of *E. faecium*.

Example 8

Use of a Van Decoy Sequence to Sensitize *Enterococcus faecium* to Vancomycin

8(a) Using Cholesterol Labeled TFDs in the Presence of Streptolysin-O

Cholesterol/Cy5-labeled decoy polynucleotides were prepared as in Example 7.1. The assays were performed using 96 well plates, each well containing 200 ml of broth consisting of BHI media (from Becton Dickinson) supplemented with 0.2 U/ml Streptolysin-O (Sigma) and 5 µg/ml of vancomycin antibiotic and inoculated with a vancomycin-resistant strain of *E. faecium*.

1 µl of various concentrations of a Cholesterol/Cy5-labeled decoy were added to each well and their effect on bacterial growth of *E. faecium* monitored by measuring absorbance of the broth at intervals during incubation. The plates were incubated at 37° C. with shaking and absorbance readings (at 450 nM) were taken using a plate reader. Two decoys were tested: VAN contains the regulatory element controlling induction of VanA-type antibiotic resistance; CON is a decoy sequence that does not occur in the *E. faecium* genome and was used as a negative control. The sequence of the VAN decoy sequence (that part cloned into pGEMT-Easy vector to create a plasmid used in the PCR amplification step with the Chol_TEf and Cy5_TEr primers) was:

```
                                         (SEQ ID NO: 26)
VAN TFD 5' AAA AAA GAA TCA TCA TCT TAA GAA ATT

CTT AGT CAT TTA 3'
```

Figure 25:
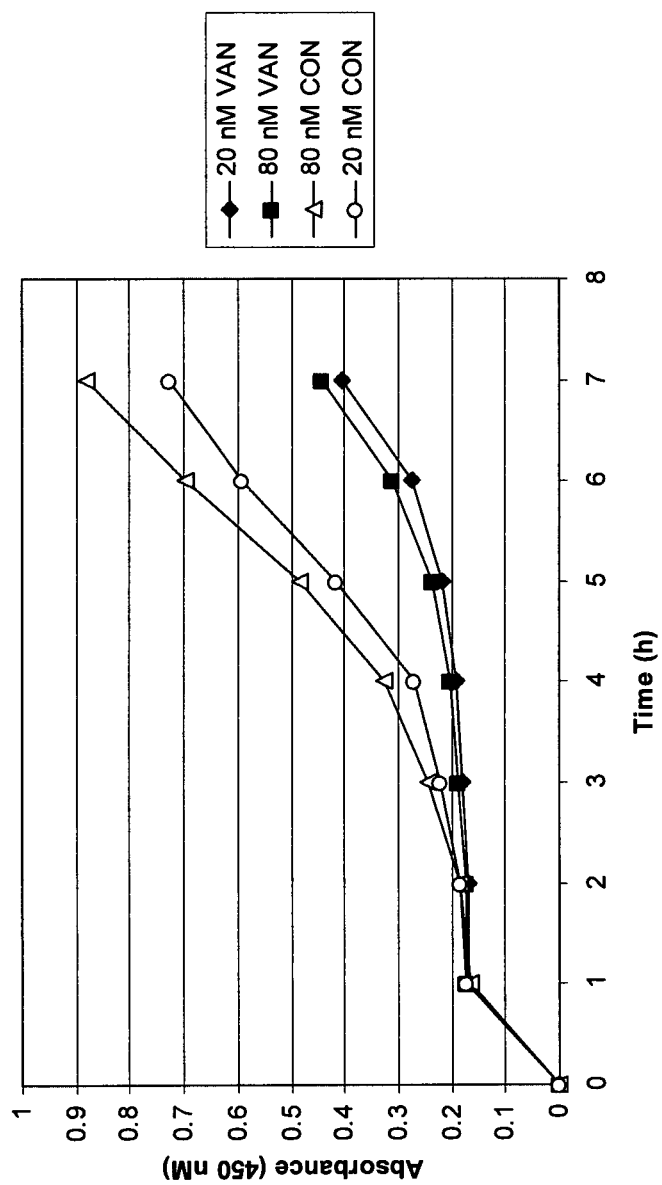
FIGS. 25 & 26. Show growth curves for *E. faecium* grown in the presence of vancoymcin after treatment with either the VAN transcription factor decoy sequence or a negative control (CON), as described in Examples 8(a) and 8(b) respectively.

The resultant growth curves are shown in FIG. 25. All data points were performed in triplicate. It is evident that treatment with the VAN TFD at concentrations as low as 40 nM resensitized the *E. faecium* strain to vancomycin, whereas the CON negative control had no effect. Uptake of TFDs was confirmed with qPCR and fluorescence microscopy.

8(b) Using Transfection with R9-Cholesterol Agent

The array used a 96 well plate, each well containing 200 ml of culture, consisting of BHI media (from Becton Dickinson) supplemented with 0.2 U/ml Streptolysin-O (Sigma) and 5 µg/ml of vancomycin antibiotic and inoculated with a vancomycin-resistant strain of *E. faecium*.

1 µl of various concentrations of the TFD/R9-cholesterol conjugates were added to each well and their effect on bacterial growth monitored by measuring absorbance of the broth at intervals during incubation. The plates were incubated at 37° C. with shaking and absorbance readings (at 595 nM) were taken using a plate reader. Two Dumbbell TFDs were tested: VAN contains the regulatory element controlling induction of VanA-type antibiotic resistance (containing the same sequence as Seq. 26); CON is a decoy sequence that does not occur in the *E. faecium* genome and was used as a negative control (containing the same sequence as CON in Example 8(a)).

Figure 26:
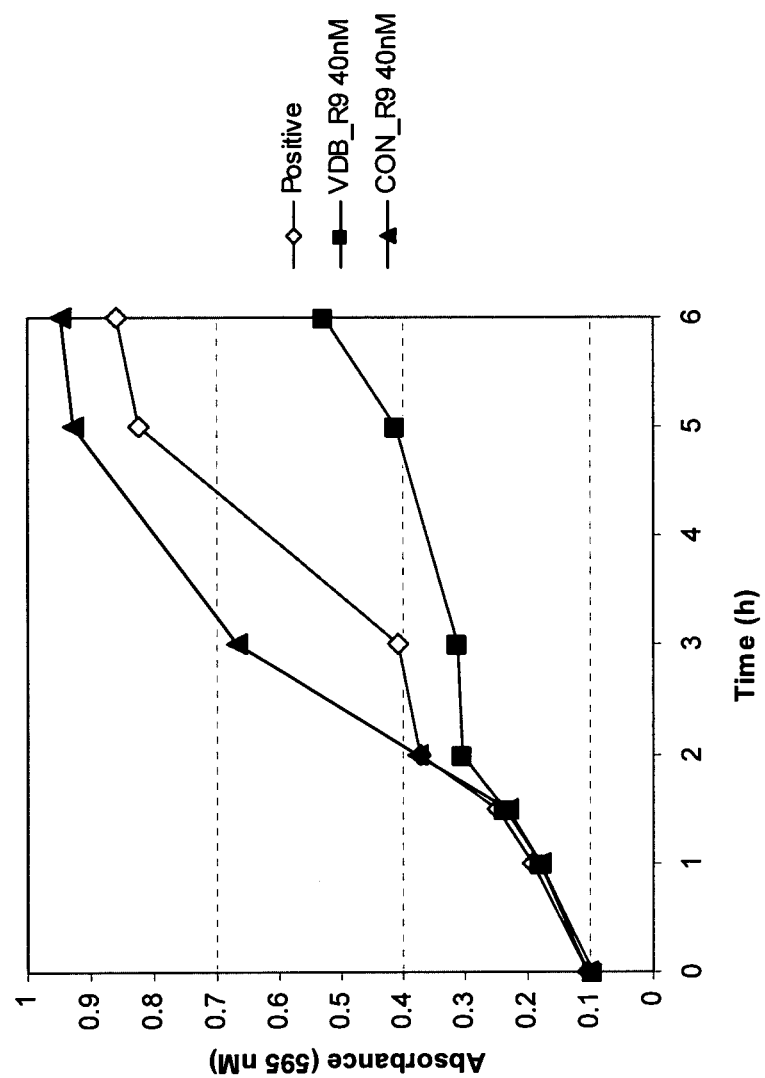

The resultant growth curves are shown in FIG. 26. All data points were performed in triplicate. It is evident that treatment with the VAN TFD at concentrations as low as 40 nM resensitized the *E. faecium* strain to vancomycin, whereas the negative control had no negative impact on cell growth.

The invention claimed is:

1. A decoy polynucleotide comprising a sequence comprising a binding site for a cis-regulatory factor, wherein the binding site is not operably linked to a gene, and wherein the cis-regulatory factor is a regulator of expression of one or more antibiotic resistance genes in a prokaryote,
wherein the decoy polynucleotide causes reduction in the expression of the one or more antibiotic resistance genes and reduces antibiotic resistance of the prokaryotic cell; and
wherein the decoy polynucleotide is a linear oligonucleotide with at least one element of secondary structure to increase nuclease resistance of the polynucleotide,
wherein the at least one element of secondary structure is a stem-loop structure and wherein sequence comprising the transcription factor binding site is adjacent to heterologous sequence.

2. A decoy polynucleotide according to claim 1, wherein the one or more antibiotic resistant genes is resistant to an antibiotic selected from one or more: the aminoglycosides;

the carbapenems; the cephalosporins; the glycopeptides; the penicillins; the polypeptide antibiotics; the quinolines; the sulfonamides; or the tetracyclines.

3. A decoy polynucleotide according to claim 1, wherein the prokaryote is:
(a) a gram positive bacterium of a genus selected from: *Actinomyces; Streptomyces;* Mycobacteria; *Clostridium; Bacillus; Listeria; Staphylococcus; Streptococcus;* and *Enterococcus;* or (b) a gram negative bacterium of a genus selected from:
Enterobacteriaceae; *Pseudomonas; Moraxella; Helicobacter; Stenotrophomonas; Bdellovibio,* Acetic acid bacteria; *Legionella;* Cyanobacteria; Spirochaetes; Green Sulphur bacteria; and Green Nonsulphur bacteria.

4. A decoy polynucleotide according to claim 1, wherein the prokaryote is a vancomycin resistant pathogen or a non-pathogenic model of vancomycin resistance.

5. A decoy polynucleotide according to claim 1, wherein the decoy polynucleotide comprises: more than one copy of the transcription factor binding site.

6. A decoy polynucleotide according to claim 1, wherein the transcription factor binding site in the decoy polynucleotide comprises the sequence of SEQ ID NO: 21 or SEQ ID NO: 26.

7. A decoy polynucleotide according to claim 1, wherein the prokaryote is selected from: *Mycobacterium tuberculosis; Mycobacterium bovis; Mycobacterium africanum; Mycobacterium microti; Mycobacterium leprae; Clostridium difficile; Clostridium botulinum; Clostridium perfingens; Clostridium tetani; Salmonella* sp.; *Escherichia coli; Enterococcus faecium; Enterococcus faecalis; Neisseria gonorrhoeae; Neisseria meningitides; Moraxella catarrhalis; Hemophilus influenza; Kebsiella pneumoniae; Legionella pneumophila; Pseudomonas aeruginosa; Proteus mirabilis; Enterobacter cloacae; Serratia marcescens; Helicobacter pylori; Salmonella enteritidis;* and *Salmonella typhi.*

* * * * *

SEQUENCE LISTING

```
<160> NUMBER OF SEQ ID NOS: 31

<210> SEQ ID NO 1
<211> LENGTH: 47
<212> TYPE: DNA
```

<213> ORGANISM: Artificial Sequence
<220> FEATURE:
<223> OTHER INFORMATION: Synthetic sequence: Decoy oligonucleotide
      containing the AfsR binding site

<400> SEQUENCE: 1
aatacgactc actatagggg cgttgagcga acgttttcg cggccgc                    47

<210> SEQ ID NO 2
<211> LENGTH: 23
<212> TYPE: DNA
<213> ORGANISM: Artificial Sequence
<220> FEATURE:
<223> OTHER INFORMATION: Synthetic sequence: Joining polynucleotide
      R-T7, which contains a partial complement of a commonly used
      primer, T7

<400> SEQUENCE: 2
ccctatagtg agtcgtattg cgg                                             23

<210> SEQ ID NO 3
<211> LENGTH: 64
<212> TYPE: DNA
<213> ORGANISM: Artificial Sequence
<220> FEATURE:
<223> OTHER INFORMATION: Synthetic sequence: Oligonucleotide containing
      the AfsR binding site and used to create a cyclised decoy sequence

<400> SEQUENCE: 3
atagcgttga gcgaacgttt ttcgcgtttt cgcgaaaaac gttcgctcaa cgctatagtt    60
ttct                                                                 64

<210> SEQ ID NO 4
<211> LENGTH: 43
<212> TYPE: DNA
<213> ORGANISM: Artificial Sequence
<220> FEATURE:
<223> OTHER INFORMATION: Synthetic sequence: Strand of a double stranded
      adaptor molecule

<400> SEQUENCE: 4
ggtccgggcc acggtggtct acgagcctca gccaggtccg act                      43

<210> SEQ ID NO 5
<211> LENGTH: 15
<212> TYPE: DNA
<213> ORGANISM: Artificial Sequence
<220> FEATURE:
<223> OTHER INFORMATION: Synthetic sequence: Strand of a double stranded
      adaptor molecule

<400> SEQUENCE: 5
gtcggacctg gctga                                                     15

<210> SEQ ID NO 6
<211> LENGTH: 39
<212> TYPE: DNA
<213> ORGANISM: Artificial Sequence
<220> FEATURE:
<223> OTHER INFORMATION: Synthetic sequence: Bbv complementary
      oligonucleotide

<400> SEQUENCE: 6
ggacctggct gaggctcgta gaccaccgtg gcccggacc                           39

<210> SEQ ID NO 7

```
<211> LENGTH: 36
<212> TYPE: DNA
<213> ORGANISM: Artificial Sequence
<220> FEATURE:
<223> OTHER INFORMATION: Synthetic sequence: An oligonucleotide
      comprising a NotI site and a randomised nucleotide sequence
<220> FEATURE:
<221> NAME/KEY: misc_feature
<222> LOCATION: (20)..(28)
<223> OTHER INFORMATION: n is a, c, g, or t

<400> SEQUENCE: 7
aatacgactc actatagggn nnnnnnnngc ggccgc                               36

<210> SEQ ID NO 8
<211> LENGTH: 54
<212> TYPE: DNA
<213> ORGANISM: Artificial Sequence
<220> FEATURE:
<223> OTHER INFORMATION: Synthetic sequence: Decoy oligonucleotide
      designed based on cis-regulatory sequence A24.1

<400> SEQUENCE: 8
atatcactct cgatgtcggc gttttcgccg acatcgagag tgatatagtt ttct          54

<210> SEQ ID NO 9
<211> LENGTH: 54
<212> TYPE: DNA
<213> ORGANISM: Artificial Sequence
<220> FEATURE:
<223> OTHER INFORMATION: Synthetic sequence: Decoy oligonucleotide
      designed based on cis-regulatory sequence A24.2

<400> SEQUENCE: 9
atatcaggaa tgccagatgc gttttcgcat ctggcattcc tgatatagtt ttct          54

<210> SEQ ID NO 10
<211> LENGTH: 52
<212> TYPE: DNA
<213> ORGANISM: Artificial Sequence
<220> FEATURE:
<223> OTHER INFORMATION: Synthetic sequence: Decoy oligonucleotide
      designed based on cis-regulatory sequence A24.3

<400> SEQUENCE: 10
atactgcctc tcggtaagcg ttttcgctta ccgagaggca gtatagtttt ct            52

<210> SEQ ID NO 11
<211> LENGTH: 54
<212> TYPE: DNA
<213> ORGANISM: Artificial Sequence
<220> FEATURE:
<223> OTHER INFORMATION: Synthetic sequence: Decoy oligonucleotide
      designed based on cis-regulatory sequence A24.4

<400> SEQUENCE: 11
atatgcagct cgctgcacgc gttttcgcgt gcagcgagct gcatatagtt ttct          54

<210> SEQ ID NO 12
<211> LENGTH: 54
<212> TYPE: DNA
<213> ORGANISM: Artificial Sequence
<220> FEATURE:
<223> OTHER INFORMATION: Synthetic sequence: Decoy oligonucleotide
      designed based on cis-regulatory sequence A24.5

<400> SEQUENCE: 12
ataaatctgt tgagtagggc gttttcgccc tactcaacag atttatagtt ttct          54
```

<210> SEQ ID NO 13
<211> LENGTH: 54
<212> TYPE: DNA
<213> ORGANISM: Artificial Sequence
<220> FEATURE:
<223> OTHER INFORMATION: Synthetic sequence: Decoy oligonucleotide
      designed based on a scrambled A24.5 sequence

<400> SEQUENCE: 13
atagcaattt agatggtggc gttttcgcca ccatctaaat tgctatagtt ttct        54

<210> SEQ ID NO 14
<211> LENGTH: 24
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 14
cgacatcgag agtgatatag tttt                                         24

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 15
gccgacatcg agagtgatat                                              20

<210> SEQ ID NO 16
<211> LENGTH: 21
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 16
tgtcgccccc aggagacgga g                                            21

<210> SEQ ID NO 17
<211> LENGTH: 24
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 17
cttaaatcct cgaaggcgac ccag                                         24

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 18
tcctcgagcc ggttctcctc g                                            21

<210> SEQ ID NO 19
<211> LENGTH: 18
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 19
gctggtggac atcggtct                                                 18

<210> SEQ ID NO 20
<211> LENGTH: 19
<212> TYPE: DNA
<213> ORGANISM: Artificial Sequence
<220> FEATURE:
<223> OTHER INFORMATION: Synthetic sequence: PCR primer used in
      quantitative PCR

<400> SEQUENCE: 20
gccggtactt gtcgctctc                                                19

<210> SEQ ID NO 21
<211> LENGTH: 88
<212> TYPE: DNA
<213> ORGANISM: Artificial Sequence
<220> FEATURE:
<223> OTHER INFORMATION: Synthetic sequence: A vanH5 decoy
      oligonucleotide containing a binding site for phosphorylated VanR

<400> SEQUENCE: 21
atatctatat gaagcgacgt ggtcgatgag ccgcagcgtt ttcgctgcgg ctcatcgacc    60
acgtcgcttc atatagatat agttttct                                      88

<210> SEQ ID NO 22
<211> LENGTH: 26
<212> TYPE: DNA
<213> ORGANISM: Artificial Sequence
<220> FEATURE:
<223> OTHER INFORMATION: Synthetic sequence: Oligonucleotide primer used
      for amplification of a target sequence from the pGEMT-Easy vector

<400> SEQUENCE: 22
ggccgccatg gcggccgcgg gaattc                                        26

<210> SEQ ID NO 23
<211> LENGTH: 23
<212> TYPE: DNA
<213> ORGANISM: Artificial Sequence
<220> FEATURE:
<223> OTHER INFORMATION: Synthetic sequence: Oligonucleotide primer used
      for amplification of a target sequence from the pGEMT-Easy vector

<400> SEQUENCE: 23
aggcggccgc gaattcacta gtg                                           23

<210> SEQ ID NO 24
<211> LENGTH: 47
<212> TYPE: DNA
<213> ORGANISM: Artificial Sequence
<220> FEATURE:
<223> OTHER INFORMATION: Synthetic sequence: Oligonucleotide primer used
      for amplification of a target sequence from the pGEMT-Easy vector
      in the production of dumbbell decoys

<400> SEQUENCE: 24
cttggttttt ccaagagaag agcccgccat ggcggccgcg ggaattc        47

<210> SEQ ID NO 25
<211> LENGTH: 47
<212> TYPE: DNA
<213> ORGANISM: Artificial Sequence
<220> FEATURE:
<223> OTHER INFORMATION: Synthetic sequence: Oligonucleotide primer used
      for amplification of a target sequence from the pGEMT-Easy vector
      in the production of dumbbell decoys

<400> SEQUENCE: 25 ccgtctttt gacggcgaag agcaggcggc cgcgaattca ctagtga        47

<210> SEQ ID NO 26
<211> LENGTH: 39
<212> TYPE: DNA
<213> ORGANISM: Artificial Sequence
<220> FEATURE:
<223> OTHER INFORMATION: Synthetic sequence: VAN decoy sequence
      containing the regulatory element controlling induction of VanA
      type resistance in E. faecium.

<400> SEQUENCE: 26
aaaaaagaat catcatctta agaaattctt agtcattta        39

<210> SEQ ID NO 27
<211> LENGTH: 300
<212> TYPE: DNA
<213> ORGANISM: Streptomyces coelicolor

<400> SEQUENCE: 27
tcactctcga tgtcggccgg tggatgtggt ggccgcaccc gctcgcccgg cgcgaggacc        60
cttccgagga cccagccgta tcaggaatgc cagattctat tgattcggaa gcctcgacca       120
ctgcctctcg gtaaaatcca gcaaaaatta atcagtgcag ctcgctgcac tgattaattt       180
ttgatcaata ggagatcgct tgtgacggca agcacattga aatctgttga gtaggcctgt       240
tattgtcgcc cccaggagac ggagaatctc gacggggggcg cagatgagat caacttattg       300

<210> SEQ ID NO 28
<211> LENGTH: 101
<212> TYPE: DNA
<213> ORGANISM: Artificial Sequence
<220> FEATURE:
<223> OTHER INFORMATION: Synthetic sequence: Amplification product
      obtained using the primers in SEQ ID NOs: 24 & 25 and an
      appropriate vector substrate
<220> FEATURE:
<221> NAME/KEY: misc_feature

```
<222> LOCATION: (48)..(53)
<223> OTHER INFORMATION: n is a, c, g, or t

<400> SEQUENCE: 28
cttggttttt ccaagagaag agcccgccat ggcggccgcg ggaattcnnn nnntcactag      60
tgaattcgcg gccgcctgct cttcgccgtc aaaaagacgg a                         101

<210> SEQ ID NO 29
<211> LENGTH: 100
<212> TYPE: DNA
<213> ORGANISM: Artificial Sequence
<220> FEATURE:
<223> OTHER INFORMATION: Synthetic sequence: Amplification product
      obtained using the primers in SEQ ID NOs: 24 & 25 and an
      appropriate vector substrate
<220> FEATURE:
<221> NAME/KEY: misc_feature
<222> LOCATION: (48)..(53)
<223> OTHER INFORMATION: n is a, c, g, or t

<400> SEQUENCE: 29
ccgtcttttt gacggcgaag tgcaggcggc cgcgaattca ctagtgannn nnngaattcc      60
cgcggccgcc atggcgggct cttctcttgg aaaaaccaag                           100

<210> SEQ ID NO 30
<211> LENGTH: 85
<212> TYPE: DNA
<213> ORGANISM: Artificial Sequence
<220> FEATURE:
<223> OTHER INFORMATION: Synthetic sequence: Consequence of digesting
      PCR product with Nt.BspQ1
<220> FEATURE:
<221> NAME/KEY: misc_feature
<222> LOCATION: (48)..(53)
<223> OTHER INFORMATION: n is a, c, g, or t

<400> SEQUENCE: 30
cttggttttt ccaagagaag agcccgccat ggcggccgcg ggaattcnnn nnntcactag      60
tgaattcgcg gccgcctgct cttcg                                           85

<210> SEQ ID NO 31
<211> LENGTH: 85
<212> TYPE: DNA
<213> ORGANISM: Artificial Sequence
<220> FEATURE:
<223> OTHER INFORMATION: Synthetic sequence: Consequence of digesting
      PCR product with Nt.BspQ1
<220> FEATURE:
<221> NAME/KEY: misc_feature
<222> LOCATION: (48)..(53)
<223> OTHER INFORMATION: n is a, c, g, or t

<400> SEQUENCE: 31
ccgtcttttt gacggcgaag tgcaggcggc cgcgaattca ctagtgannn nnngaattcc      60
cgcggccgcc atggcgggct cttct                                           85
```